United States Patent
Prpa et al.

(10) Patent No.: US 10,792,118 B2
(45) Date of Patent: Oct. 6, 2020

(54) STERILE IMPLANT TRACKING DEVICE, SYSTEM AND METHOD OF USE

(71) Applicant: Matrix IT Medical Tracking Systems, Inc., Racine, WI (US)

(72) Inventors: Branko Prpa, Pleasant Prairie, WI (US); Larry W. Donnelly, Scottsdale, AZ (US); Brandon M. Donnelly, Scottsdale, AZ (US)

(73) Assignee: MATRIX IT MEDICAL TRACKING SYSTEMS, INC., Racine, WI (US)

( * ) Notice: Subject to any disclaimer, the term of this patent is extended or adjusted under 35 U.S.C. 154(b) by 861 days.

(21) Appl. No.: 15/190,737

(22) Filed: Jun. 23, 2016

(65) Prior Publication Data

US 2016/0374775 A1 Dec. 29, 2016

Related U.S. Application Data

(60) Provisional application No. 62/183,489, filed on Jun. 23, 2015.

(51) Int. Cl.

| | |
|---|---|
| *G16H 10/60* | (2018.01) |
| *A61B 46/10* | (2016.01) |
| *A61B 90/98* | (2016.01) |
| *A61B 50/20* | (2016.01) |
| *A61B 34/20* | (2016.01) |
| *A61B 90/96* | (2016.01) |
| *G06F 19/00* | (2018.01) |

(52) U.S. Cl.
CPC .............. *A61B 46/10* (2016.02); *A61B 34/20* (2016.02); *A61B 50/20* (2016.02); *A61B 90/96* (2016.02); *A61B 90/98* (2016.02); *G06F 19/00* (2013.01); *G16H 10/60* (2018.01); *A61B 2034/2055* (2016.02); *A61F 2250/0089* (2013.01)

(58) Field of Classification Search
CPC ....................................................... G16H 10/60
See application file for complete search history.

(56) References Cited

U.S. PATENT DOCUMENTS

| | | | |
|---|---|---|---|
| 5,423,334 A | 6/1995 | Jordan | |
| 5,554,841 A | 9/1996 | Kost et al. | |
| 5,631,456 A | 5/1997 | Kost et al. | |
| 5,879,621 A | 3/1999 | Farles et al. | |
| 7,114,656 B1* | 10/2006 | Garver | A47F 9/048 235/462.46 |
| 8,146,825 B1* | 4/2012 | Prpa | A61B 90/98 235/470 |
| 2006/0256400 A1 | 11/2006 | Carnevali | |
| 2008/0033759 A1* | 2/2008 | Finlay | G06Q 10/06 705/3 |
| 2008/0281301 A1 | 11/2008 | DeBoer et al. | |

(Continued)

*Primary Examiner* — John A Pauls
(74) *Attorney, Agent, or Firm* — Husch Blackwell LLP

(57) ABSTRACT

A method of tracking a medical device includes creating a patient profile; creating an operating profile with at least one identified surgical site; providing a tracking assembly including a reader with a scanner, a housing enclosing the scanner and a medical drape; placing a medical device having an identifier over the reader; scanning the identifier of the medical device to electronically record the medical device data; associating the scanned medical device data with the at least one surgical site; and using the medical device on a patient on the at least one surgical site.

12 Claims, 30 Drawing Sheets

(56) References Cited

U.S. PATENT DOCUMENTS

| | | | |
|---|---|---|---|
| 2009/0317002 A1 | 12/2009 | Dein | |
| 2010/0044441 A1* | 2/2010 | Cohen | G01N 21/251 |
| | | | 235/469 |
| 2010/0076306 A1 | 3/2010 | Daigneault et al. | |
| 2010/0161345 A1* | 6/2010 | Cain | G06F 19/328 |
| | | | 705/2 |
| 2010/0200649 A1* | 8/2010 | Callegari | G06K 19/086 |
| | | | 235/375 |
| 2011/0171908 A1* | 7/2011 | Hua | H04W 76/10 |
| | | | 455/41.2 |
| 2011/0276340 A1 | 11/2011 | DeBoer et al. | |
| 2012/0193410 A1 | 8/2012 | Benetti | |
| 2012/0316987 A1* | 12/2012 | DeBusk | G06Q 10/08 |
| | | | 705/26.8 |
| 2014/0365235 A1 | 12/2014 | DeBoer et al. | |
| 2017/0300980 A1* | 10/2017 | Soldate | G06Q 30/06 |

* cited by examiner

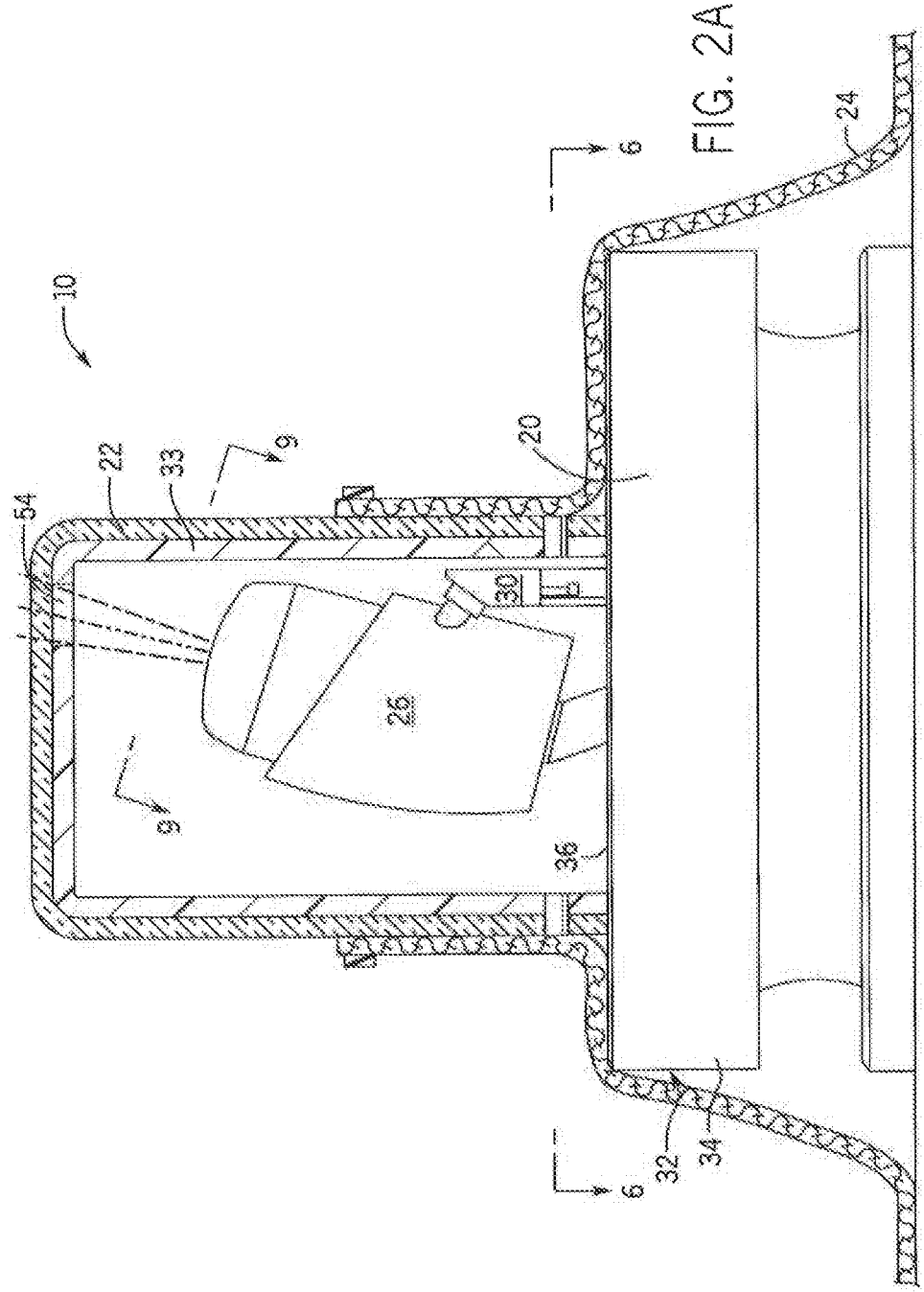

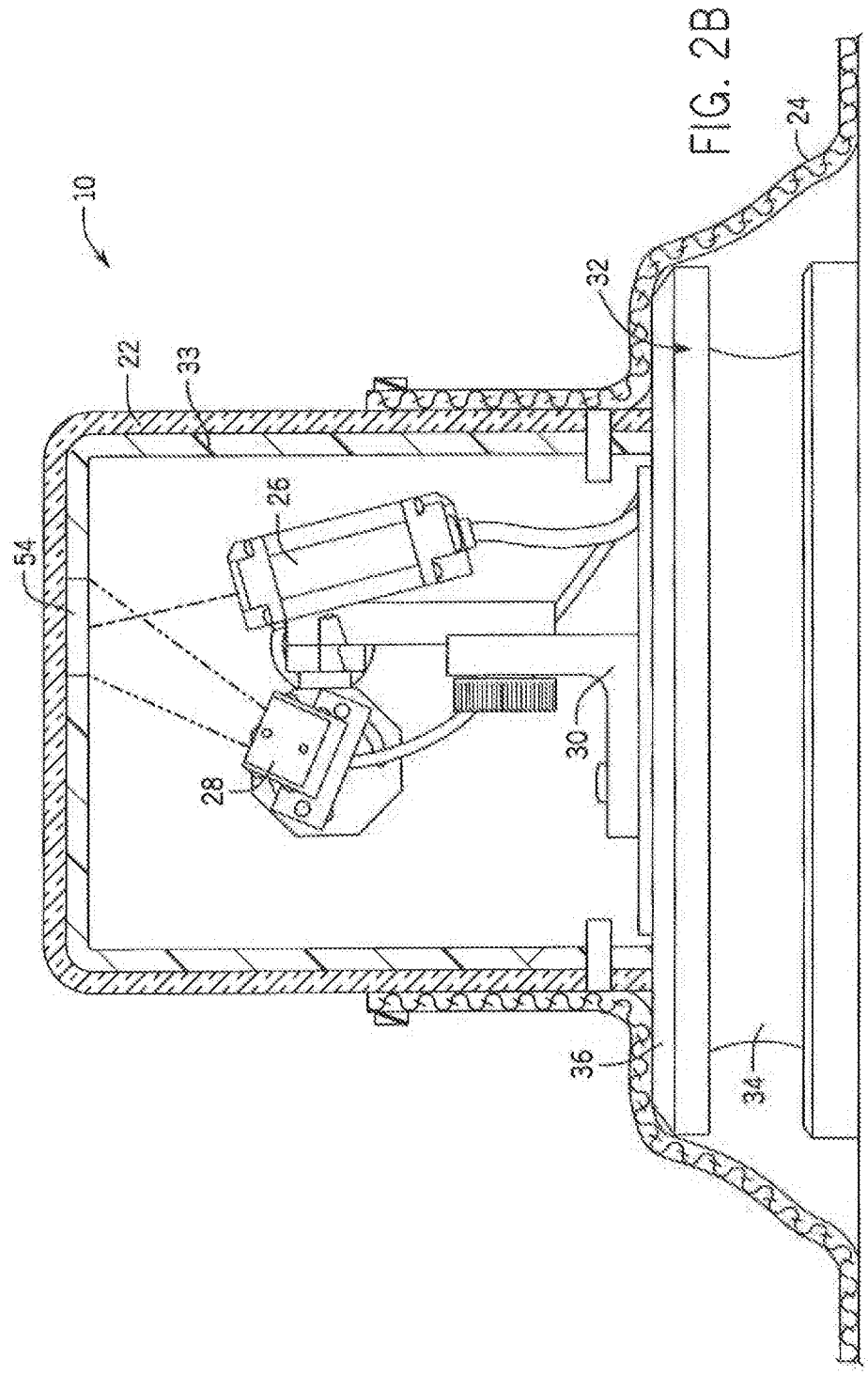

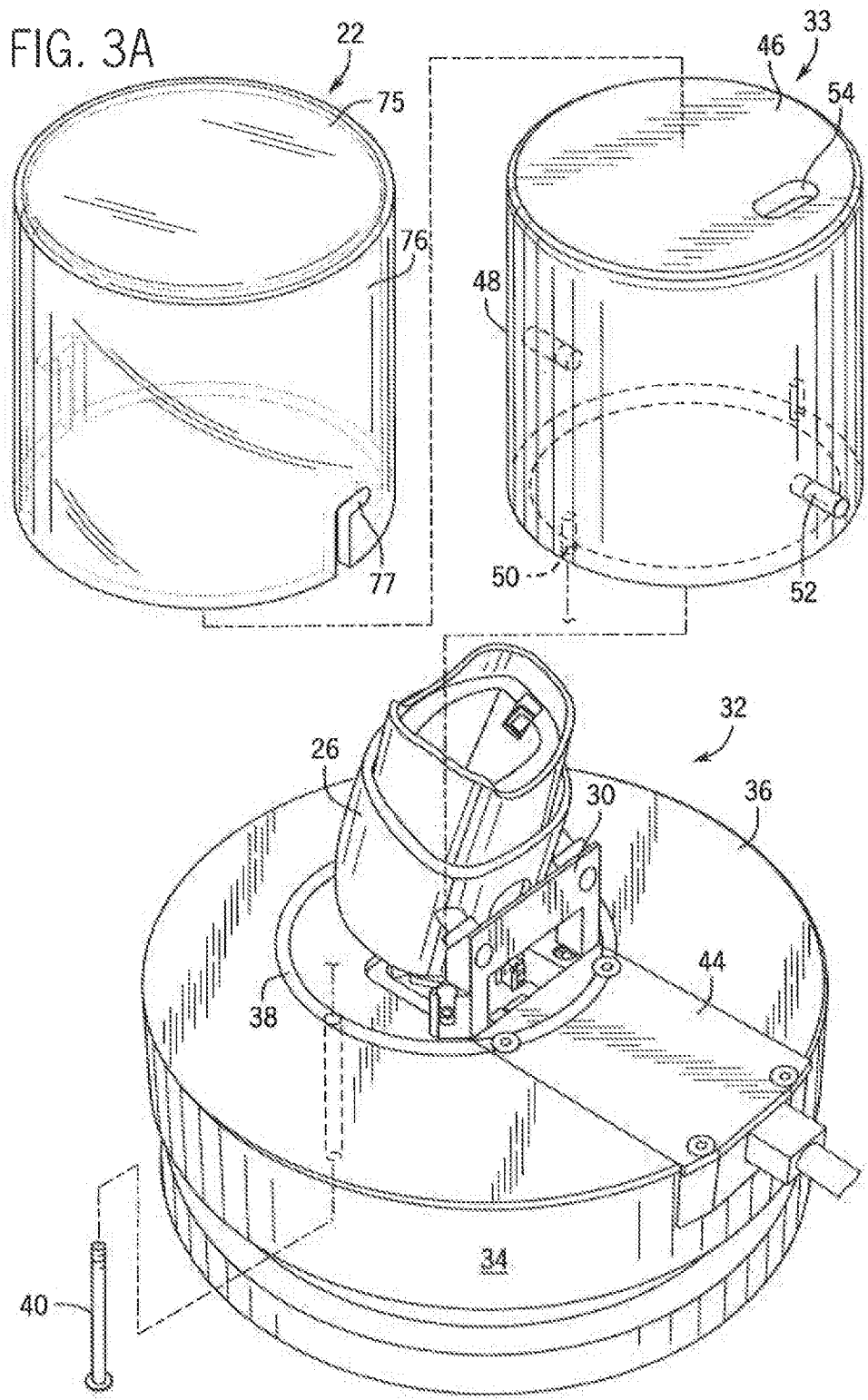

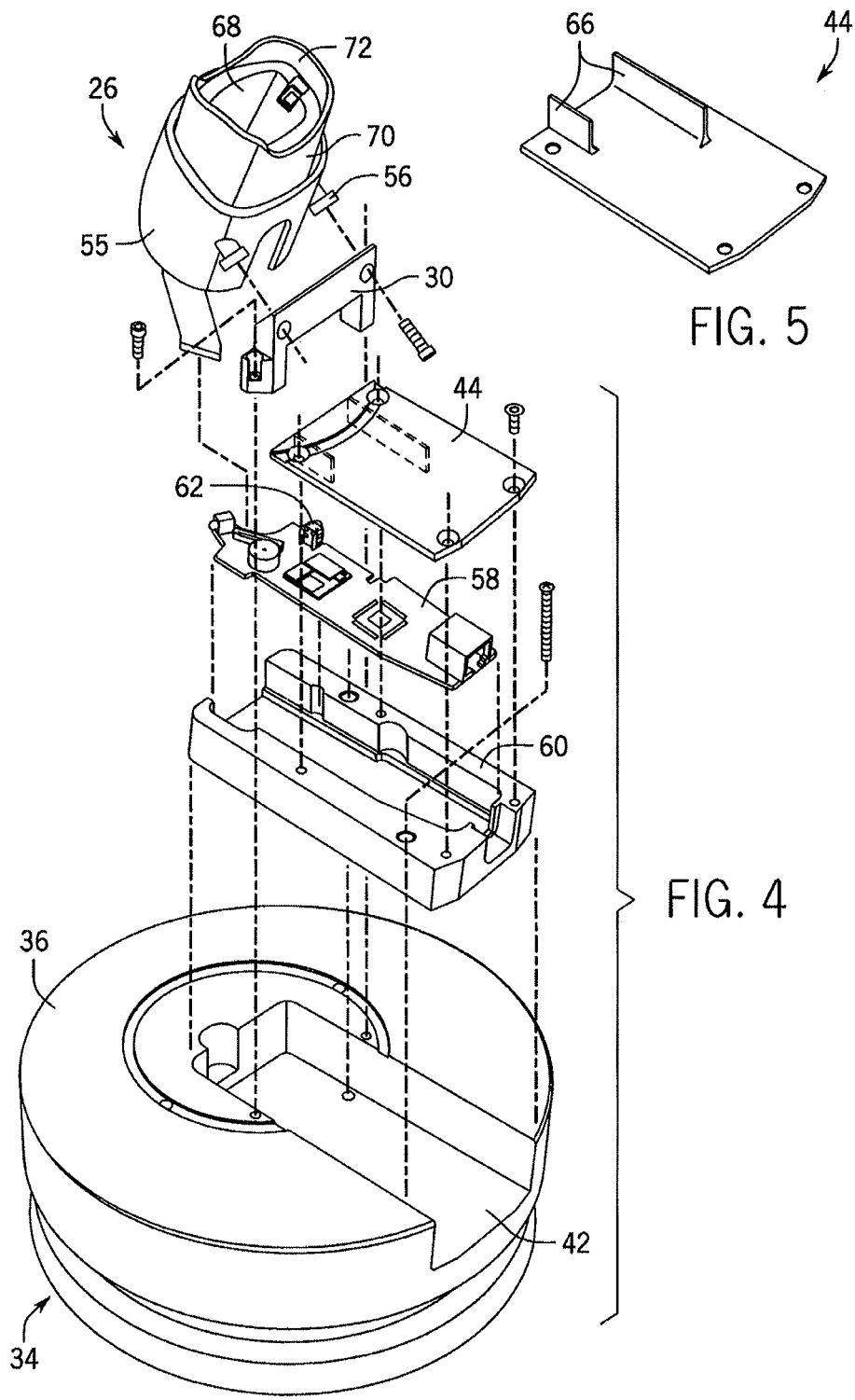

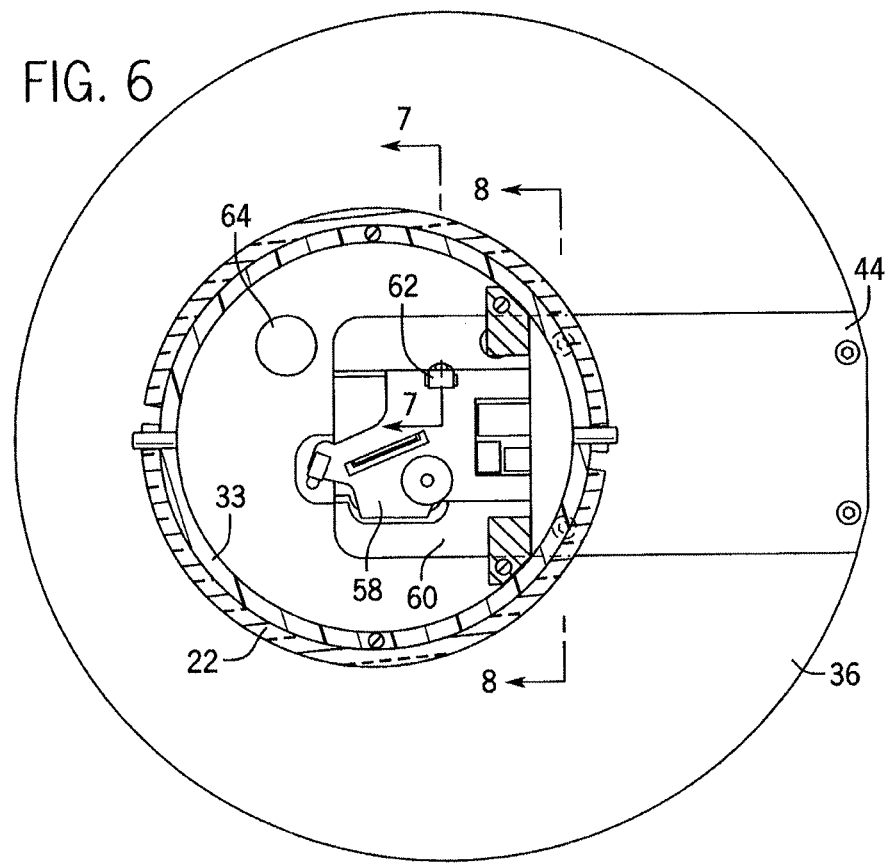
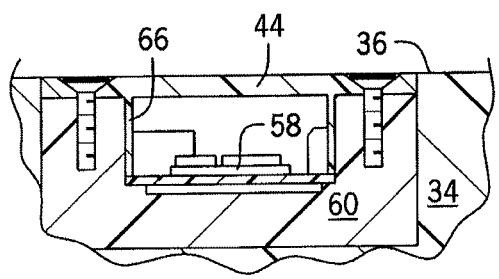
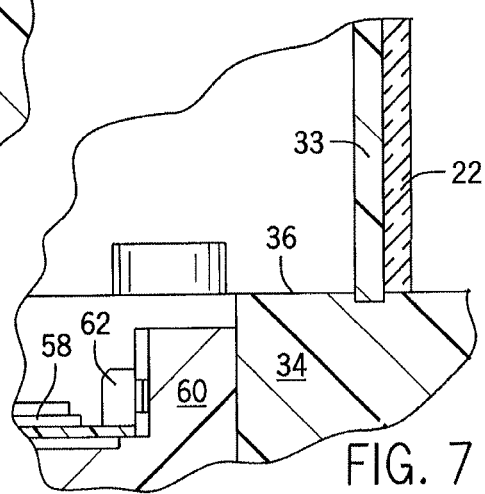

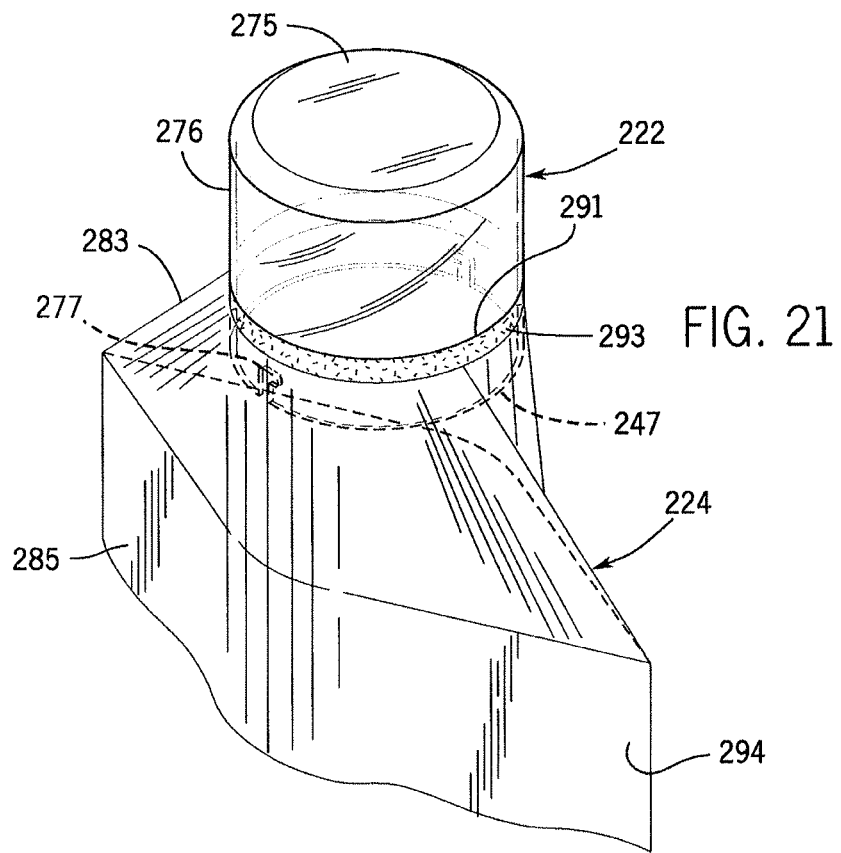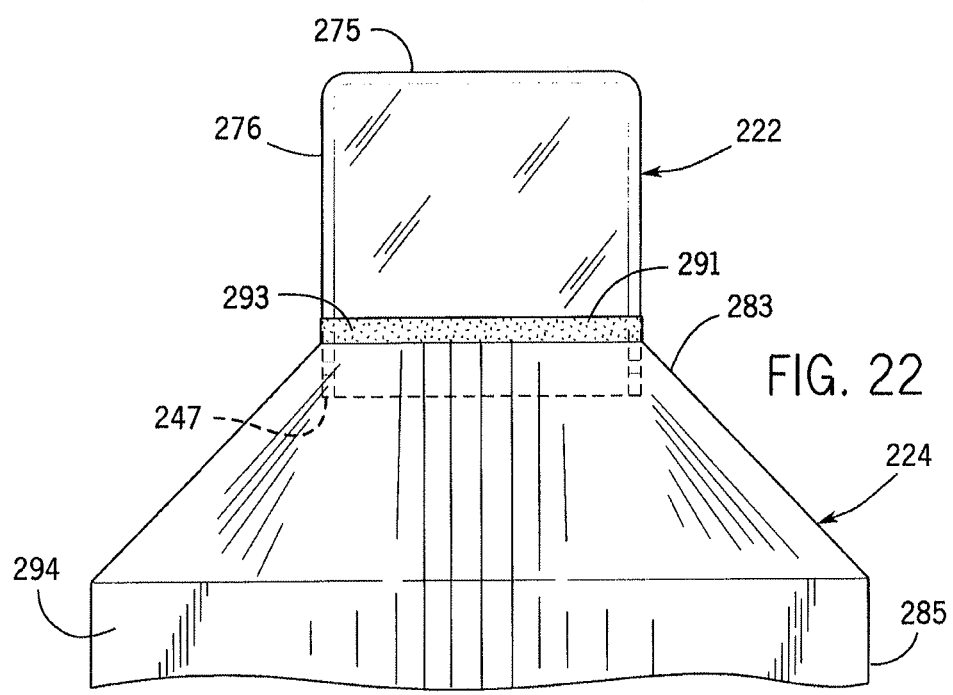

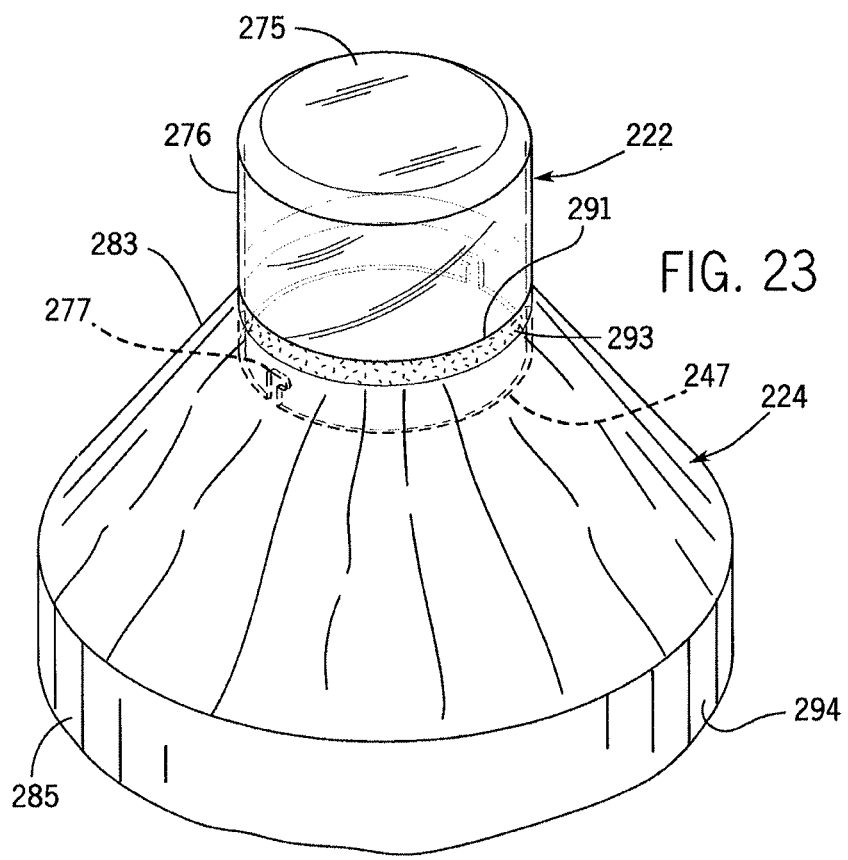
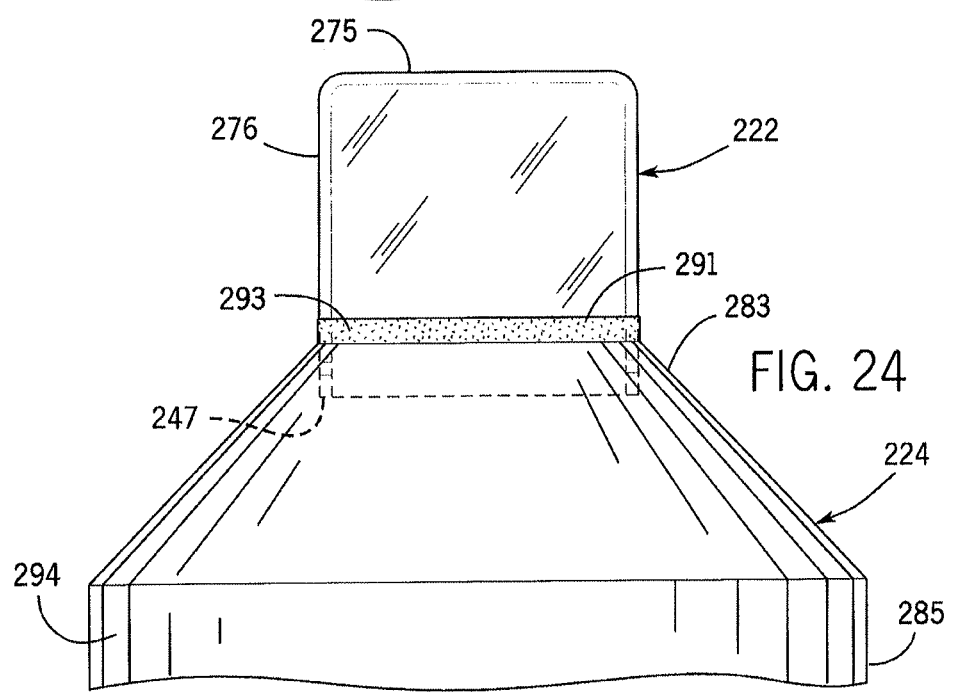

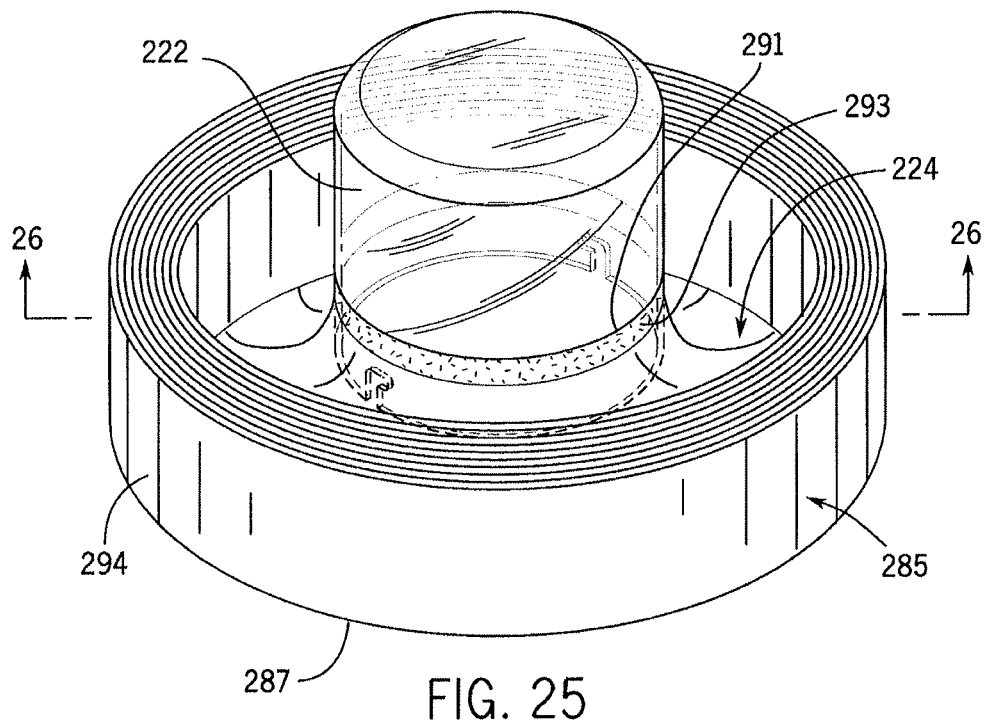
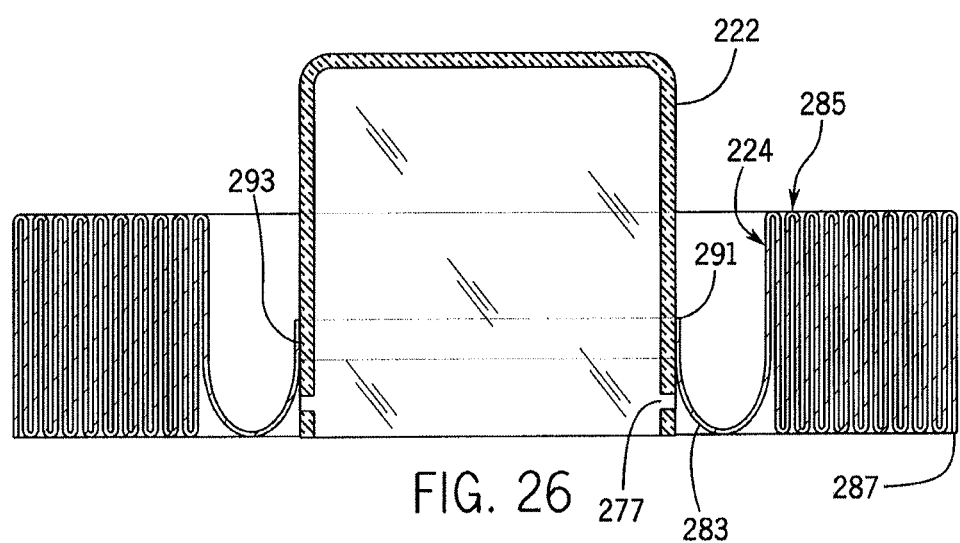

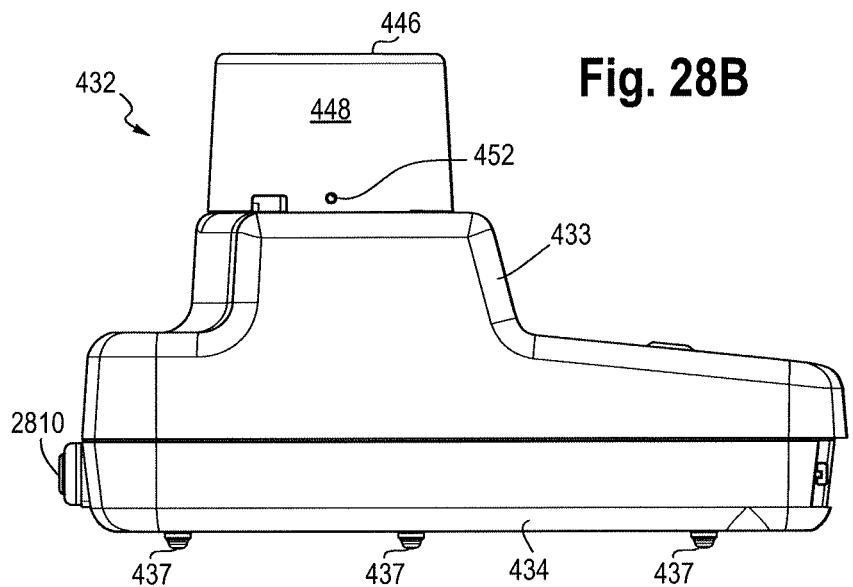
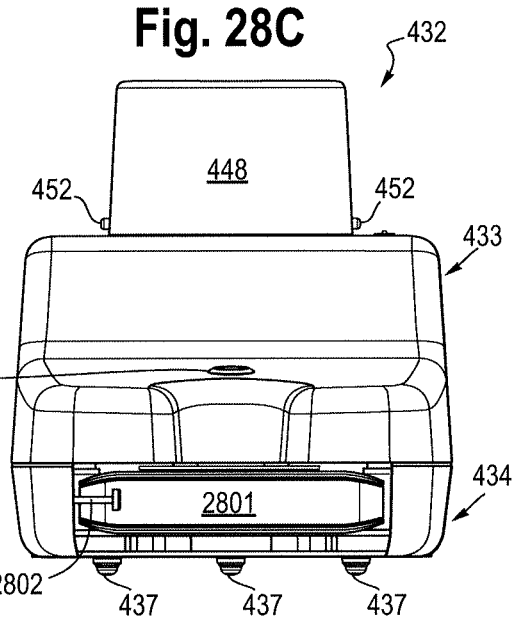
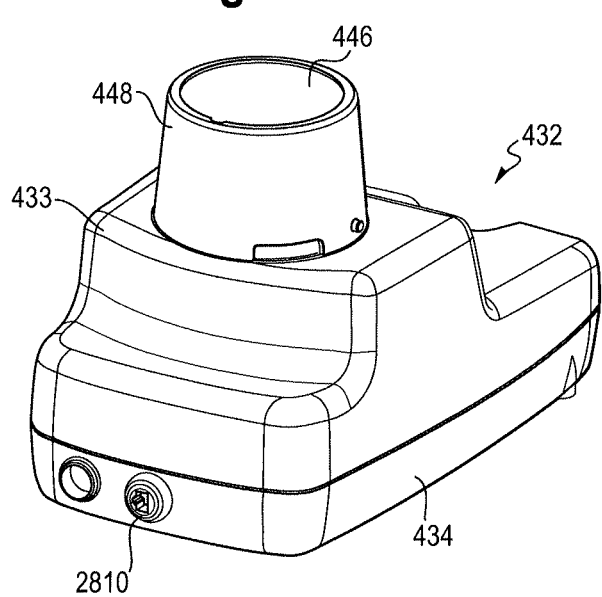

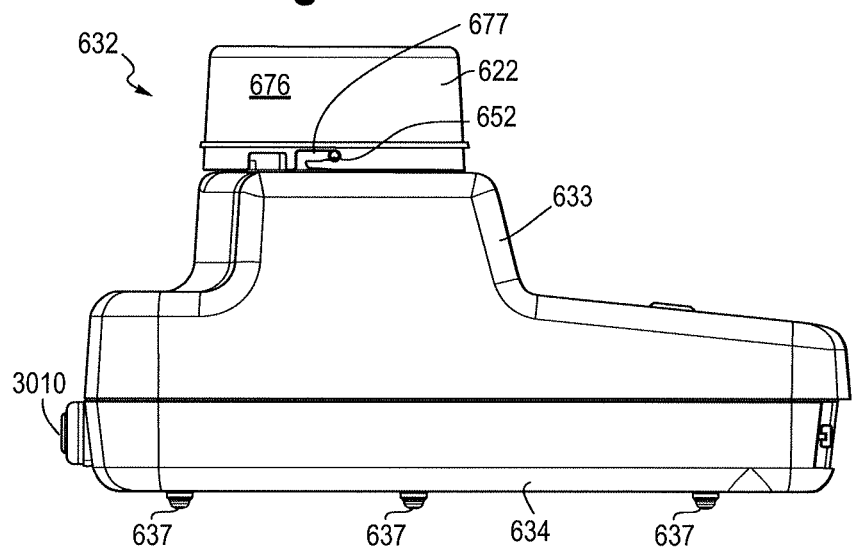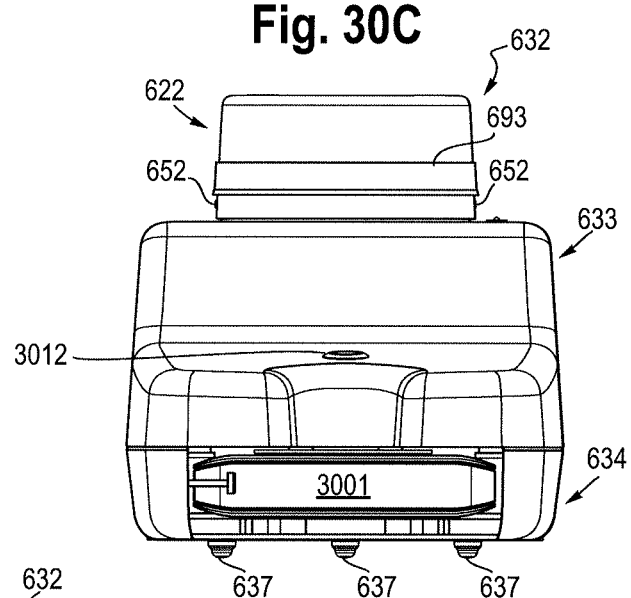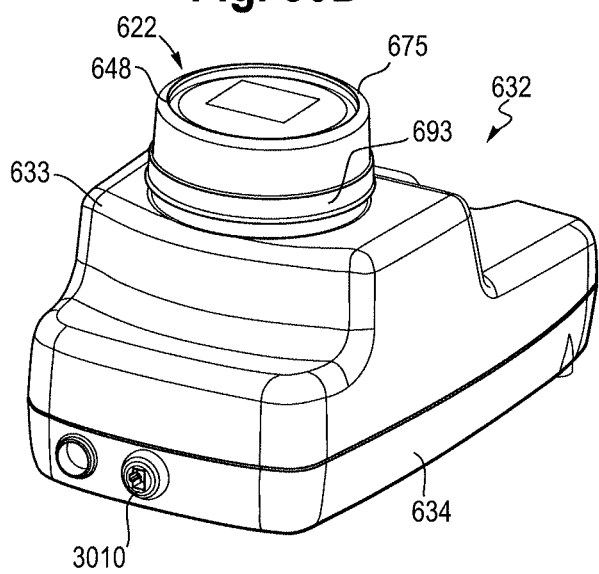

STERILE IMPLANT TRACKING DEVICE, SYSTEM AND METHOD OF USE

CROSS REFERENCE TO RELATED APPLICATION

This application claims the benefit of U.S. Provisional Patent Application No. 62/183,489 filed on Jun. 23, 2015, the entire content of which is incorporated by reference herein.

BACKGROUND

1. Field

This invention relates to an implant tracking system using an optical-based identification technique.

2. Background

Tracking and managing orthopedic implants, implant replacements and tools and other items used during a surgery is an important health issue. With over 50,000 annual implantable device failures resulting in patient hospitalization, injury or death, the Food and Drug Administration (FDA) was charged with creating mandates for the medical implant industry. In September 2013, the FDA passed the Unique Device Identification (UDI) Final Rule, which requires manufacturers to mark each implant with UDI information directly onto each implantable device; and for that information to be tracked throughout the implant's life cycle.

UDI is a common language that was standardized by the FDA for the healthcare industry to ensure that all stakeholders involved in the healthcare supply chain describe and document their devices utilizing standard nomenclature. Included in the UDI are manufacturer, part, lot, serial, expiration, as well as other pertinent information. Stakeholders involved in the healthcare supply chain include implant manufacturers who identify each part, hospitals that capture the information into the patients' health record, payers which reimburse for the procedure, regulatory agencies that surveil implant performance, patients who have a right to know about their implant. While no part of the FDA's UDI rule pertains to hospitals or ambulatory surgery centers (ASCs), they both play a pivotal role in the supply chain and stand to gain tremendously by the widespread adoption of the UDI rule. As the final interface with the patient, hospitals and ASCs provide the ideal landscape for supporting implant tracking and patient safety.

Typically each implant, and in some instances the tools and other items used during a surgery, contains a UDI which comprises a unique identification number, such as, for example, a manufacturer's identification and/or serial number, or other tracking number, such as, for example, a bar code, RFID, or other 2D marking. Whenever an implant is placed, the tracking/identification number is recorded as a permanent record in a database. In the future, this number can be referenced to track the age of the implant, the manufacturer for purposes of recall and adjustment, and can be used postmortem to identify a person having the implant. Similarly, when a tool is used, the tracking/identification number is recorded and marked as "used" so that at the end of a surgery, all used tools may be accounted for.

The unique identification number may be tracked by identifiers, such as unique labels or other indicia, applied to the product and/or packaging, and the labels may remain associated with the implant until the implant is used. In some cases, product labels include adhesive portions that can be applied to a chart or file of a patient to conveniently associate the medical device with a particular patient.

Identifiers may be any graphic that is capable of retaining identifying information. In some embodiments, the identifier is a one or two dimensional bar code suitable for scanning by an optical scanner such as a bar code reader. Any data matrix, barcode, QR code or any other code technology may be used as identifiers. The identifier may also be a radio frequency identification tag that is readable through radio frequency transmission generated by an independently powered RFID device. The identifier may also be an RFID tag that includes a transponder and is readable in response to a radio frequency signal transmitted to the RFID device. In some embodiments, the identifier is a human readable visual and/or tactile graphic such as alphanumeric characters that can be manually recorded in a database or chart.

It would be beneficial if physicians were able to obtain additional information about an implant and/or a patient from an implant identifier such as the manufacturer and model number of the device, the serial number of the device, the treating physician's name and contact information, and the patient's name, contact information, medical condition and treatment, among other relevant information.

Currently, difficulty arises in tracking medical devices. For example, such items are difficult to track due to a lack of adequate surface area for applying marks. Thus, in many instances, items are not tracked beyond their manufacturing facility, and implants may only be counted when reconciled for payment as one of many products that were not returned to a manufacturer for replenishment.

There is a strong and growing need to not only track medical devices/surgical tools and accessories, but to do so efficiently while maintaining a sterile operating environment. Therefore, if the tracking system involves a reader, such as a barcode scanner or RFID reader, then the reader itself needs to be sterile so as not to contaminate the medical device of which it is reading or the personnel operating the reader.

There is a further strong and growing need to not only track medical devices/surgical tools and accessories, but to do so in a way that associates these items with a particular surgical site and in a manner that alerts a surgeon/surgical tech if an item which is not implanted in a patient is unaccounted for at the end of a surgical procedure.

Further, despite current tracking efforts, most advanced healthcare institutions struggle to accurately identify patients with a defective implantable medical device. Conversely, the automotive industry may easily identify the owner of a vehicle with a recalled airbag that was installed over a decade ago.

Medical equipment may be sterilized by the use of chemical or physical agents, for example using hot steam, gas or gamma rays sterilization. However, these means may not be appropriate for more delicate medical equipment, such as a reader.

There exists a need for a sterile interface for use with a reader that allows for the efficient use of the reader in a sterile operating room environment.

SUMMARY

In an embodiment, the invention is an assembly for tracking implants comprising a (i) reader, (ii) medical drape, and (iii) computer. In an embodiment, communication between the reader and the computer is through a wireless system, including but not limited to Bluetooth. In an embodiment, the computer has software that allows for tracking and recording implant information. The software can be integrated and communicate with multiple systems including but not limited to electronic health records, electronic medical records, hospital and clinic databases containing patient information, databases containing scheduling information, databases containing physician and medical staff information, databases containing hospital inventory information, payer systems, databases and records of the manufacturer of the medical device, insurance and reimbursement systems, and government databases, such as the Food and Drug Administration.

In an embodiment, the reader comprises a (a) scanner, (b) housing structure comprising a cover and base, and optionally (c) transparent sterile sheath having a top surface and side walls and encases the cover of the housing structure. The cover has an aperture through the top surface of the cover. The medical drape is attached to the side walls of the transparent sterile sheath. The computer is in communication with the reader.

In an embodiment, the invention is a reader comprising a scanner, a scanner mounting structure supporting the scanner, a housing structure comprising a cover and base, and an optional transparent sterile sheath encasing the cover of the housing structure. The base comprises a top surface to receive the scanner mounting structure, an inset groove to receive the cover, an inset channel extending radially from the cover to the edge of the top surface of the base, and a removable channel cover. The scanner mounting structure is attached to the base, and both the scanner and mounting structure are enclosed in the housing structure.

In an embodiment, the invention is a method of using a reader comprising the steps of providing a reader, placing an implant having an identifier onto the top surface of the transparent sterile sheath above the aperture, and scanning the identifier of the implant to electronically record the stored data.

In an embodiment, the invention is a tracking assembly comprising a reader comprising, a housing structure that includes a base and a cover, a scanner having a scanner housing, where the scanner housing is at least partially positioned in a cavity provided in the base; and an aperture provided in the cover, where the cover is configured to receive a transparent sterile sheath to at least partially encase the cover.

In an embodiment, the invention is a tracking assembly comprising, a reader comprising, a scanner; a scanner mounting structure supporting the scanner; a housing structure that includes a cover with an aperture on a top surface of the cover and a base secured to the cover, where the housing structure is configured to receive a one or more coverings to at least partially enclose the housing structure, where the scanner mounting structure is secured to the base, and where the scanner and scanner mounting structure are substantially enclosed in the housing structure.

In an embodiment, the invention is a method of using a tracking assembly comprising the steps of: providing a tracking assembly comprising a reader that includes a scanner and a housing structure with a cover having an aperture on a top surface; covering the cover with a transparent sterile sheath; placing an implant having an identifier over the aperture; and scanning the identifier of the implant to electronically record the implant data.

In an embodiment, the invention is a method of tracking a medical device comprising: creating a patient profile; creating an operating profile comprising at least one surgical site; providing a tracking assembly comprising a reader, the reader comprising a scanner, a housing enclosing the scanner, and a medical drape; placing a medical device having an identifier over the reader; scanning the identifier of the medical device to electronically record the medical device data; associating the scanned medical device data with the at least one surgical site; and using the medical device on a patient on the at least one surgical site.

In an embodiment, the invention is a method of tracking a medical device comprising: providing a tracking assembly comprising a reader, the reader comprising a scanner, a housing enclosing the scanner, and a medical drape; covering the reader with the medical drape; placing the reader covered with the medical drape in a sterile field; providing a computer; creating a patient profile using the computer, wherein the patient profile includes a value for a medical procedure start time; creating an operating profile comprising at least one surgical site using the computer; placing a medical device having an identifier over the reader; scanning the identifier of the medical device to electronically record the medical device data in memory in the computer, wherein the scanner communicates with the computer using Bluetooth; associating the scanned medical device data with the at least one surgical site using the computer, whereby the scanned medical device is assigned a status of assigned; using the medical device on a patient on the at least one surgical site; changing the status of the medical device to a status selected from the group consisting of unassigned, broken, discarded or implanted; and entering a value for a medical procedure end time into the patient profile.

BRIEF DESCRIPTION OF THE DRAWINGS

The invention is described generally with reference to the drawings for the purpose of illustrating certain embodiments only, and not for the purpose of limiting the scope of the invention. In the drawings, like numerals are used to designate like parts throughout the same.

FIG. 2A is a sectional view of the assembly of FIG. 1.

FIG. 2B is a sectional view of an embodiment of the assembly of FIG. 1.

FIG. 3A is an exploded view of the reader of FIG. 1.

FIG. 4 is an exploded view of the reader of FIG. 3A without the cover.

FIG. 5 is a bottom view of the removable channel cover.

FIG. 6 is a sectional view of the reader of FIG. 2A.

FIG. 7 is a sectional view of FIG. 6.

FIG. 8 is a sectional view of FIG. 6.

FIG. 21 is a perspective view of an embodiment of the sheath and drape of FIG. 20.

FIG. 22 is a side view of the sheath and drape of FIG. 21.

FIG. 23 is a perspective view of another embodiment of the sheath and drape of FIG. 20.

FIG. 24 is a side view of the sheath and drape of FIG. 23.

FIG. 25 is a perspective view of the sheath and drape of FIG. 20, in an exemplary folded configuration.

FIG. 26 is a sectional side view taken at line 26-26 of FIG. 25.

FIG. 28B is a side view of the reader of FIG. 28A.

FIG. 28C is a front view of the reader of FIG. 28A.

FIG. 28D is a rear perspective view of the reader of FIG. 28A.

FIG. 30B is a side view of the reader of FIG. 30A.

FIG. 30C is a front view of the reader of FIG. 30A.

FIG. 30D is a rear perspective view of the reader of FIG. 30A.

DETAILED DESCRIPTION

The present disclosure provides a system for tracking implants (e.g., screws, plates, cages, nuts, rods, etc.). An advantage of the present method for tracking an implant is a vast improvement in sterility and efficiency over current tracking methods. Typically, in an operating room, the patient to receive the implant is lying on an operating table in the center of the room. There is a sterile field extending two to three feet radially from the operating table. The present assembly comprising a reader assembled with transparent sterile sheath and sterile medical drape may be inside the sterile field. A computer, in communication with the reader, is typically outside the sterile field and, in certain instances, operated by a person outside the sterile field. The operator of the computer can log into the software which is password protected as the surgery is beginning and input certain information such as the patient's name, etc., to save time.

The present method increases efficiency in the operating room by decreasing the time spent during operation on scanning and tracking every implant going into the patient while maintaining a sterile environment. For example, during spinal surgery, the surgeon requests numerous screws, plates, hooks, and cages, and each implant must be tracked by recording its manufacturer's information, lot number, serial number, etc., in addition to where that screw is implanted in the spine. Using the present assembly, the surgeon would request a screw, for example, having an identifier on its surface. The assistant would take the screw out of the sterile package and set the screw down on top of the transparent sterile sheath above an aperture on the reader. The reader would beep to indicate a successful scan of the identifier, and the assistant would hand the screw to the surgeon for implantation. The information (manufacturer's information, lot number, serial number, etc.) obtained from the identifier by the reader is transferred to the computer and the user of the computer can input data that indicates where the screw was implanted according to the surgeon's instruction. The location data of where the implant is placed in the patient may be aided by the software, which pulls up an anatomical image where the user of the computer can then just select visually where the implant was inserted.

Table Top Implant Tracking Assembly

Figure 1:
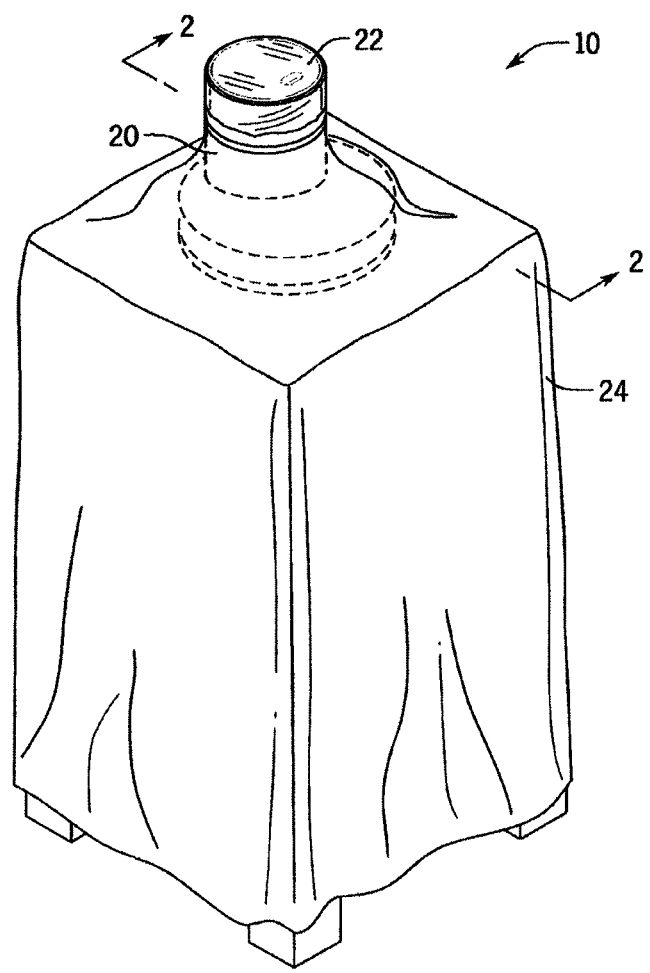
FIG. 1 is a schematic of an assembly of an embodiment of the invention including a reader and medical drape.

FIG. 1 depicts an embodiment of an implant tracking assembly 10 which includes reader 20 and medical drape 24. FIG. 1 shows reader 20 comprising an optional transparent sterile sheath 22 that fits, preferably snugly, over the top surface of reader 20. Assembly 10 includes medical drape 24 which is temporarily attached to and extends radially from the side walls of the transparent sterile sheath 22 to cover the remaining elements of the reader, such as possible electrical cords and control panels, among other things. Assembly 10 includes a computer 25 (not shown) in communication with reader 20. Although FIG. 1 shows reader 20 placed on a table, the table is not part of the assembly 10. The reader device in assembly 10 may be a table top reader, a handheld reader, or a table top-handheld reader. The implant tracking assembly 10 can include one or more coverings to provide limitation of contaminants to and/or from reader 20, where the one or more coverings can include the transparent sterile sheath 22 and medical drape 24.

Table Top Reader

FIG. 2A is a sectional view of reader 20. Reader 20 includes scanner 26, scanner mounting structure 30, and housing structure 32 including cover 33 and base 34. As seen in FIGS. 2A-4, base 34 of housing structure 32 includes a base top surface 36 to receive the scanner mounting structure 30, and inset groove 38 to receive the bottom edge of cover 33. One or more vertical pins 40 may extend up from the bottom of the base through the inset groove 38. The shape of the base may be circular as shown in FIG. 1, but as one skilled in the art would understand, the disclosure is not limited to a circular base. In addition, in at least some embodiments, base 34 includes a diameter DI that extends between about 6 inches to about 10 inches. Further, base 34 can weigh between about one pound to about four pounds. FIG. 2A shows an embodiment where the base has a track creating a lip or shelf that allows for easy transport or mobility of the reader by a user inserting their fingers into the track and picking up the reader. Further, cover 33 and base 34 can be integrally formed, although the separability of cover 33 and base 34 can allow for insertion/installation of various components inside housing structure 32, in at least some embodiments, an alternate access may be provided to facilitate access for insertion of one or more components therein if cover 33 and base 34 are integrally formed.

FIG. 3A is an exploded view of housing structure 32 and transparent sterile sheath 22. Housing structure 32 further includes cover 33. Cover 33 includes cover top surface 46 and side wall 48, as seen in FIG. 3A. In an embodiment, cover top surface 46 is circular and thus the side wall 48 is in the shape of a cylinder. Alternatively, cover top surface 46 may be square or rectangular, yielding four side walls 48. Side wall 48 may have at least one radial pin 52 extending radially out from the side wall 48. The cover top surface 46 has an aperture 54 that may be circular, oblong, square, or any other shape that allows the reader device to properly scan a medical device placed above aperture 54. Side wall 48 may have at least one pin hole extending vertically into side wall 48 to receive vertical pin 40. Equivalents of pins are screws, bolts, nails, etc. In an embodiment, cover 33 is engaged with inset groove 38 of base 34 and vertical pin 40 is engaged with pin hole 50 of cover 33, securing cover 33 from any lateral movement. Cover 33 may sit in the center of base 34 or, more preferably, off center.

Housing structure 32 is made of an opaque material such as from a dense molded plastic, preferably a dark color, more preferably black. Utilizing a darker color can serve to reduce light noise, such as reflections of light, which can hinder the reader's ability to provide effective scans. Although in at least some embodiments, one or more portions of housing structure 32 can be comprised of materials other than plastic, as well as lighter colors.

Figure 10:
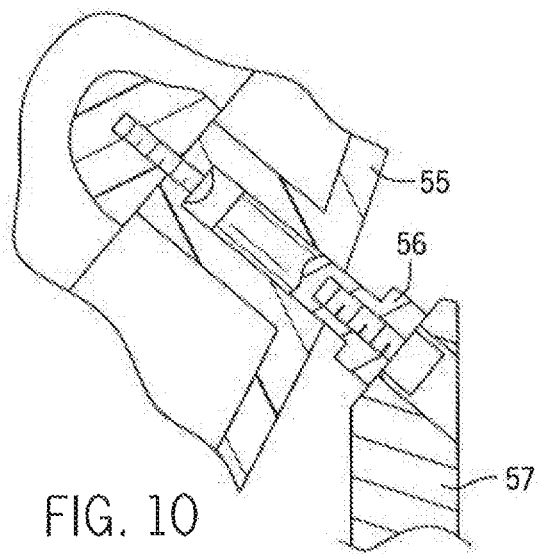
FIG. 10 is a sectional view of FIG. 9.

FIG. 4 is an exploded view of base 34, scanner mounting structure 30, and scanner 26. In an embodiment, scanning mounting structure 30 is bolted or otherwise securely fastened to a top surface of removable channel cover 44. Alternatively, scanning mounting structure 30 is bolted to base top surface 36 of base 34. Scanner 26 is housed in scanner housing 55, which is attached to scanning mounting structure 30 by screws that are received into receptacles 56 of scanner housing 55 (see FIG. 10). The position of scanner 26 is locked on the focal point of scanner 26, which is 1-3 millimeters (mm), preferably 1-2 mm, above the top surface of cover 33 in the area above aperture 54. When reader 20 comprises transparent sterile sheath 22, the focal point is on the surface of transparent sterile sheath 22 in the area above aperture 54. Alternatively, scanner 26 may be manufactured with adjustable knobs to allow a user to manually adjust the position of the scanner for an optimal read, as shown in FIGS. 2B and 3B.

Figure 3B:
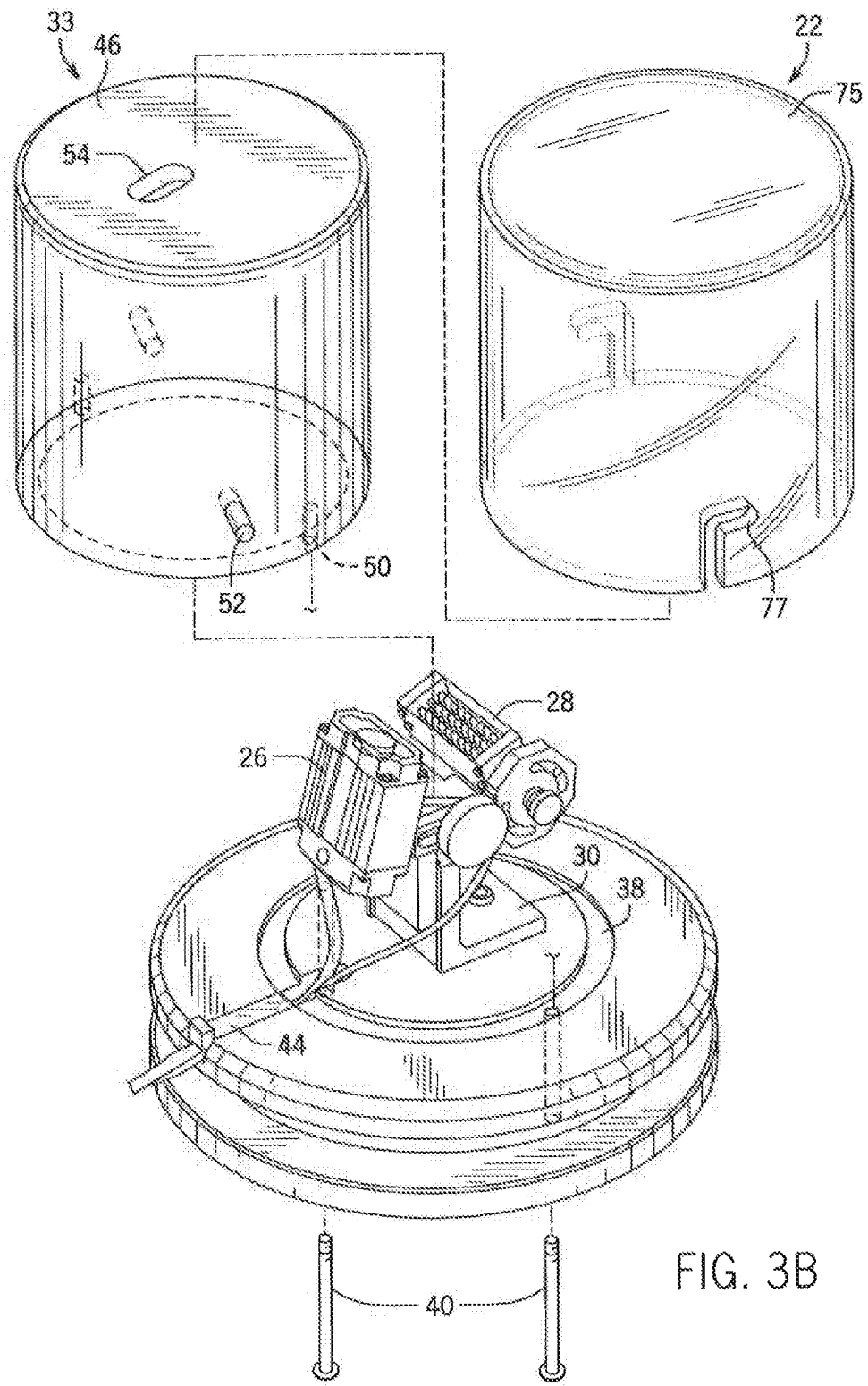
FIG. 3B is an exploded view of an embodiment of the assembly of FIG. 1.

Base 34 includes an inset channel 42 extending radially from the scanner mounting structure 30 to the edge of base 34 where the electrical cords from scanner 26 lie in inset channel 42 and extend out to a power source, control panel, or other appropriate source, as shown in FIG. 3B. Preferably, as shown in FIG. 4, inset channel 42 houses circuit board 58 which is in communication with scanner 26 and computer 25, typically, via electrical cords or wirelessly. In an embodiment, circuit board 58 is equivalent to the circuit board found in Motorola Symbol D56707-DP.

Circuit board 58 is securely positioned in inset channel 42 in circuit board mold 60. Circuit board mold 60 is designed such that the outer surface matches the shape of inset channel 42 and the inner surface matches that of the shape of circuit board 58. Circuit board mold 60 is secured to base 34 by screws or pins and removable channel cover 44 is secured to circuit board mold 60 by screws or pins. In an embodiment, circuit board 58 comprises button 62, which activates scanner 26 to take a scan upon depressing button 62. The inner surface of circuit board mold 60 is designed such that when circuit board 58 is positioned in circuit board mold 60, button 62 is constantly depressed into the "on" position, which can be seen in FIG. 7.

Removable channel cover 44 is designed such that when in place it is merely a part of the top surface of the base. Removable channel cover 44 may be removed and slid, snapped, or placed back into place covering inset channel 42. FIG. 5 is a bottom view of an embodiment of removable channel cover 44. Removable channel cover 44 has two perpendicular slats 66, which engage with the inner surface of circuit board mold 60. FIG. 8 is a sectional of FIG. 6 that shows removable channel cover 44 further secured in place by screws which extend into circuit board mold 60. FIG. 6 also shows perpendicular slats 66 of removable channel cover 44 engaged with the inner surface of circuit board mold 60.

FIG. 6 is a sectional view of FIG. 2. In an embodiment, magnet 64 is positioned inside cover 33 and is attached to base 34 or scanner housing 55. Most preferably, magnet 64 is built into base 34. Base 34 has a cut out specifically for magnet 64 to be placed into such that magnet 64 is flush with the base top surface 36. Magnet 64 is positioned off center and closest to the side of button 62. Magnet 64 has sufficient strength to allow scanner 26 to take a scan only when a user places a scannable object in the focal point of scanner 26.

Figure 9:
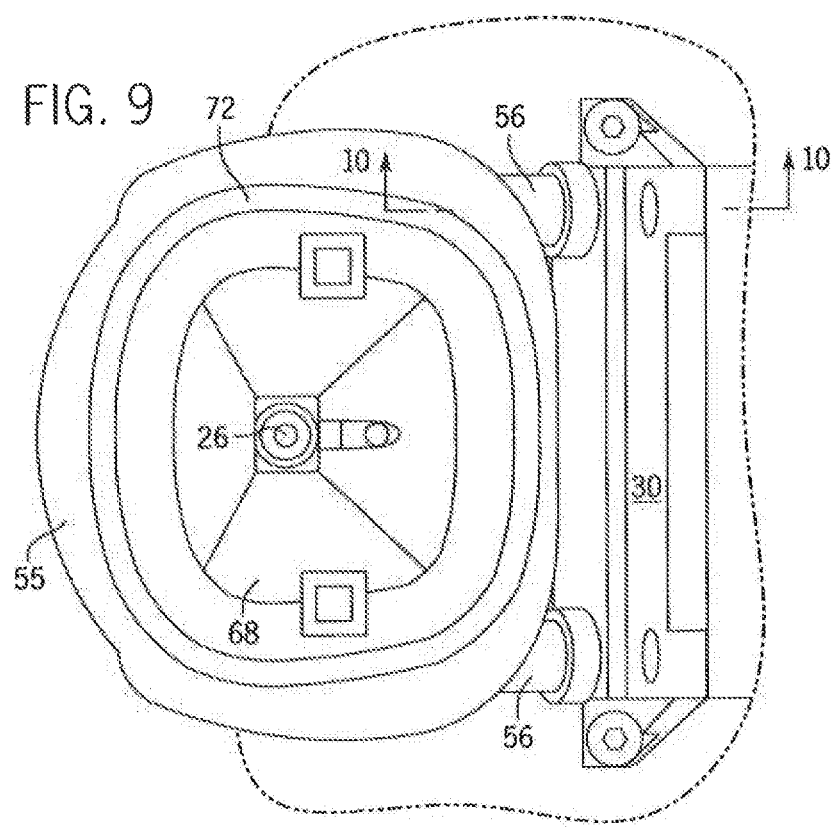
FIG. 9 is a top view of the scanner in FIG. 1.

FIG. 9 is a top view of scanner 26. Scanner 26 has conical walls 68 inside scanner housing 55. Scanner housing 55 includes shield 70, which extends beyond conical walls 68. Preferably, shield 70 comprises shield wings 72, which extend further on two opposite sides (see FIG. 4).

In an embodiment, scanner 26 is capable of reading identifiers such as conventional barcodes, etched matrixes, or any other optical indicator on an implant. In an embodiment, scanner 26 is equivalent to the scanner in Motorola Symbol DS6707-DP. In an embodiment, the reader further comprises a light emitting diode (LED) 28 for enhancing the visual indication of scanner 26, as shown in FIGS. 2B and 3B.

In an embodiment, reader 20 comprises an optional transparent sterile sheath 22 as shown in FIGS. 3A and 3B which encases cover 33 of reader 20. Transparent sterile sheath 22 can be partially or completely transparent, while in at least some embodiments, transparent sterile sheath 22 can be provided without transparent portions, provided that scanner 126 includes the capability to scan identifiers through the level of transparency provided by transparent sterile sheath 22. In at least some embodiments, sterile sheath 22 can be at least partially opaque, with the exception of at least a portion that covers aperture 54. Transparent sterile sheath 22 has sheath top surface 75 and sheath side wall 76. Preferably, sheath top surface 75 is slightly convex to deflect ambient light. In at least some embodiments, the convex portion of sheath top surface 75 can be substantially limited to the portion covering aperture 54. The degree of convexity is such that the transparent sheath reflects ambient light that interferes with the reader. Ambient light is background light typically present in an operating room. In an embodiment, sheath side wall 76 has at least one radial pin slot 77 designed to receive radial pin 52 of cover 33. FIG. 3A shows an embodiment in which two radial pin slots 77 are in an inverted "L" shape, such that when radial pin 52 of cover 33 engages with the radial pin slots 77 and the transparent sterile sheath 22 is twisted, it temporarily locks the transparent sterile sheath 22 in place by hindering vertical movement. One skilled in the art would understand the transparent sterile sheath could be temporarily locked into place over cover 33 in various manners. Alternatively, transparent sterile sheath 22 may just rest over cover 33 without any mechanism to lock the sheath in place.

Transparent sterile sheath 22 is designed such that when transparent sterile sheath 22 is engaged with housing structure 32 the area of sheath top surface 75 directly above aperture 54 of housing structure 32 is at the focal point of scanner 26. Placement of an implant with an indicator directly on the sheath top surface 75 directly above aperture 54 allows for the scanner to read the indicator without an operator having to hover the implant device over aperture 54 and search for the focal point of the scanner 26.

In an embodiment, transparent sterile sheath 22 is formed of a single piece of rigid transparent plastic. In an embodiment, transparent sterile sheath 22 is formed of a non-conductive, flexible, easily distortable, resilient material, which can be sterilized. Preferably, transparent sterile sheath 22 is disposable, such that transparent sterile sheath 22 is disposed of after identifiers have been received for all the medical devices used on and/or implanted in a single patient during an operation.

The thickness of transparent sterile sheath 22 is such that does not interfere with the reader device's ability to obtain data from an identifier on a medical device. Transparent sterile sheath 22 may be made of one or more of an elastomer, plastic, rubber, polyethylene, or polypropylene, among other materials that result in a functioning transparent sterile sheath 22 of the invention. In an embodiment, transparent sterile sheath 22 is made of a rigid, transparent plastic such as polycarbonate.

Transparent sterile sheath 22 may have additional properties that enhance the reader device's abilities. For example, in an embodiment, the sheath top surface 75 has magnifying abilities to allow a reader device to gather information from a smaller identifier such as a barcode or a 2D-grid or matrix the size of 2 millimeters (mm) by 2 mm, and even 1.4 mm by 1.4 mm. In an embodiment, the transparent sterile sheath 22 adheres to reader 20 such that the seal between transparent sterile sheath 22 and cover top surface 46 creates a vacuum between transparent sterile sheath 22 and the reader device. A vacuum between reader 20 and transparent sterile sheath 22 allows for improved reading of reader 20.

Assembly 10 comprising table top reader 20 further increases the efficiency of implant tracking by allowing a user to place the implant having the identifier on the surface of a transparent sheath for an accurate, automatic scan of the identifier. The user is not having to spend precious time waving/hovering the implant in front of a handheld reader to find the focal point of the scanner to obtain a scan during surgery. The inventive structure of reader 20 provides an efficient and sterile implant tracking device.

In an embodiment, a tabletop reader is completely wireless. In an embodiment, a tabletop reader is battery powered.

In an embodiment, a tabletop reader can be used as a standalone device or the tabletop reader can be used to integrate with one or more additional systems and databases, such as hospital systems, manufacture systems, third-party payers, and government agencies.

Handheld Reader

Figure 11:
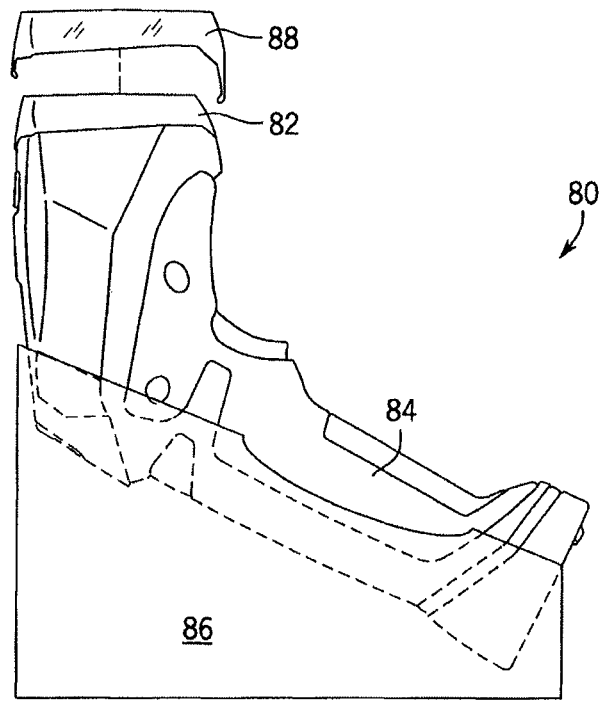
FIG. 11 is a schematic of a handheld reader and cradle of an embodiment of the invention.

FIGS. 11-14 are embodiments of an assembly comprising handheld reader 80 including reader lens 82 and handle 84. Handheld reader 80 contains an optical scanner. In an embodiment, the optical scanner is equivalent to that found in Motorola Symbol DS6707-DP. FIG. 11 is an embodiment of an assembly comprising a handheld reader 80 positioned in cradle 86, wherein handheld reader 80 is detachably connected to the cradle. Handheld reader 80 further comprises transparent sterile lens cover 88 which allows for an implant bearing an identifier to come into close proximity to the lens cover 88 for scanning without compromising the implant's sterility. Transparent sterile lens cover 88 may have magnifying abilities to allow the reader device to gather information from a smaller barcode or a 2D-grid or matrix the size of 2 millimeters (mm) by 2 mm, and even 1.4 mm by 1.4 mm. The focal point of the scanner is just above (1-2 mm) the surface of transparent sterile lens cover 88.

Figure 12:
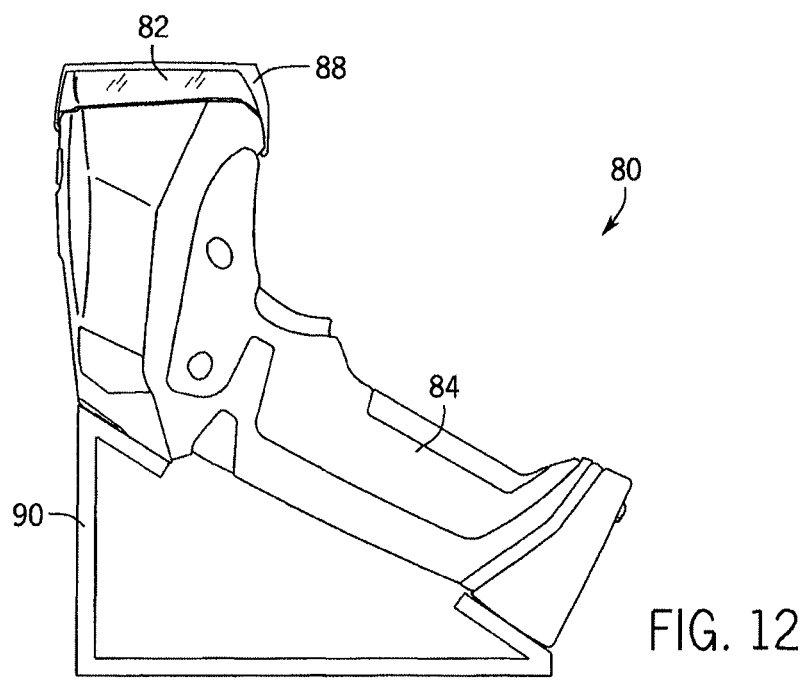
FIG. 12 is a schematic of the handheld reader and a base structure.
Figure 13:
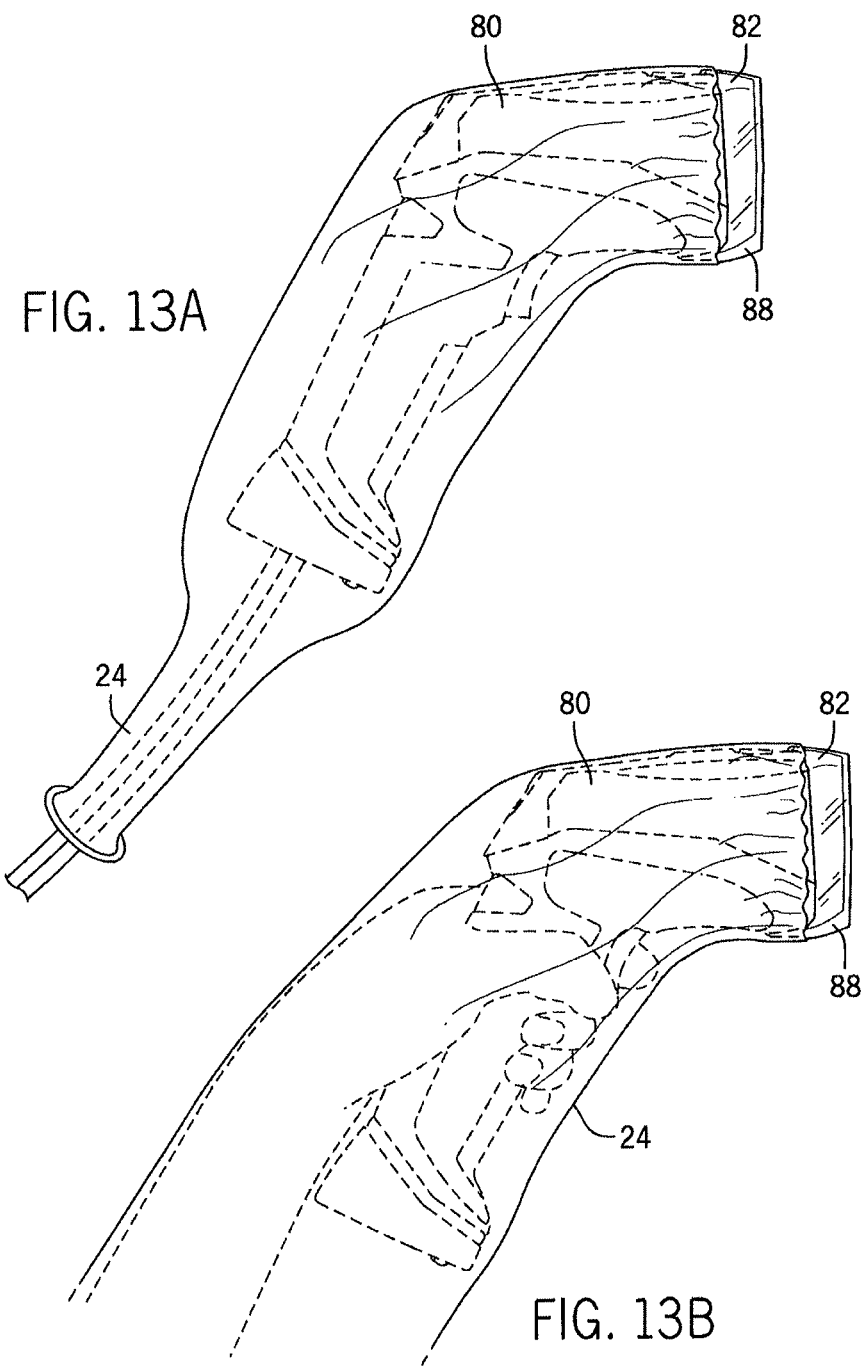
FIG. 13A is a schematic of the handheld reader enclosed within a medical drape.
FIG. 13B is a schematic of the handheld reader and hand of a user enclosed within a medical drape.

FIG. 12 shows an embodiment of handheld reader 80 further comprising base structure 90 built off of handle 84 of the handheld reader that allows the user to place handheld reader 80 on a flat surface and operate handheld reader 80 without holding onto it. FIG. 12 shows transparent sterile lens cover 88 engaged with reader lens 82. In an embodiment, transparent sterile lens cover 88 releasably attaches to reader lens 82 to temporarily fix transparent sterile lens cover 88 in place over reader lens 82 of handheld reader 80. In an embodiment, transparent sterile lens cover 88 snaps into place over reader lens 82 with the application of minor force.

In an embodiment, the handheld reader may be used to scan pre-sterilized components. In an embodiment, the handheld reader may be used to scan pre-packaged component. In an embodiment, the handheld reader is completely wireless. In an embodiment, the handheld reader is battery powered.

In an embodiment, the handheld reader is capable of reading bar codes and has the capability to accept software. In an embodiment, a mobile device, including but not limited to a smartphone can be clipped to the handheld reader. In an embodiment, a handheld reader can be used as a standalone device or the handheld reader can be used to integrate with one or more additional systems and databases, such as hospital systems, manufacture systems, third-party payers, and government agencies.

Table Top-Handheld Reader

Figure 14:
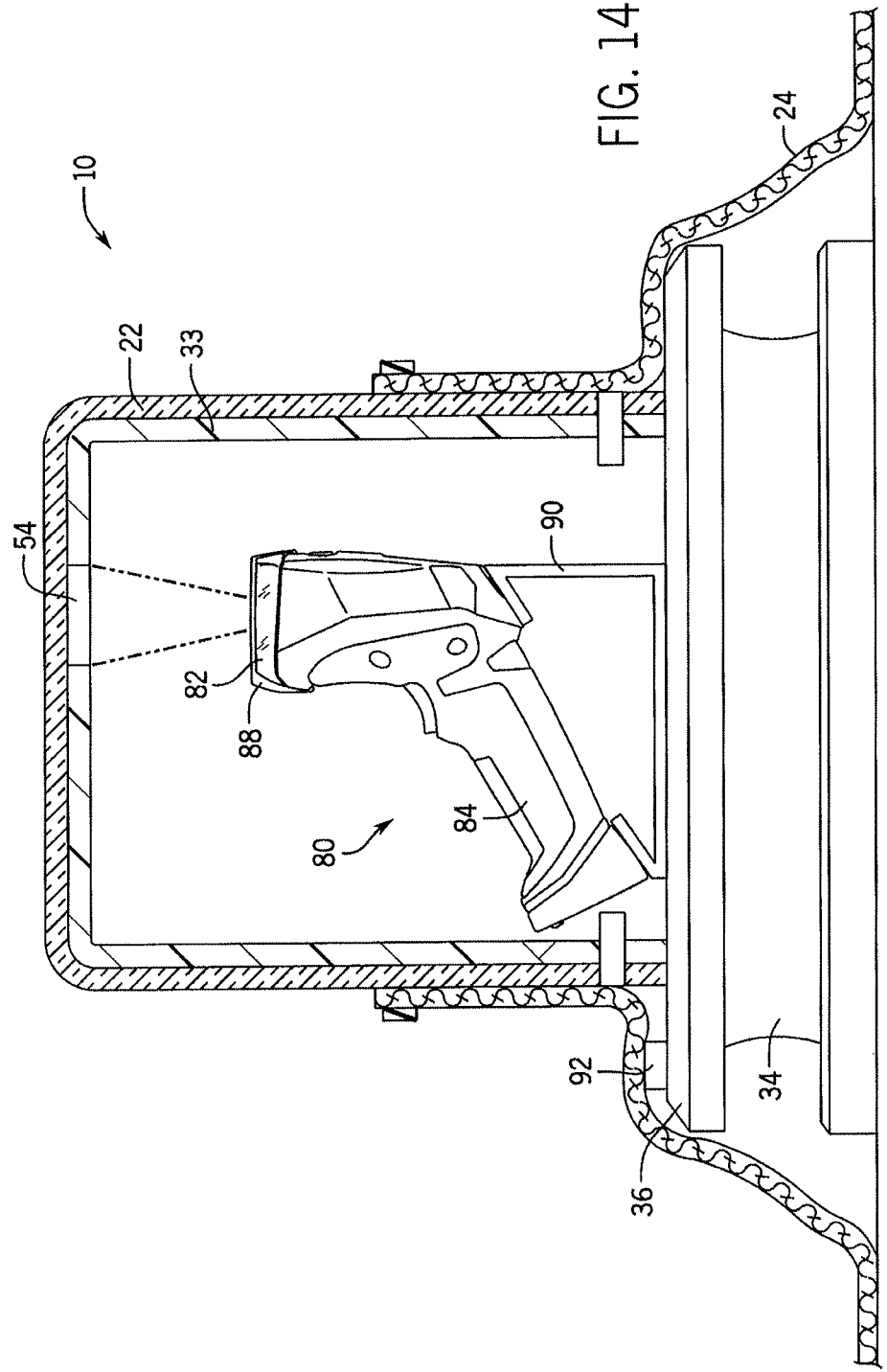
FIG. 14 is a schematic of the reader of FIG. 12 enclosed within the housing structure of the assembly of FIG. 1.

In an embodiment shown in FIG. 14, handheld reader 80 is placed inside housing structure 32 of FIG. 1 by replacing scanner 26 and scanner mounting structure 30. Handheld reader 80 may be positioned in cradle 86 which is secured and/or mounted to base 34. In an embodiment, handheld reader 80 does not contain handle 84. Alternatively, handheld reader 80 may comprise base structure 90 which is mounted to base 34. Reader lens 82 is positioned below aperture 54 which is covered by transparent sterile sheath 22 such that the focal point of handheld reader 80 is on or right above the surface of transparent sterile sheath 22 in the area above aperture 54. As a typical handheld reader is operated by a trigger on handle 84, a scanner switch 92 may be positioned on base 34 outside of cover 33 which allows the user to press to activate handheld reader 80. Alternatively, magnet 64 may be positioned near handheld reader 80 to keep handheld reader 80 activated and continually taking scans when an implant having an identifier is placed on the focal point. The handheld reader 80 may or may not include transparent sterile lens cover 88. Any of the transparent sterile sheath 22, transparent sterile lens cover 88 and reader lens 82 may have magnifying abilities that are compatible with each other.

In an embodiment, the table top-handheld reader is completely wireless. In an embodiment, the table top-handheld reader is battery powered.

In an embodiment, a table top-handheld reader can be used as a standalone device or the table top-handheld reader can be used to integrate with one or more additional systems and databases, such as hospital systems, manufacture systems, third-party payers, and government agencies.

Medical Drape

Assembly 10 further comprises a medical drape. Medical drape 24 may be made of conventional medical drape material. Alternatively, medical drape 24 is transparent and flexible to enable use of a control panel on a reader device. Medical drape 24 may allow for the manipulation of buttons, calibrating dials, and adjusting knobs frequently associated with reader 20.

As shown in FIGS. 1, 2A, and 2B, medical drape 24 temporarily attaches to side wall 76 of transparent sterile sheath 22 and extends out radially to maintain a sterile environment. Medical drape 24 may comprise an elastic band to attach to sheath side wall 76. Alternatively, medical drape 24 may clip onto sheath side wall 76 for attachment. Any attachment mechanism may be used to attach medical drape 24 to sheath side wall 76. In at least some embodiments, medical drape 24 can be permanently adhered to sheath side wall 76 prior to installation on reader 20.

FIGS. 13A and 13B show an embodiment in which medical drape 24 is attached to transparent sterile lens cover 88 of handheld reader 80. Medical drape 24 unrolls from lens cover 88 and creates a barrier between the reader device and the sterile environment. In the situation depicted in FIG. 13A, the user, usually wearing a sterile glove, would generally operate handheld reader 80 by holding reader 80 on top of medical drape 24. Alternatively, as shown in FIG. 13B, the medical drape is designed to fit over the user's hand.

Medical drape 24 may be made of conventional medical drape material, although various other materials can be utilized alone or in combination. Alternatively, medical drape 24 is transparent and flexible to enable use of a control panel on a reader device. Medical drape 24 may allow for the manipulation of buttons, calibrating dials, and adjusting knobs frequently associated with reader 80.

Computer

Assembly 10 comprises computer 25 (not shown) in communication with reader 20. Computer 25 is equipped with software that allows recording and manipulation of input data from reader 20. The software is designed to receive information (manufacturer's information, lot number, serial number, etc.) obtained from the identifier upon being scanned by the reader. The software further allows the user of the computer to input data that indicates where the screw was implanted according to the surgeon's instruction. The location data of where the implant is placed in the patient may be aided by the software, which pulls up an anatomical image where the user of the computer can then just select visually where the implant was inserted. Computer 25 is usually outside the sterile field. Alternatively, the computer may be part of the same assembly as the reader. The term computer is meant to encompass desktop computers, laptops, tablets, pads, and mobile devices, among others, as well as various other computing devices and devices capable of receiving and storing data, whether permanently or transiently.

Additional Components

Assembly 10 may further include additional components such as a keyboard, mouse, stylus, printer, display screen or other interface that allows a user to interact with the system such as to input information, issue commands, power the device on and off, perform file management, upgrade software and database information, monitor output, receive feedback and perform other administrative and non-administrative tasks.

Referring to FIGS. 15-19, an exemplary embodiment of implant tracking assembly 110 is provided that includes various components that are similar in form and/or function to various components described above with respect to implant tracking assembly 10. It shall be understood that various components described below, with like names to those described above, can include one or more of the aforementioned features, such as shapes, dimensions, materials, configuration, uses, etc., as described above.

Figure 15:
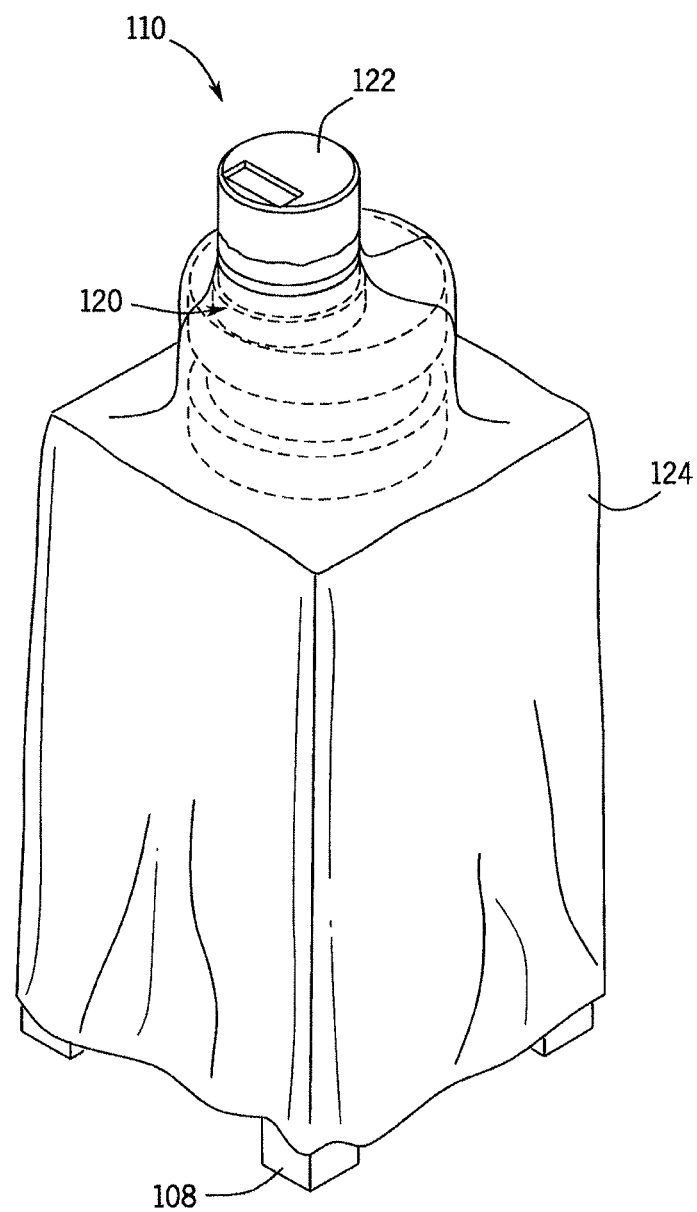
FIG. 15 is a schematic of another embodiment of the implant tracking assembly that includes a reader, a sheath, and a medical drape.
Figure 16:
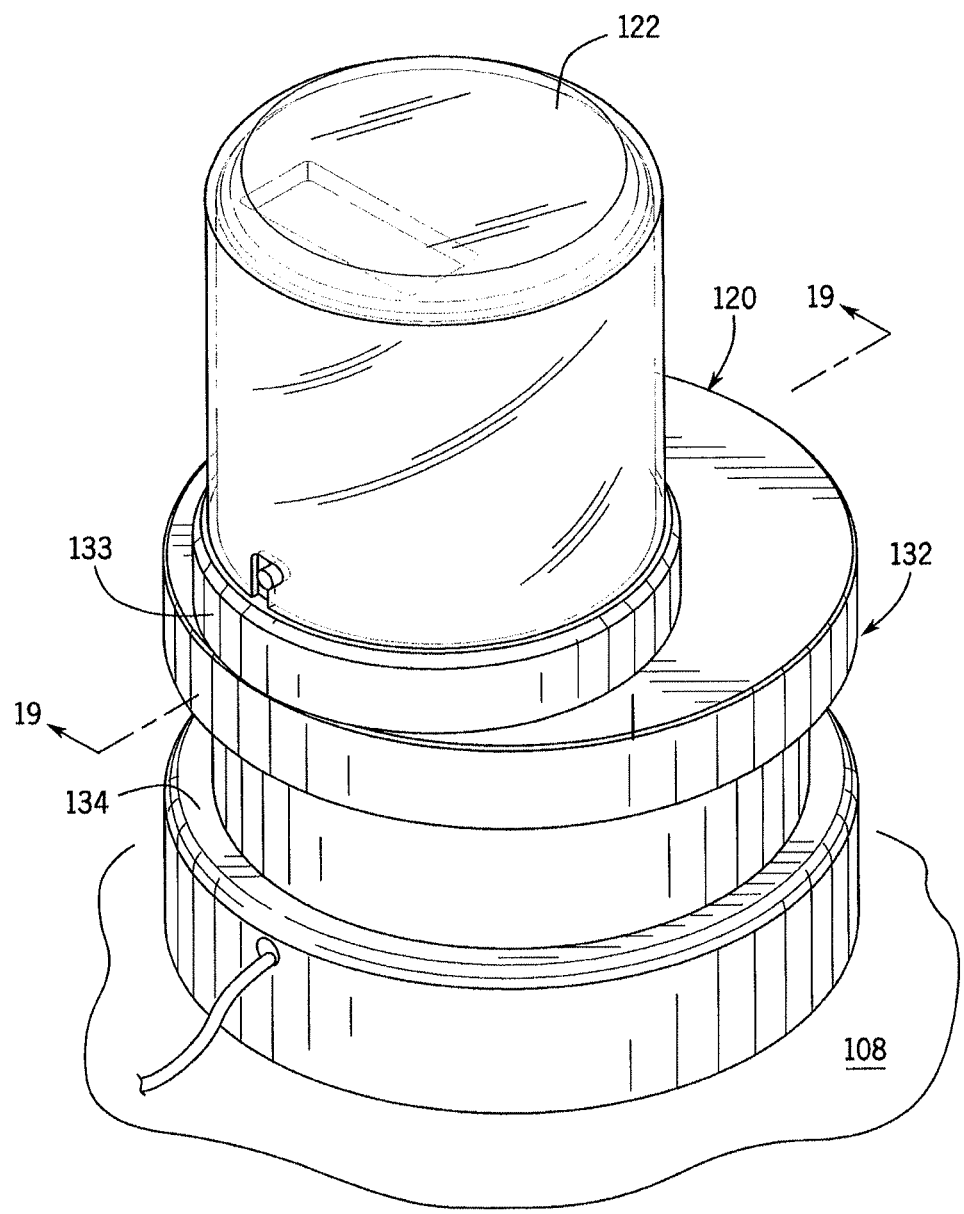
FIG. 16 is a perspective view of the reader and sheath of FIG. 15.
Figure 17:
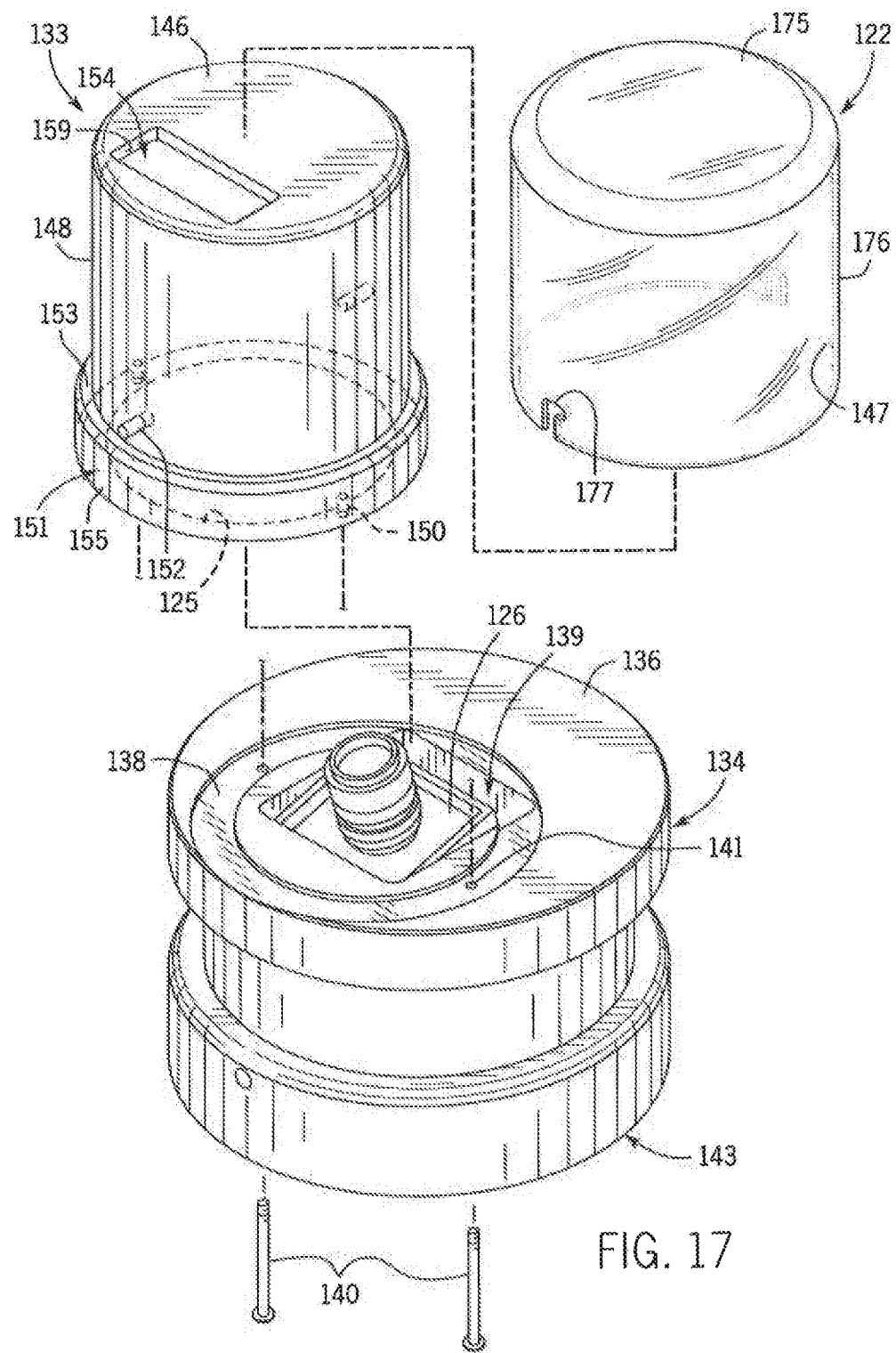
FIG. 17 is an exploded perspective view of FIG. 16.

FIG. 15 provides a perspective view of implant tracking assembly 110 with reader 120, transparent sterile sheath 122, and medical drape 124. FIG. 16 provides a perspective view of reader 120 and transparent sterile sheath 122. Reader 120 includes housing structure 132 having cover 133 and base 134. Referring to FIG. 17, an exploded perspective view of reader 120 and transparent sterile sheath 122 is provided. Base 134 includes base top surface 136 having inset groove 138 formed therein. Inset groove 138 is sized and shaped to fittingly receive planar cover bottom surface 135 of cover 133. Base pin holes 141 are provided, which pass through inset groove 138 to allow vertical pins 140 to pass therethrough and secure to pin holes 150 in cover 133. In this regard, cover 133 can be secured to base 134 without the need for protruding fasteners. In addition, base 134 includes cavity 139, which extends from base top surface 136 towards base bottom 143. Cavity 139 is configured to receive scanner 126, such that at least a portion of scanner 126 is recessed below base top surface 136. In at least some embodiments, cavity 139 forms a rectangular shape sized to accommodate scanner 126, while in other embodiments, cavity 139 is sized and shaped to accommodate various other types, sizes, and shapes of scanners.

As seen in FIG. 17, transparent sterile sheath 122 includes generally circular sheath top surface 175 and cylindrical sheath side wall 176 that extends perpendicularly downward from sheath top surface 175 to sheath bottom surface 147. As discussed above, in at least some embodiments, sheath top surface 75 is slightly convex to deflect ambient light. In addition, transparent sterile sheath 122 includes one or more radial pin slots 177, which are configured to engage one or more radial pins 152 on cover 133 to provide securement of transparent sterile sheath 122 to reader 120. Transparent sterile sheath 122 is sized and shaped to fit over cover 133. More particularly, cover 133 includes generally circular cover top surface 146 and cylindrical side wall 148 that extends substantially perpendicularly downward from cover top surface 146 to flange 151. Flange 151 includes a flange top surface 153, which is configured to receive sheath bottom surface 147 when transparent sterile sheath 122 is installed. Flange side wall 181 extends downward towards base 134 and includes cover bottom surface 135, which is configured to rest on the inset groove 138 when cover 133 is installed on base 134. Although transparent sterile sheath 122 is intended to fit over cover 133, one or both of transparent sterile sheath 122 and cover 133 can vary in shape to provide greater or fewer conforming surfaces.

Cover 133 further includes aperture 154 having an aperture perimeter 159, where aperture 154 allows scanner 126 to obtain information from exemplary object 161 (see FIG. 19) when positioned over the aperture 154. Aperture 154 may be positioned in one of various locations about the cover 133 to provide suitable access to a user and to accommodate the field of view of the scanner 126. In addition, if scanner 126 is configured to sense identifier 111 having a non-optical component (e.g., RFID), then the aperture 154 may be omitted entirely and the cover 133 comprised of a material that allows signal-based communication therethrough, or the cover 133 may include a portion of the cover material that is capable of allowing signal-based communication therethrough.

Figure 18:
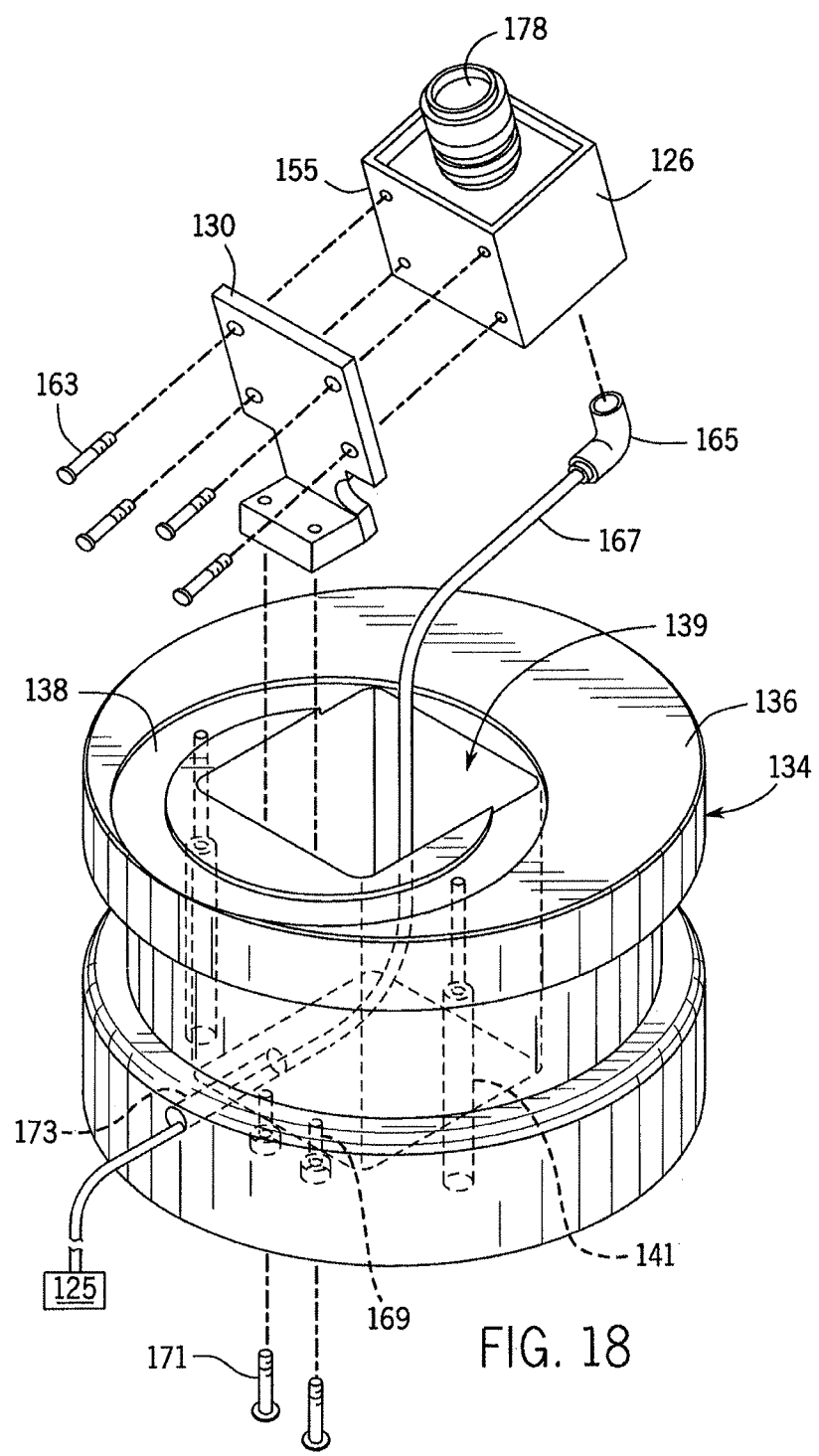
FIG. 18 is an exploded perspective view of various portions of the reader of FIG. 15.

Referring to FIG. 18, an exploded perspective view of reader 120 with cover 133 removed is provided. As shown, scanner 126 includes scanner housing 155 that is secured to scanner mounting structure 130 by one or more scanner fasteners 163. Scanner mounting structure 130 is shaped to provide a suitable angle for scanner 126 to read identifiers 111 through aperture 154. Scanner 126 is connected to plug 165 at one end of cord 167. Plug 165 provides a removable connection between cord 167 and scanner 126. Cord 167 connects scanner 126 to another device, such as computer 125, as discussed above. Base 134 includes mount passages 169 configured to receive mount fasteners 171 that are inserted through mount passages 169 and secured to scanner mounting structure 130. In this manner, scanner 126 can be installed in reader 120 by securing scanner 126 to scanner mounting structure 130, plugging in plug 165, and inserting both into cavity 139 and securing to base 134. Base 134 further includes cord passage 173 that extends from cavity 139 to outside base 134 to provide an outlet for cord 167.

Figure 19:
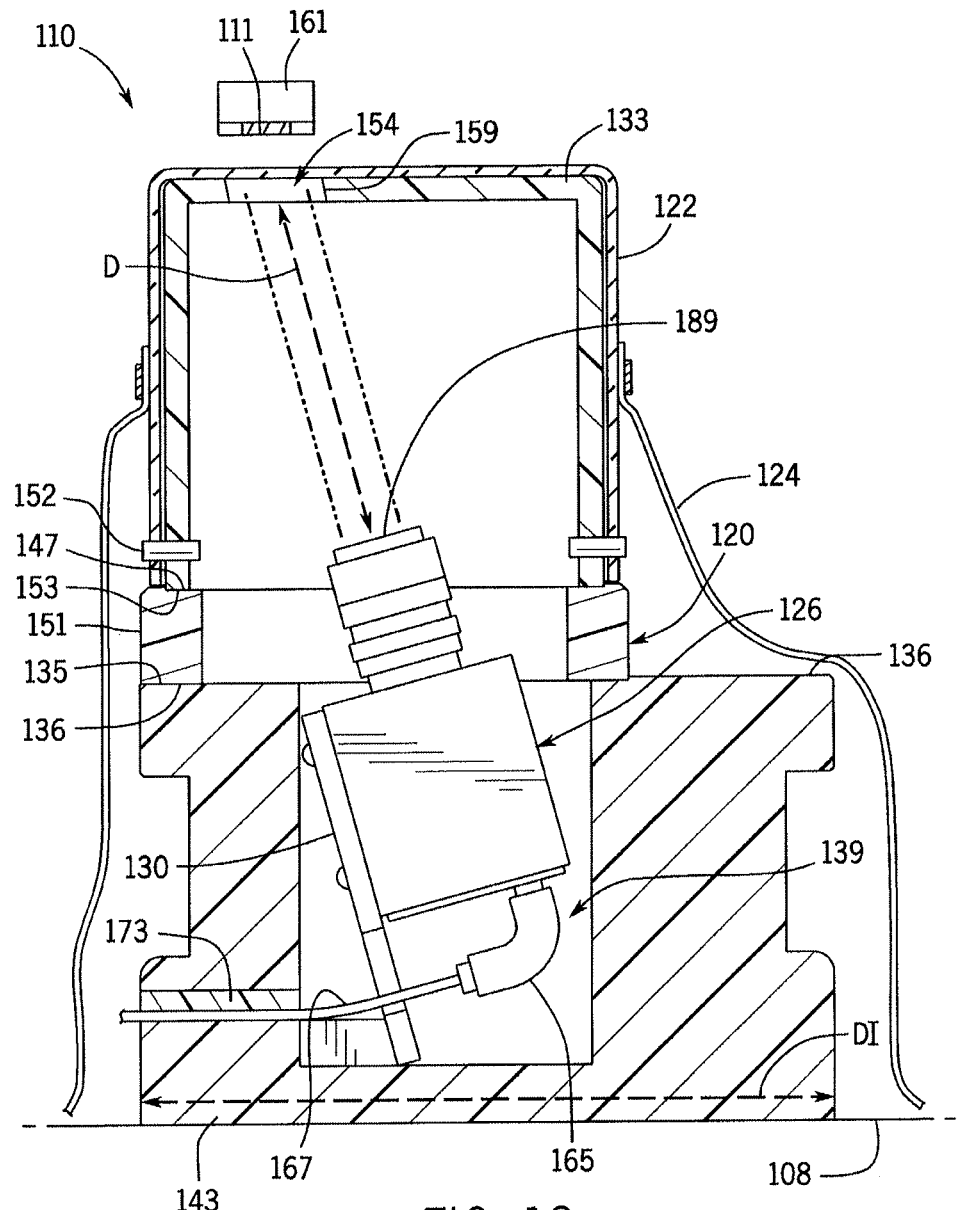
FIG. 19 is a sectional side view taken at line 19-19 of FIG. 16.

Referring to FIG. 19, a sectional side view taken at line 19-19 of FIG. 16 is provided. For illustrative purposes, although medical drape 124 was not shown in FIG. 16, it has been included on FIG. 19. As shown in FIG. 19, scanner 126 includes lens assembly 178 extending from scanner housing 155 and directed towards aperture 154. Lens assembly 178 includes front surface 189, where front surface 189 extends to aperture 154 along a distance D, where distance D is between about 3 inches to about 5 inches. In at least some embodiments, scanner 126 is a Model No. DataMan 500 barcode reader, as manufactured by COGNEX located in Natick, Mass. However, in at least some other embodiments, other models, types, and brands of scanners can be provided. The DataMan 500 model, as well as other types of scanners can be modified from their original manufactured form. For example, the original scanner housing can be reduced in size to fit accordingly in cavity 139, such as by removing portions of the scanner housing without damaging or otherwise rendering other necessary portions or components non-functional. Scanner 126 is configured to read identifier 111, which is located on object 161, such as a medical device, as discussed above. Identifier 111 is communicated to computer 125 for recordation and/or display. It shall be understood that various components described below with like names to those described above, can include similar functions and features, such as shapes, dimensions, materials, configuration, uses, etc., as described above.

Figure 20:
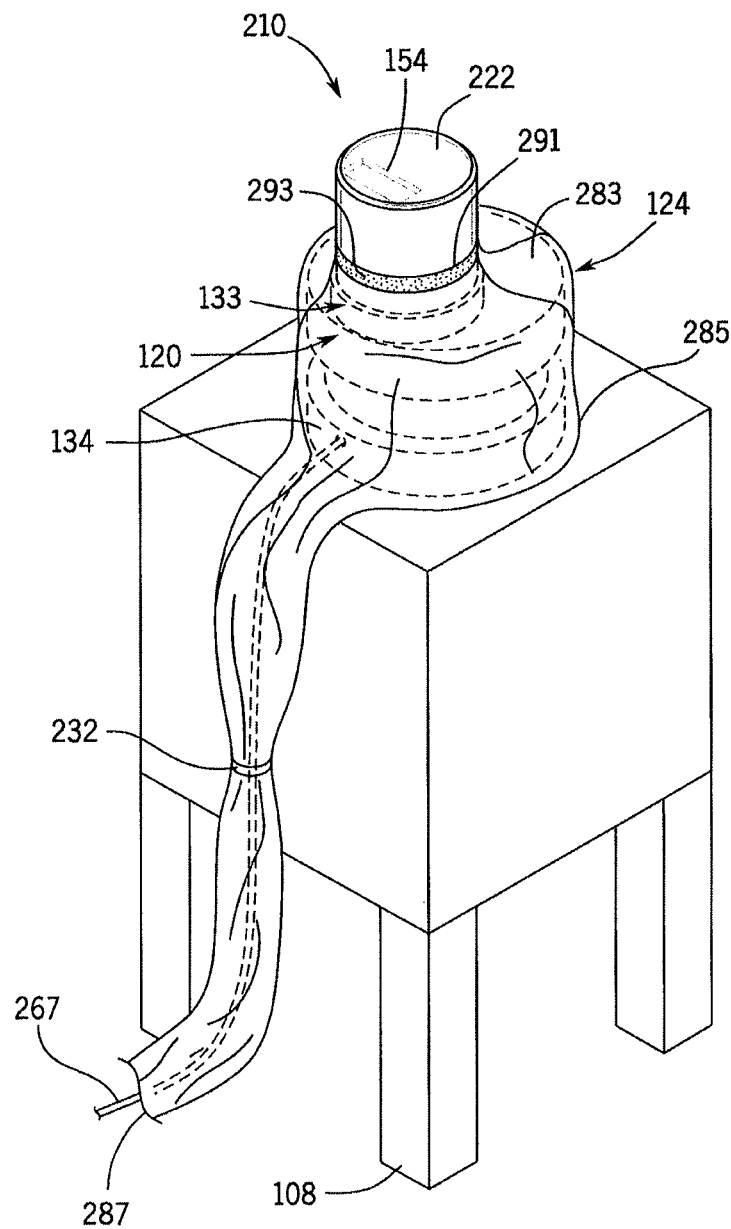
FIG. 20 is a schematic of an embodiment of the implant tracking assembly.

Referring to FIG. 20, implant tracking assembly 210 is illustrated, which includes reader 120 enclosed by sheath 222 and drape 224. As shown, implant tracking assembly 210 is positioned on table 108, which is representative of one of many types of support surfaces that implant tracking assembly 210 can be situated on during a medical procedure. Additionally, in at least some embodiments, sheath 222 is similar or identical to transparent sterile sheath 22 and transparent sterile sheath 122. As shown, drape 224 extends from sheath 222, over reader 120, and over one or more cords 267 connected to reader 120. Drape 224 is secured to sheath 222 in one of a temporary or permanent manner, as discussed further below.

Referring to FIGS. 21 and 22, a perspective and side view of sheath 222 and drape 224 are illustrated. As shown, sheath 222 includes generally circular sheath top surface 275 and cylindrical sheath side wall 276 that extends perpendicularly downward from sheath top surface 275 to sheath bottom surface 247. In at least some embodiments, sheath top surface 275 may be slightly convex to deflect ambient light. In at least some embodiments, sheath 222 includes an interlocking engagement, such as one or more radial pin slots 277, which are configured to engage one or more radial pins 152 on cover 133 to provide securement of sheath 222 to reader 120. In other embodiments, sheath 222 may be positioned over cover 133 without an interlocking engagement.

The sheath 222 is sized and shaped to fit over cover 133, as such, although sheath 222 is illustrated as cylindrical, other shapes, such as rectangular, pyramidal, etc. may be utilized sheath 222 to accommodate various cover 133 shapes. Similar to transparent sterile sheaths 22 and 122, sheath 222 may be transparent, partially transparent or include varied levels of transparency. In addition, sheath 222 can vary in signal-based transparency as well as optical transparency, wherein signal-based transparency allows for transmission of a non-optical scanning signal (not optically dependent) between reader 120 and identifier 111 (FIG. 19) of an object 161, and therefore, may be independent of the level of optical transparency or sheath coloring.

As discussed above, cover 133 includes aperture 154 having an aperture perimeter 159, wherein aperture 154 allows scanner 126 to obtain information from object 161 (see FIG. 19) when positioned over aperture 154. As sheath 222 covers cover 133, the scan will also pass through sheath 222. To accommodate scanning therethrough, sheath 222 is comprised of a material that is completely or at least partially optically transparent or signal-based transparent. For example, sheath 222 may be substantially opaque, but include a window (not shown) that is positionable over at least aperture 154 to allow scanner 126 to view or otherwise communicated with identifier 111 of object 161.

Referring to FIGS. 21 and 22, sheath 222 is shown with drape 224. The drape 224 includes drape upper portion 283 and drape lower portion 285, where the drape upper portion 283 includes a first end 291 of drape 224 and drape lower portion 285 includes a second end 287 of the drape 224. The drape 224 is secured to and extends radially from sheath side wall 276 to enclose reader 120, and various related components, such as electrical cords and control panels, among other things.

As shown, first end 291 of drape 224 is secured to sheath side wall 276 along securement band 293, which encircles sheath side wall 276. The securement can be one of temporary or permanent and in at least some embodiments, provides an airtight seal. In a temporary configuration, drape 224 may be held to sheath 222 by a fastener, such as a rubber band or clip. Any attachment mechanism may be used to attach drape 224 to sheath side wall 276, although in the present embodiment, first end 291 is permanently secured to sheath 222. A permanent securement may be performed in one of various manners, such as heat welding, heat sealing, chemical adhesives, etc. Drape 224 may be comprised of conventional medical drape material or another suitable material, such as vinyl, that is sterilizable and able to provide a sufficient sterile barrier to limit or prevent contamination between reader 120 and the surrounding environment. Drape 224 may be configured with one or more of various levels of transparency, and may be flexible enough to enable use of a control panel on reader 120. More particularly, drape 224 may include sufficient flexibility to allow for the manipulation of buttons, calibrating dials, and adjusting knobs that may be associated with reader 120.

FIGS. 21 and 22 provide an embodiment of drape 224 that includes a generally pyramidal-shaped drape upper portion 283, which extends from sheath side wall 276 to the drape lower portion 285. The drape lower portion 285 then extends in a linear manner (i.e., parallel sidewalls) along drape sides 294. FIGS. 23 and 24 provide an embodiment of drape 224 that includes a generally conical-shaped drape upper portion 283 that extends from sheath side wall 276 to the drape lower portion 285. The drape lower portion 285 then extends in a cylindrical manner (i.e., parallel sidewalls) along drape sides 294. Although drape lower portion 285 is shown and described as extending linearly and cylindrically, drape lower portion 285 may extend in other manners with varied sizes and shapes, and may include a closure (not shown), such as a drawstring, elastic band, etc. at the second end 287.

As shown in FIG. 20, drape lower portion 285 extends over reader 120 and a length of cord(s) 267. In this manner, drape 224 can provide a sterile barrier that extends for several feet, for example six feet, to allow reader 120 to be situated adjacent to a patient during an implant procedure. In at least some embodiments, drape 224 may extend to cover additional components connected to reader 120. Fasteners, such as tie strap 299, can be used to secure the drape lower portion 285, which can substantially limit or prevent air exchange between reader 120 and environmental air outside sheath 222 and drape 224, as shown in FIG. 20. The extended drape lower portion 285 allows for positioning of reader 120 adjacent to the patient, which allows an assistant to scan objects 161 (i.e., implants) and pass them directly to a surgeon for implantation as quickly and efficiently as possible, and without leaving the near proximity of the surgeon.

Referring to FIGS. 25 and 26, FIG. 25 illustrates a perspective view of sheath 222 and medical drape 224 of FIG. 20, in a rolled configuration, and FIG. 26 illustrates a sectional side view taken at line 25-25 of FIG. 25. Prior to installation of sheath 222 and drape 224, drape 224 is situated in a folded configuration, such as a telescopic fold, to facilitate convenient and efficient installation of over reader 120 and cord(s) 267. To install sheath 222 and drape 224, the user places the sheath 222 and the folded drape 224 over reader 120 to position the sheath 222 onto cover 133. The sheath 222 is interlocked with cover 133 and the drape 224 is then unfolded over the reader 120 and the cord(s) 267. In FIG. 25, drape 224 is shown in a folded configuration having circular shape. Depending on the shape of the drape 224, particularly, the drape lower portion 285, the drape 224 may have a non-circular or partially circular shape when folded, such as in a square configuration.

Referring to FIGS. 27A-30D, exemplary embodiments of readers with sterile sheaths for the implant tracking assembly in accordance with any of the embodiments described above (e.g., implant tracking assembly 10, 110, 210) is provided that includes various components that are similar in form and/or function to various components described above with respect to implant tracking assemblies 10, 110, 210, as well as readers 20, 120, 220 and sterile sheaths 22, 122, 222. It shall be understood that various components described below, with like names and/or reference numbers to those described above, can include one or more of the aforementioned features, such as shapes, dimensions, materials, configuration, uses, etc., as described above.

Figure 27A:
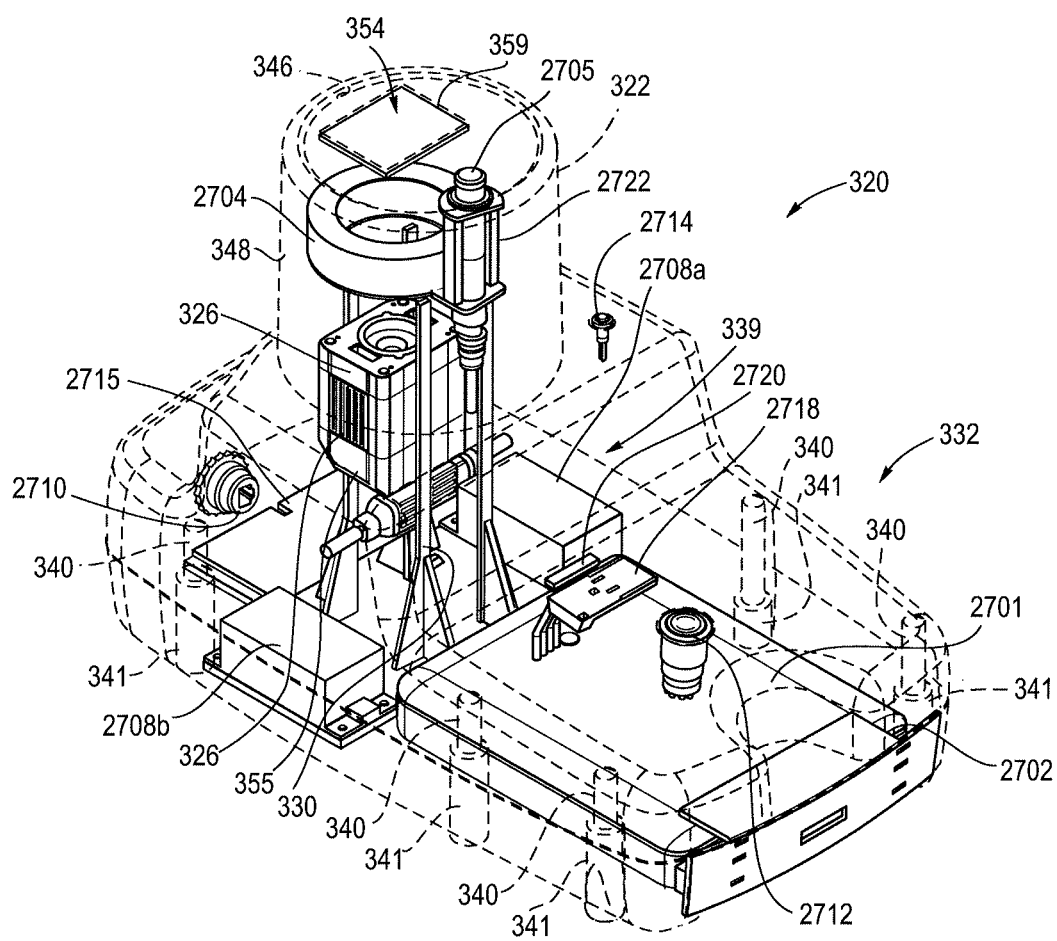
FIG. 27A is a schematic of another embodiment of a reader for the implant tracking assembly with the housing shown as transparent.
Figure 27B:
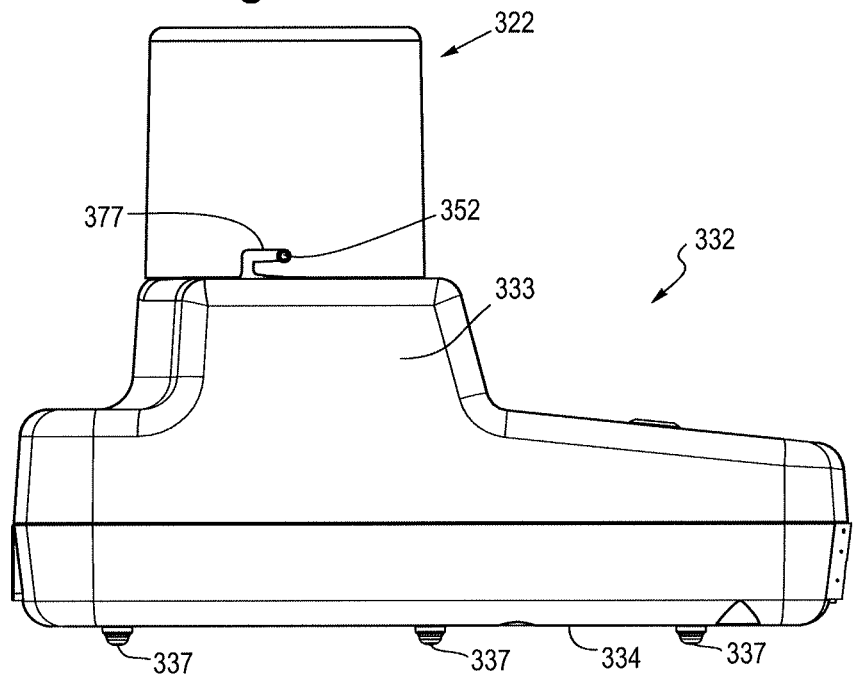
FIG. 27B is a side view of the reader of FIG. 27A.
Figure 27C:
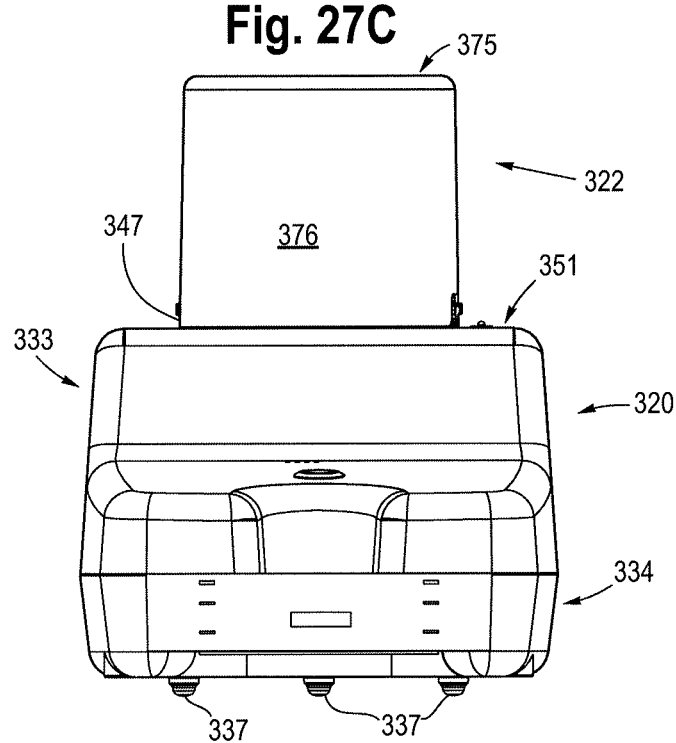
FIG. 27C is a front view of the reader of FIG. 27A.
Figure 28A:
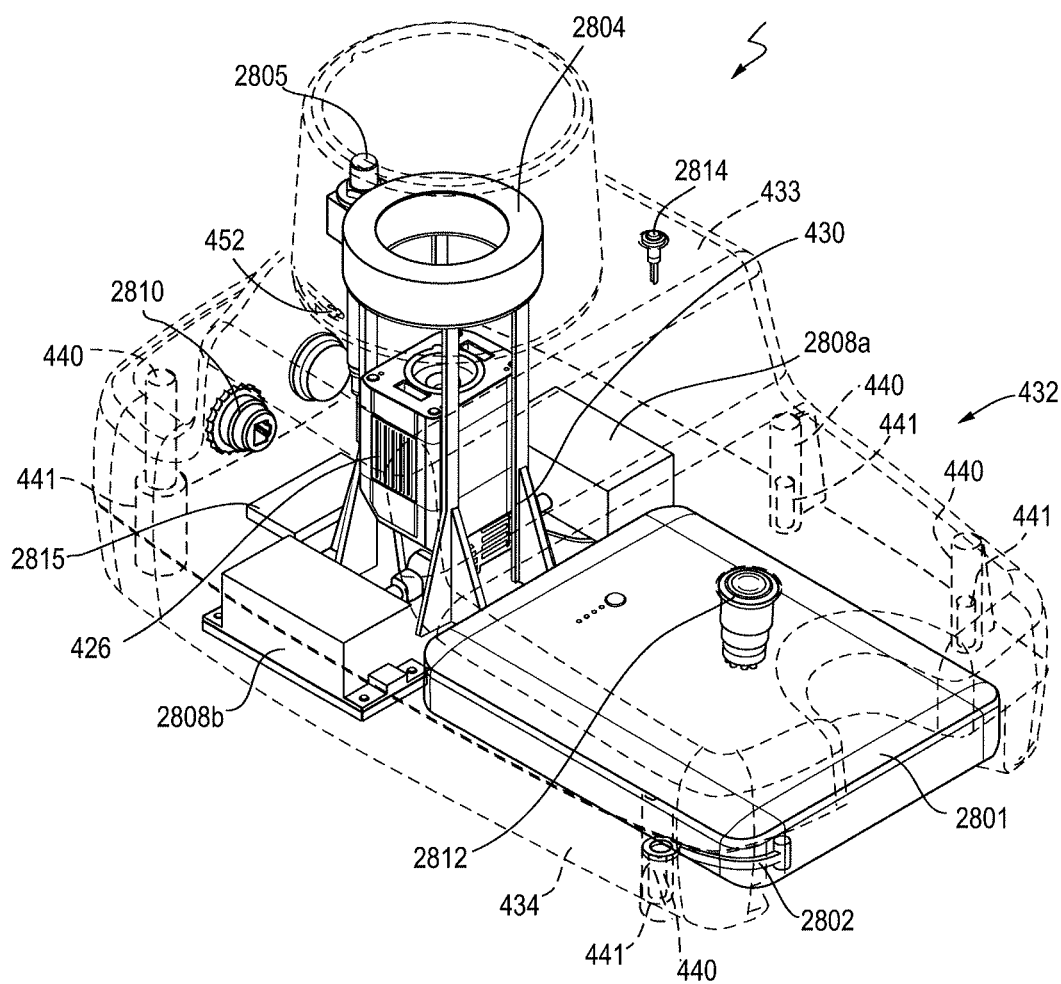
FIG. 28A is a schematic of another embodiment of a reader similar to the embodiment shown in FIG. 27A-27C with the housing shown as transparent.

FIG. 27A provides a perspective view of a further embodiment of a reader 320 with a sterile sheath 322 for use with an implant tracking assembly 310 (not shown) which may further include a medical drape 324 (not shown). FIGS. 27B and 27C provide side and front views of the reader 320 with sheath 322, respectively The medical drape 324 may be as discussed with reference to any of the medical drapes 24, 124, 224 described earlier herein. FIGS. 27B and 27C provide side and front views of the reader 320 with sheath 322, respectively.

Reader 320 includes housing structure 332 which is shown in FIG. 27A as transparent for the purpose of illustrating the internal components. The housing structures 332 includes a cover 333 and base 334. Base pin holes 341 are provided to allow vertical pins 340 to pass therethrough and secure cover 333 to base 334 without the need for protruding fasteners. Base 334 and cover 333 together define cavity 339, which accommodates and houses the interior components of the reader 320.

Transparent sterile sheath 322 includes generally circular sheath top surface 375 and cylindrical sheath side wall 376 that extends perpendicularly downward from sheath top surface 375 to sheath bottom surface 347. As discussed above, in at least some embodiments, sheath top surface 375 is slightly convex to deflect ambient light. In addition, transparent sterile sheath 322 includes one or more radial pin slots 377, which are configured to engage one or more radial pins 352 on cover 333 to provide securement of transparent sterile sheath 322 to reader 320. Transparent sterile sheath 322 is sized and shaped to fit over cover 333. As such, although sheath 322 is illustrated as cylindrical, other shapes, such as rectangular, pyramidal, etc. may be utilized to accommodate the particular geometries of the cover 333.

More particularly, cover 333 includes generally circular cover top surface 346 and cylindrical side wall 348 that extends substantially perpendicularly downward from cover top surface 346 to generally planar upper surface 351 of cover 333. Although transparent sterile sheath 322 is intended to fit over cover 333, one or both of transparent sterile sheath 322 and cover 333 can vary in shape to provide greater or fewer conforming surfaces.

Further, sheath 322 can vary in signal-based transparency, as well as optical transparency, as described, for example, with reference to sheath 222.

Cover 333 further includes aperture 354 having an aperture perimeter 359, where aperture 354 allows scanner 326 to obtain information from exemplary object 361 (such as, for example, shown with the embodiment discussed with reference to FIG. 19) when positioned over the aperture 354. Aperture 354 may be positioned in one of various locations about the cover 333 to provide suitable access to a user and to accommodate the field of view of the scanner 326. In addition, if scanner 326 is configured to sense identifier 311 (not shown) having a non-optical component (e.g., MID), then the aperture 354 may be omitted entirely and the cover 333 comprised of a material that allows signal-based communication therethrough, or the cover 333 may include a portion of the cover material that is capable of allowing signal-based communication therethrough.

Scanner 326 includes scanner housing 355 that is secured to scanner mounting structure 330. Scanner mounting structure 330 is configured to provide a suitable angle for scanner 326 to read identifiers 311 (not shown) through aperture 354. In at least some embodiments, scanner 326 is a Model No. DataMan 300 reader, as manufactured by COGNEX located in Natick, Mass. However, in at least some other embodiments, other models, types, and brands of scanners can be provided. The DataMan 300 model, as well as other types of scanners can be modified from their original manufactured form. For example, the original scanner housing can be reduced in size to fit accordingly in cavity 339, such as by removing portions of the scanner housing without damaging or otherwise rendering other necessary portions or components non-functional.

As shown in FIGS. 27B-27C, the housing structure 332 further includes protective rubber feet 337 on the bottom surface 331 of the base 334 of the housing structure 332.

As mentioned above, the cavity 339 houses the internal components of the reader 320. Battery pack 2701 is located toward the front of the reader 320 and accessible via batter door 2702. As shown, the battery pack 2701 is self-contained and removable from the reader 320. In an embodiment, the battery pack 2701 is configured with one or more batteries (not shown) capable of running the scanner 326 for at least 24 continuous hours. The one or more batteries may be single-use or rechargeable using conventional recharging methods/devices and/or a separate proprietary or specially-designed charging station. In still further embodiments, the battery pack may be charged while remaining in the reader 320.

In the embodiment shown, the reader 320 also includes two AC/DC converters 2708a, 2708b so that the reader 320 may be used without the battery pack 2701, when the batteries are dead, or when it is anticipated that the batteries may not last for the duration during which the reader 320 is needed. In the embodiment shown, AC/DC converter 2708a is a 24V out, 15 W converter and AC/DC converter 2708b is a 5V out, 15 W converter. Specifically, in an embodiment the 24V out AC/DC converter is an EML15US05-5 AC-DC converter and the 5V out AC/DC converter is an EML15US24-S AC/DC converter, both of which are manufactured by XP Power, with a headquarters located in Singapore. However, in at least some other embodiments, other models, types, and brands of AC/DC converters can be provided, including AC/DC converters with different outputs depending on the use of the reader 320. In an embodiment, a single power converter can be used. In another embodiment, a power converter may not be used. One of skill in the art will understand that a power converter regulates power to various components at the proper voltage and ampage.

The cavity 339 also houses the light ring 2704 which is positioned over the scanner 360 and concentric with the lens of the scanner 360 so as to provide light through the aperture 354. In the embodiment shown, the light ring 2704 is activated by the presence of an object over the electronic proximity sensor (e.g., photoeye) 2705; however, in further embodiments, the light ring 2704 may be on anytime the scanner 326 is active or powered on, or anytime the reader 320 is powered on. In an embodiment, the proximity sensor 2705 serves to activate the scanner 360. In the embodiment, the proximity sensor 2705 is secured within the cover 333, and specifically within the cylindrical side walls 348 of the cover 333, using a mounting bracket 2722.

Power button 2712 is shown protruding from the upper surface of the cover 333. The power button 2712 turns the reader 320 and/or scanner 326 on and off. In the embodiment shown, the power button 2712 is a continuous off momentary on SPST switch, such as those manufactured by E-SWITCH located in Minneapolis, Minn. However, in at least some other embodiments, other models, types, and brands of switches can be provided.

Also shown visible through the top surface of the cover 333 is power status indicator 2714, which in the embodiment shown is an LED, and specifically a Dialight 559 Series Snap-In LED Indicator, manufactured by Dialight with a headquarters located in Suffolk, England. However, in at least some other embodiments, other models, types, and brands of LEDs, and, generally, power status indicators, may be used.

The cavity 339 also houses the processor board 2715 which controls the activity of the scanner 360, ring light 2704, proximity sensor 2705, power allocation and/or other activities and functions of the reader 320. In the embodiment shown, the processor board 2715 a XMEGA-A3BU Xplained board as manufactured by Atmel, headquartered in San Jose, Calif. However, in at least some other embodiments, other models, types, and brands of processor boards can be provided.

In the embodiment shown, a Bluetooth board 2718 is also contained within the cavity 339. Depending on the use of the reader 320, the Bluetooth board 2718 may be configured to connect with legacy devices, such as, for example, those that support only Bluetooth SPP or Apple iAP2 profiles, and/or devices which support Bluetooth Smart. For example, in the embodiment shown, the Bluetooth board 2718 is a BT121 Bluetooth Smart Ready Module capable of supporting Bluetooth SSP, Apple iAP2 and Bluetooth Smart devices, manufactured by Silicon Labs located in Austin, Tex.

The reader 320 may also include a number of inputs to communicate power and/or information to the reader 320. For example, in the embodiment shown, a pass-through CAT5e connection port 2710 is provided on the rear of the housing structure 332. Specifically, in the CAT5e connection port 2710 is an RJ45, 8-pole metal CAT5e port, such as, for example, manufactured by MURR Electronik, headquartered in Germany. However, in at least some other embodiments, other models, types, and brands of CAT5e ports can be provided. Further, in some embodiments, different Ethernet cables may be used with the reader 320, and therefore different ports may be provided on the housing structure 332.

The reader 320 may also include a power connector, such as a socket for a plug. In the embodiment described with reference to FIGS. 27A-27C, for example, the reader 320 includes a 110 V 2 prong socket (not shown), such as a 38330-XX02, manufactured by Molex, located in Delaware. However, in at least some other embodiments, other models, types, and brands of sockets can be provided.

In some embodiments, the reader 320 may further include a battery power level indicator (e.g., colored light indicator(s), percentage display, etc.) or other reader 320 status indicator, such as light pipe 2720. Light pipe 2720 is connected at a first end to one or more LEDs (such as, for example, associated with the battery pack 2701, processor board 2715, Bluetooth board 2718, scanner 326 and/or other components of the reader), and the light pipe 2720 transmits the emitted light to a portion of the housing structure 332 at which the light may be visible. For example, light pipe 2720 may be configured to communicate the status of the reader 320, generally, such as the power status, the status of the scanner 326 (e.g., ready, scanning, etc.), the status of any Bluetooth or wireless connectivity, whether any power supply (other than the internal battery) is connected to the scanner 320 and/or whether the scanner 326 or reader 320 are experiencing an error. The reader 320 may also include other components to make the reader 320 easier to use and/or any problems with the reader 320 easier to diagnose.

FIGS. 28A-28D show an embodiment of a reader 420 similar to reader 320, but with the sterile sheath 422 removed and some variation in the internal components. It shall be understood that various components described below with reference to FIGS. 28A-28D having like names and/or reference numbers to those described above, can include similar functions and features, such as shapes, dimensions, materials, configuration, uses, etc., as described above.

Specifically, reader 420 does not include a Bluetooth board, light pipe or battery door. In place of battery door, the reader 420 includes a battery lock 2802 to hold the battery pack 2801 in place. Further, the specific arrangement of the scanner 426, scanner mounting structure 430, and proximity sensor 2805 is changed in reader 420 relative to reader 320, although the functionality of those components is the same.

The remaining elements and components of reader 420 are in accordance with any of the embodiments described above with reference to implant tracking assemblies 10, 110, 210, 310, with various components that are similar in form and/or function to the various components described above with respect to implant tracking assemblies 10, 110, 210, 310, as well as readers 20, 120, 220, 320 and sterile sheaths 22, 122, 222, 322, described with like terminology and reference numbers. It shall be understood that various components described below, with like names and/or reference numbers to those described above, can include one or more of the aforementioned features, such as shapes, dimensions, materials, configuration, uses, etc., as described above.

Figure 29A:
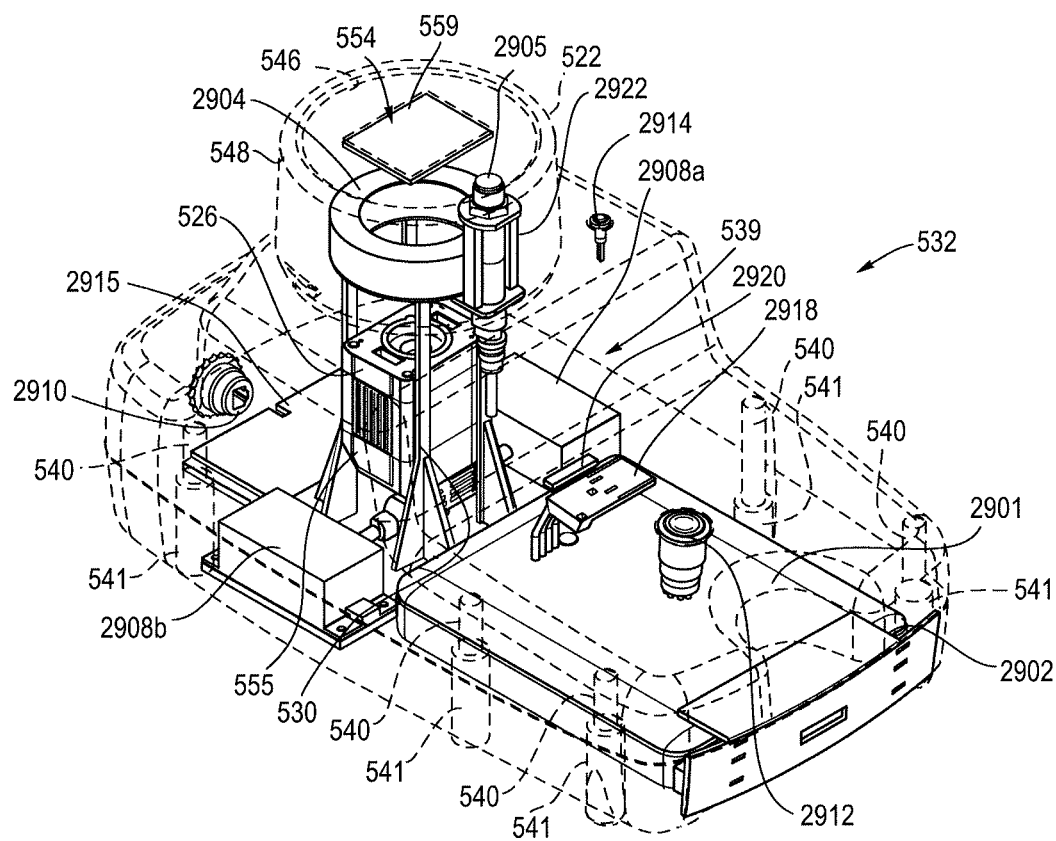
FIG. 29A is a schematic of another embodiment of a reader for the implant tracking assembly with the housing shown as transparent.
Figure 29B:
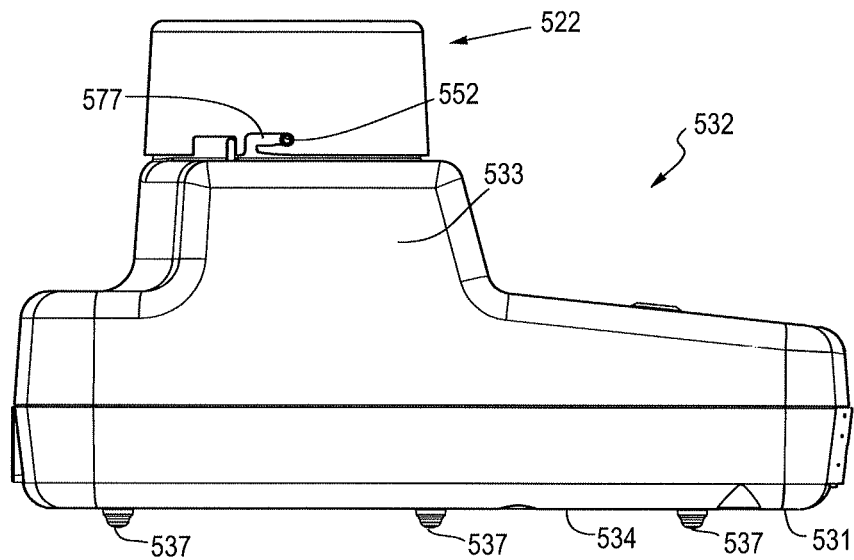
FIG. 29B is a side view of the reader of FIG. 29A.
Figure 29C:
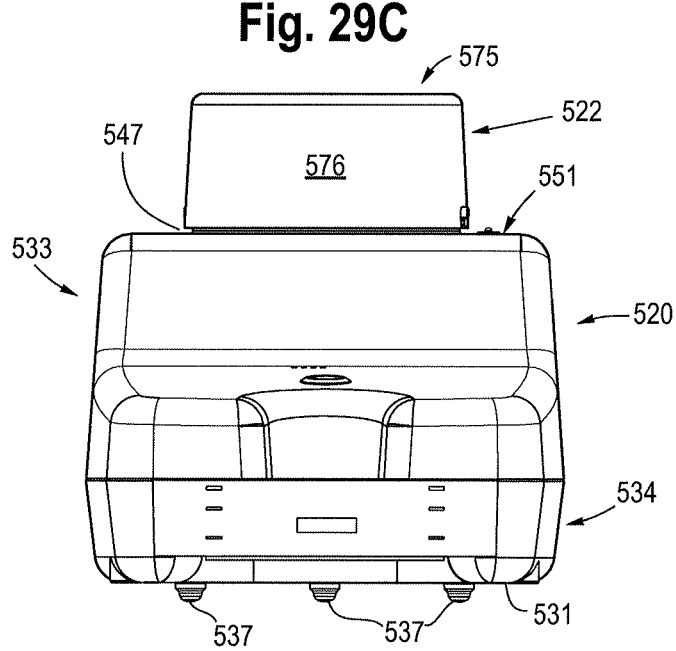
FIG. 29C is a front view of the reader of FIG. 29A.
Figure 30A:
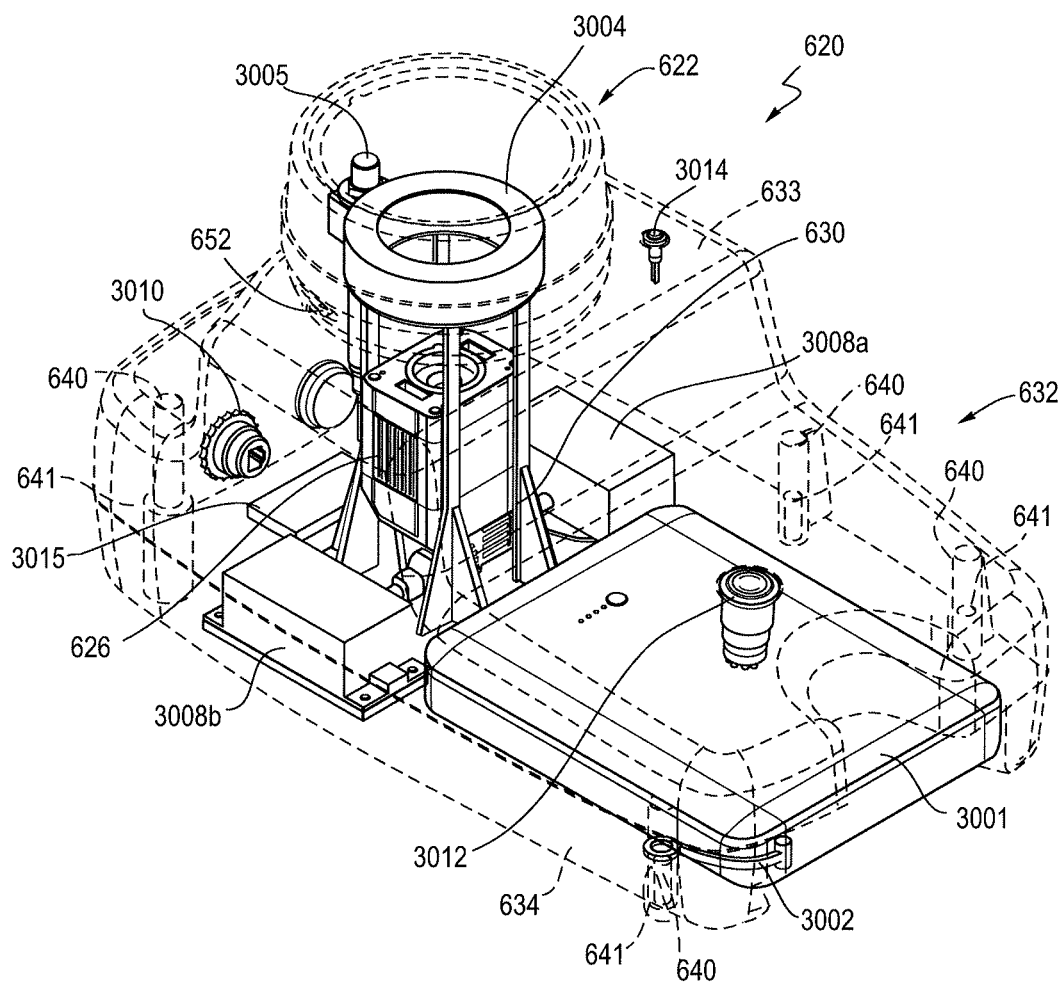
FIG. 30A is a schematic of another embodiment of a reader similar to the embodiment shown in FIG. 29A-29C with the housing shown as transparent.

It shall be understood that various components described below with reference to FIGS. 29A-29C having like names and/or reference numbers to those described above, can include similar functions and features, such as shapes, dimensions, materials, configuration, uses, etc., as described above. FIGS. 29A-29C show an embodiment of a reader 520 similar to reader 320, but having a shortened sterile sheath 522 and corresponding cover cylindrical side wall 548. The remaining structures and components are identical or similar in structure and/or function to those identified with like numbers with reference to reader 320, above.

It shall be understood that various components described below with reference to FIGS. 30A-30D having like names and/or reference numbers to those described above, can include similar functions and features, such as shapes, dimensions, materials, configuration, uses, etc., as described above. FIGS. 30A-30D show an embodiment of a reader 620 similar to reader 520 with some variation in the internal components. Specifically, reader 620 does not include a Bluetooth board, light pipe or battery door. In place of battery door, the reader 620 includes a battery lock 3002 to hold the battery pack 3001 in place. Further, the specific arrangement of the scanner 626, scanner mounting structure 630, and proximity sensor 3005 is changed in reader 620 relative to reader 520, although the functionality of those components is the same. Reader 620 also includes a securement band 693, such as described with reference to reader 220 above.

The remaining elements and components of reader 620 are in accordance with any of the embodiments described above with reference to implant tracking assemblies 10, 110, 210, 310, 410, 510 with various components that are similar in form and/or function to the various components described above with respect to implant tracking assemblies 10, 110, 210, 310, 410, 510 as well as readers 20, 120, 220, 320, 420, 520 and sterile sheaths 22, 122, 222, 322, 422, 522, described with like terminology and reference numbers. It shall be understood that various components described below, with like names and/or reference numbers to those described above, can include one or more of the aforementioned features, such as shapes, dimensions, materials, configuration, uses, etc., as described above.

While the embodiments shown in FIGS. 27A-30D are shown as table top readers, one skilled in the art will readily appreciate that the internal components of the readers may be repositioned and/or reconfigured in order to accommodate a housing structure which is a handheld reader or a table top-hand held reader, as described with reference to FIGS. 11-14 above.

It shall be understood that a reader as described herein may comprise one embodiment or any combination of two or more embodiments as described herein. Moreover, the medical drapes described herein may comprise one embodiment or any combination of two or more embodiments described herein, and the readers described herein may be used with any embodiment or combination of two or more embodiments of the medical drapes described herein.

As one skilled in the art would understand, a medical device of the present disclosure includes implants, such as artificial joints, spinal implants, active medical device implants such as cardiac defibrillators, cardiac pacemakers, gastrointestinal pace makers, and arterial stents, as well as other passive or active implantable medical devices, and other tools and devices used during medical procedures (e.g., operations, surgeries, etc.). In addition to implants, tracking assembly 10, 110, 210, 310, 410, 510, 610 can be utilized to scan other medical devices and/or instruments that may be used during surgery, such as a clamp, a scalpel, etc. As used herein, one skilled in the art will therefore understand the term "medical devices" to be inclusive of medical implants and medical tools, as well as ancillary tools which may be used during a medical procedure and which may contain an identifier (e.g., sponges, rags, towels, etc.).

Implant Tracking Method

The present disclosure provides a method of tracking a medical device including providing a reader as described above, placing a transparent sterile sheath over the housing structure of the reader device, placing a medical device having an identifier on the top surface of the transparent sterile sheath above the aperture of the housing structure, and scanning the identifier of the medical device to record the stored data.

An advantage of the present disclosure is a method of tracking an implant that allows for greater efficiency and ease of use by the operator, while maintaining a sterile environment. By using the implant tracking method of the present disclosure, the user does not have to hand record the implant identifying information, which allows a faster operating procedure. Nor does the user need to spend time finding the focal point of the scanner to obtain an accurate read of the identifier. The method of the present disclosure is designed to allow a user to place the implant with the identifier onto its top surface to obtain an accurate scan of the identifier and then quickly pass the implant to the surgeon for implantation, all while not compromising the sterility of the implant or surgical field. The scanner takes a scan automatically when the identifier is placed on the top surface of the transparent sheath above the aperture. Thus, the user does not have to bother with a button to activate the scanner to take a scan while handling in the implant.

In an embodiment, the identifier is a conventional 4×4 millimeter (mm) matrix, or a non-conventional 2×2 mm, or 1.4×1.4 mm matrix laser etched directly onto the implant device, although any data matrix, barcode, QR code or any other code technology may be used as identifiers. The identifier may also be a radio frequency identification tag (RFID) that is readable through radio frequency transmission generated by an independently powered RFID device, including, for example, an MID tag that includes a transponder and is readable in response to a radio frequency signal transmitted to the RFID device. In some embodiments, the identifier is a human readable visual and/or tactile graphic such as alphanumeric characters that can be manually recorded in a database or chart. By having the identifier etched, printed or otherwise formed directly in or on the surface of the medical device, the user does not have to bother with scanning external tags to the medical device and removing the tag prior to the implant procedure, thus allowing for a more efficient method of tracking.

The method further includes positioning a medical drape to cover the remaining portions of a reader device. In an embodiment, the positioning of the medical drape to cover the remaining portions of a reader device includes unrolling the medical drape from the transparent lens cover to extend around the remaining portions of the reader device. In an embodiment, the positioning of the medical drape to cover the remaining portions of a reader device further includes unrolling the medical drape to extend around the remaining portions of the reader as well as the user's arm operating the reader device.

In an embodiment, a method and system for tracking a medical device is provided. In an embodiment, the method includes creating a patient profile, creating an operating profile comprising at least one surgical site, providing a tracking assembly comprising a reader, placing a medical device having an identifier over the reader, scanning the identifier of the medical device to electronically record the medical device data, and associating the scanned medical device data with the at least one surgical site.

In another embodiment, the present disclosure provides a method and system of tracking a medical device wherein the step of providing a reader is as described above and further includes placing a transparent sterile sheath over the housing structure of the reader device.

As will be understood by one skilled in the art, the step of creating an operating zone profile for a patient may occur prior to a surgery or otherwise before providing a reader, simultaneously with any of the steps of providing a reader, placing a medical device having an identifier on the top surface of the transparent sterile sheath above the aperture of the housing structure and scanning the identifier of the medical device to record the data, and/or at any time before associating the scanned data with the operating zone profile.

Figure 31:
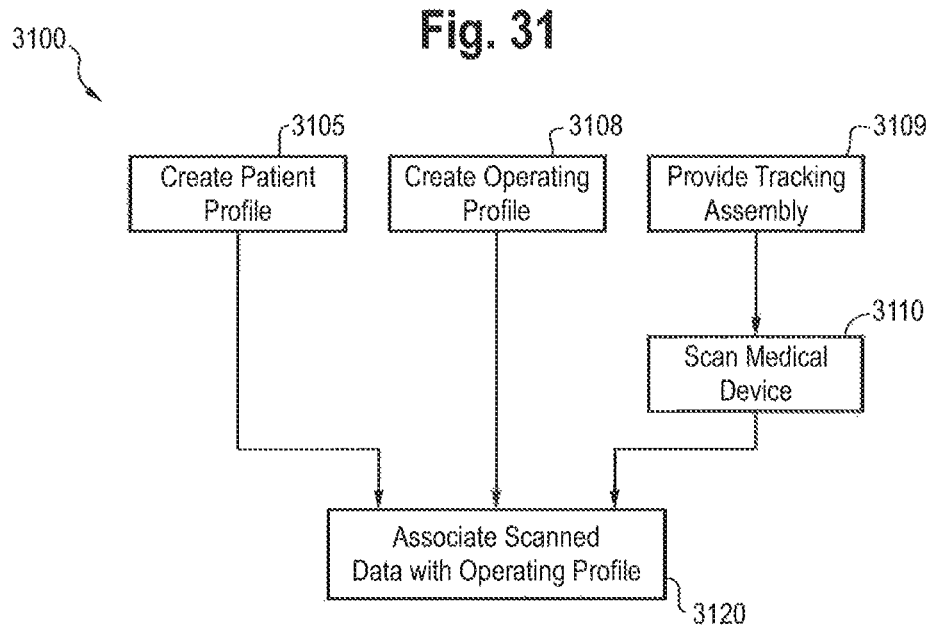
FIGS. 31-33 are flowcharts illustrating exemplary methods of tracking a medical device.
Figure 32:
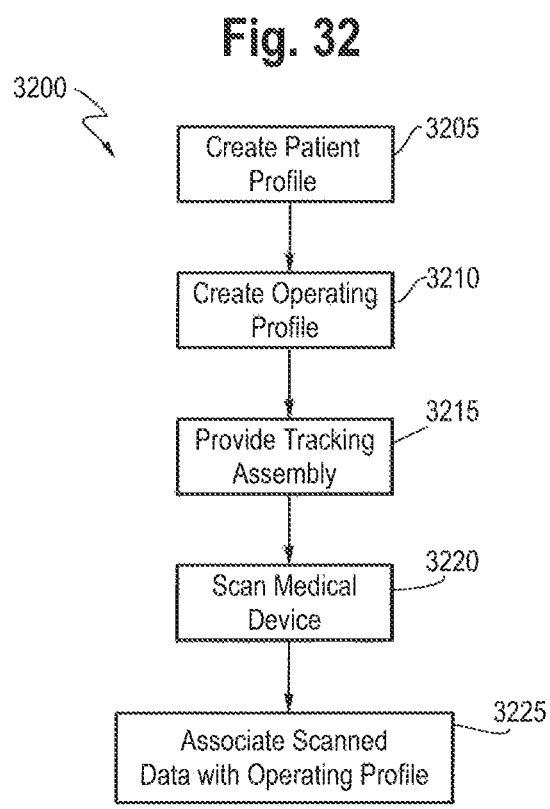
Figure 33:
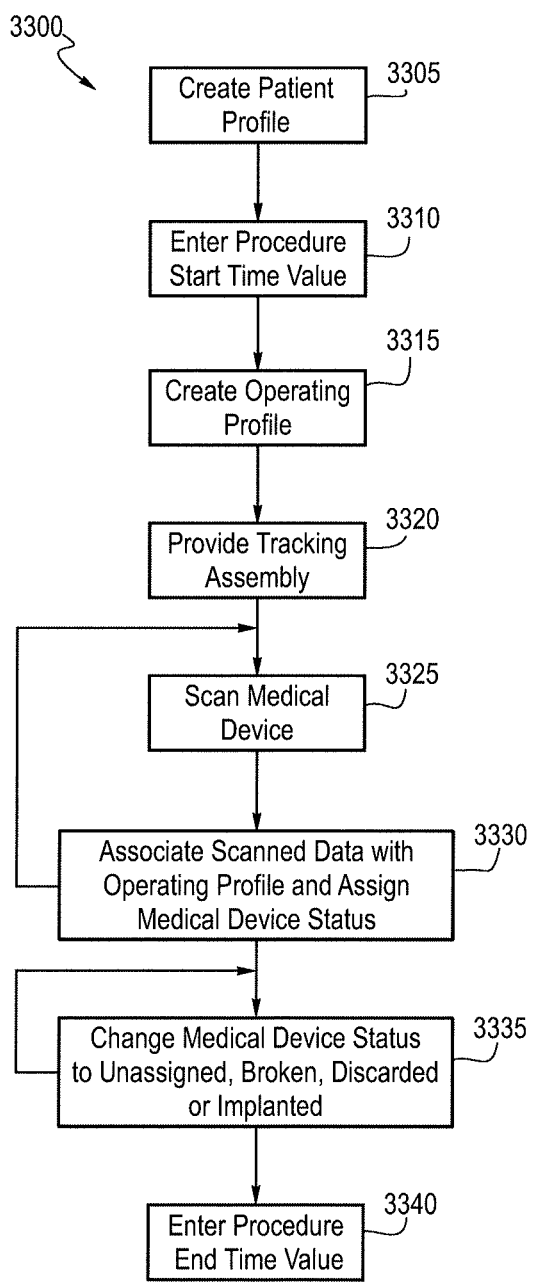

Exemplary methods are illustrated in FIGS. 31-33. In FIG. 31, the method 3100 includes three parallel steps: (1) creating a patient profile 3105, (2) creating an operating profile 3108, and (3) providing a tracking assembly 3109 and scanning a medical device 3110. The scanned data is then associated with the operating profile 3120. In FIG. 32, the method 3200 includes the steps creating a patient profile 3205, creating an operating profile 3210, providing a tracking assembly 3215, scanning a medical device 3220, and associating the scanned data with the operating profile 3225 as steps in series.

The method 3300 shown in FIG. 33 includes further detail. In step 3305 the patient profile is created, and a procedure start time value is entered into the patient profile (3310). The operating profile is created (3315) and the tracking assembly provided (3320) as with methods 3100 and 3200. The steps of scanning a medical device (3325) and associating the scanned data with the operating profile and assigning the medical device a status (3330) are repeated for each medical device tracked using the method, as described in further detail below.

As a medical procedure continues and the medical device is used on the patient, the method 3300 includes changing the medical device status to unassigned, broken, discarded or implanted (3335), and step 3335 is repeated for each medical device scanned. A procedure end time value can then be entered into the patient profile 3340.

The methods and systems provided for herein are described in further detail below. It is understood that the tracking assembly provided in any embodiment of the system and method described herein may be any embodiment or combination of embodiments described above.

In one embodiment, for example, the method of tracking a medical device comprises (a) creating a patient profile, (b) creating an operating profile comprising at least one surgical site, (c) providing a tracking assembly comprising a reader, the reader comprising a scanner, a housing enclosing the scanner, and a medical drape, (c) placing a medical device having an identifier over the reader, (d) scanning the identifier of the medical device to electronically record the medical device data, (e) associating the scanned medical device data with the at least one surgical site, and (f) using the medical device on a patient on the at least one surgical site.

In one embodiment, the method of tracking a medical device comprises (a) providing a tracking assembly comprising a reader, the reader comprising a scanner, a housing enclosing the scanner, and a medical drape, (b) covering the reader with the medical drape, (c) placing the reader covered with the medical drape in a sterile field, (d) providing a computer, (e) creating a patient profile using the computer, wherein the patient profile includes a value for a medical procedure start time, (f) creating an operating profile comprising at least one surgical site using the computer, (g) placing a medical device having an identifier over the reader, (h) scanning the identifier of the medical device to electronically record the medical device data in memory in the computer, wherein the scanner communicates with the computer using Bluetooth, (i) associating the scanned medical device data with the at least one surgical site using the computer, whereby the scanned medical device is assigned a status of assigned, (j) using the medical device on a patient on the at least one surgical site, (k) changing the status of the medical device to a status selected from the group consisting of unassigned, broken, discarded, or implanted, and (l) entering a value for a medical procedure end time into the patient profile.

It will be appreciated that the particular use of a medical device on a patient on the surgical site may vary depending on the type of medical device. For example, in the case of an implant, the step of using the medical device on a patient on the at least one surgical site comprising implanting the medical device in the patient at the at least one surgical site. In other embodiments, using the medical device may, depending on the specific medical device, include and is not limited to, cutting, clamping, implanting, piercing, drilling, separating, washing, rinsing, and stitching, among other actions.

In an exemplary embodiment, a method of tracking a medical device may proceed in further detail as follows.

A patient profile is created. In an embodiment, the method includes providing a computer including a display and a means for entering information (e.g., keyboard, mouse, stylus, touchscreen, microphone, etc.) and creating the patient profile using the computer. A patient profile may include such information as a patient identification number (e.g., assigned by a medical facility/medical group or use a government-issued or other identifying number), patient name, patient date of birth, patient age, patient gender, patient weight, patient height, patient email, phone number and/or other contact information, the name of surgeon performing the patient's operation, the surgeon's email, phone number and/or other contact information, patient diagnosis resulting in the need for surgery, patient prognosis, patient medical history information, patient lab work, patient medication, patient allergies/diet information, patient personal habits, patient blood/genome type, and/or pre-surgery notes (from prior appointments or pre-op evaluation). Other patient information may be input or obtained if relevant to the patient's medical profile, including, for example, insulin readings prior to starting surgery.

In one embodiment, the patient profile also includes the sterilization date of some or all medical devices being used during a medical procedure, if applicable. This information may be entered In one embodiment, some or all of this information is entered during a pre-op appointment. In other embodiments, the computer, and specifically the program used to create the patient profile, may communicate with existing medical provider databases and pull some or all of the requested information from those existing medical provider databases using a patient's name, number or other identifying information. In still a further embodiment, the computer, and specifically the program used to create the patient profile, may communicate with an existing electronic medical records (EMR) system or electronic health records (EHR) system, if applicable.

In another embodiment, the patient profile information is obtained by scanning the patient's hospital band.

Depending on when the patient profile is created, the step may be completed by a nurse, surgical technician, surgeon or other doctor.

In still a further embodiment, the patient profile is created or otherwise accessed when the patient is in the operating room to start the procedure. In such embodiment, the creation of the profile starts a clock which counts the time it takes to complete the operation, and that start time is saved with the patient profile. In another embodiment, such as, for example, when the patient profile is created prior to surgery, a nurse, surgical technician, surgeon or other doctor may start the clock separate from the entry of the remaining data in the patient profile.

A operating zone profile for the patient is also created. In an embodiment, the method includes providing a computer, as described above, and creating the operating zone profile using the computer. In some embodiments, the operating zone profile may be created before or simultaneously with the creation of the patient profile. In other embodiments, the operating zone profile may be created after the creation of the patient profile.

In one embodiment, the step of creating an operating zone profile includes selecting at least one surgical site. In an embodiment, the computer used by the nurse, surgical technician, surgeon or other doctor to create the operating zone is configured to update the display of the computer to show hierarchical anatomical systems tree, whether textual description or with a graphical depiction. For example, in one embodiment, the display initially shows a list of broad anatomical systems (e.g., muscular system, endocrine system, cardiovascular system, skeletal system, integumentary system, etc.). Once a broad anatomical system is selected, the display is updated to provide a continually narrowing list of potential operating zones/regions. For example, if the skeletal system is selected, an initial narrowed list of potential operating zones/regions may include cartilage, bones and joints. If further narrowed, such as, for example, selecting bones, the display may be updated to display an continually-narrowing listing of body quadrants/regions. For example, the selection of bones may result in a further updated display showing the options of cranial, facial, trunk, pelvis, legs, upper limbs, lower limbs, etc. The further selection of trunk may result in a further updated display showing the options of neck, spine, shoulders, lower back, buttocks, calves, etc. The continually-narrowing displays continue until, ultimately, the specific bones/sets of bones associated with the drilled-down region are displayed. For example, upon selection of spine, the updated display may show the options of full spine, cervical, thoracic, lumbar, sacral, coccyx, etc. In another embodiment, a search feature may be provided, into which a user may enter a term associated with a specific region or surgical site, allowing the user to bypass all or at least a portion of the drilling-down process. For example, a user may simply search for "coccyx" to bypass the above-described drilldown process.

A visual representation of potential operating zones/regions may also be used to create the operating zone profile, whether along or in conjunction with the text-based selections. For example, the display may be updated to display a figure of a human body or relevant parts thereof. The portion(s) of the human body displayed may be narrowed or limited based on a user's text-based operating zone selections and/or clicking or otherwise selecting portions of the human body illustration, such as described above.

In an embodiment, a user may also be provided with a toggle selection enabling the user to change the human body illustration from a front view to a back view and vice versa.

The process is repeated until all surgical sites are selected. In an embodiment, surgical sites may be categorized for display by zone. Once all surgical sites are selected, the patient's operating zone profile is created and surgery may commence.

Either before, during or following the creation of the patient profile and/or surgical profile, the present method includes the steps of providing a reader as described above and placing a transparent sterile sheath over the housing structure of the reader device. Once the reader is set up and operation, a medical device having an identifier is placed on or over the top surface of the transparent sterile sheath above the aperture of the housing structure, and the identifier is scanned.

In an embodiment, the scanned data is stored, permanently or transiently, in a database and, in some embodiments, permanently associated with a patient profile. In an embodiment, the scanned data is a code (e.g., barcode, QR code, etc.) or other unique identifier. The identifier may be assigned by a manufacturer or the health care provider. In either case, in an embodiment, the computer is capable of communicating with and accessing manufacturer and/or health care provider databases to pull additional information about the medical device scanned. For example, in an embodiment, an image of the medical device if available will be displayed with the scanned data. For caching purposes, it may be beneficial for the images to load from an administration database and stored locally. Other information which may be pulled from a manufacturer and/or health care provider database include the medical device name (e.g., trade name, common name), manufacturer and other available identifying/descriptive information.

In the embodiment described, the computer display is updated to display the scanned data. A user (e.g., nurse, surgical technician, surgeon or other doctor) then associates the scanned data with a surgical site in the patient's operating profile.

In one embodiment, the display is updated to show the scanned data on one portion of the display and the surgical site(s) on another portion. Surgical site(s) may be displayed graphically (e.g., human body illustration) or textually. To quickly navigate between surgical sites using a graphical depiction, the display may be capable of receiving user-input to zoom, rotate, and/or pan around the graphic. The scanned data/surgical site association may be made by clicking and dragging the scanned data to the corresponding surgical site. In other embodiments, a drop down/pop up menu associated with the scanned data may display the available surgical site(s) and allow a user to select the site from the drop down/pop up menu.

It is contemplated that unassigned items will remain visible on the portion of the display containing the scanned data. However, once scanned data associated with a medical device is assigned to a surgical site, the scanned data will disappear so as not to be associated with another surgical site. In other embodiments, once scanned data associated is associated with a surgical site, the display may update to show that particular portion of scanned data in a different color (e.g., a color assigned to a given surgical site) or otherwise indicate to a user that the data is associated with a surgical site.

In one embodiment, each surgical site (and, in some embodiments, specific locations within a surgical site) have a unique [RegionID]. The [RegionID] may be one used with a healthcare provider's system, and therefore, hypothetically, unique to each healthcare provider, or a standard [RegionID] used by the present system and method. When viewing the scanned data associated with a medical device, the scanned data may be prepopulated with a placeholder designation ("[RegionID]") which will dynamically update as scanned data is associated with a surgical site. In other embodiments, a placeholder "[RegionID]" may be manually updated by a user if desired.

In addition to associating a medical device (via the scanned data) with a surgical site, a user may also be able to mark a medical device as broken (prohibits the scanned data from being associated with a surgical site), discarded (removed from any associated surgical site and prohibited from further association with another surgical site), implanted (prohibits removal of the association with the surgical site), and multi-zone (permits the scanned data to be associated with more than one surgical site).

In an embodiment, the display may be updated by a user to filter the scanned date and display only what is associated with a particular zone, such as, for example, by using a tab-like structure or other filter selection.

In an embodiment, and particularly when each medical device being scanned has a unique identifier, the program displays a notification when a medical device is scanned more than once and does not permit duplicative scanning. However, in some embodiments, and particularly when using some medical devices, the identifier of two or more medical devices may be the same. This is often the case with surgical instruments, where one model of instrument will always have the same identifier. In such instances, an override is possible and the additional duplicate item will show in the scanned data. If the duplication was still inadvertent, the duplicate data may be discarded.

As the scanned data is associated with an operating profile, in some embodiments a user may review the data. For example, clicking on an identified surgical site may initiate updating of the interface to display all medical devices associated with that surgical site. From there, a user may also be able to mark a medical device as broke, discarded, implanted, or multi-zone, and even, in some embodiments, change the medical device's association with the selected surgical site. In some embodiments, a user may also be able to view a comprehensive list of the scanned data to view all medical devices, whether sorted by time scanned, numerically (e.g., by identification number/key), alphabetically, associated surgical site, or other organization.

In some embodiments, a user may also be able to review the surgical sites associated with the operating profile. For example, a number of tabs may be provided at the top of a display, each associated with a selected surgical site. A user may then select a desired tab and view the scanned data (and other data, if available) associated with that surgical site, including, for example, the medical devices, status of the medical devices, surgical notes, etc.

In one embodiment, users may discard medical devices from a surgical region and/or operating profile by clicking on a desired medical device and dragging an icon representing that medical device to a designated portion of the display (e.g., labeled "discard"). In some embodiments, a user may be able to view all discarded medical devices and restore such medical devices.

As will be understood by one of skill in the art, the steps of creating the patient profile, creating the operating profile including at least one surgical site, providing the scanner and associating the scanned data with the at least one surgical site may be completed prior to, during or both prior to and during an actual medical procedure or operation. For example, the steps of creating the patient profile, creating the operating profile including at least one surgical site, providing the scanner and associating the scanned data with the at least one surgical site may all be completed prior to actually starting a procedure on a patient. In other embodiments, one or more of the steps of creating the patient profile, creating the operating profile including at least one surgical site, providing the scanner and associating the scanned data with the at least one surgical site may be completed during a procedure.

In any event, once a medical procedure is started, a user (e.g., nurse, surgical technician, surgeon or other doctor) enters a start time into the patient profile by either entering a numeric value for a start time or activating a clock associated with the computer. Upon completion of the medical procedure, an end time is entered into the patient profile by either entering a numeric value for an end time or stopping the clock.

In one embodiment, in order to successfully enter an end time for a medical procedure, all medical devices used must have a status of implanted, broken or discarded. In other words, if any scanned data is still associated with a surgical site and not identified as implanted, an end time value may not be entered into a patient profile.

As will be understood by one of skill in the art, the present process may necessarily include providing a sterile computer.

As mentioned above, in an embodiment, a user (e.g., nurse, surgical technician, surgeon or other doctor) may be able to enter notes which may be associated with a patient profile and/or operating profile, generally, or a surgical site or medical device, specifically. In some embodiments, a user may have to specifically select an option to export notes to a patient profile. In one embodiments, notes may be entered during the medical procedure and, upon successfully entering an end time value in a patient profile, a user may be prompted to review the notes prior to the notes being exported to the patient profile.

In an embodiment, after an end time value is successfully entered to a patient profile, a list of all medical devices scanned during the procedure is made available for review, for example, in the form of a scanned medical devices report. In one embodiment, a scanned medical devices report includes information such as the scanned data for the medical device, any [RegionID] or surgical site designation, the status of the medical device and/or a link to any notes relating to the medical device. In an embodiment, the information displayed may be filtered or sorted by a user, for example, to show only medical devices of a certain status (e.g., implanted), medical devices associated with a selected surgical site, etc. After review of the medical devices used during the procedure, a user may be prompted to export the information to the patient profile. In other embodiments, the list of medical devices (e.g., scanned medical devices report) may be automatically exported to the patient profile upon successfully entering a medical procedure end time in the patient profile.

In one embodiment, a user may be able to display the list of medical devices scanned pictorially over a displayed human figure, such as, for example, the figure displayed when selecting surgical sites.

In some embodiments, after successfully entering a medical procedure end time in a patient profile and/or exporting additional information to the patient profile, a case number is assigned to the medical procedure event. The case number may be automatically generated by the healthcare provider and may be used by other departments (e.g., billing, inventory, administration, etc.) of the healthcare provider.

In one embodiment, the present system and method includes using an administration site to enable healthcare provider administration and, in some embodiments, medical device manufacturers who have appropriate permissions to access databases associated with the system. Typically such an administration site will be hosted behind the healthcare provider's firewall as an on-premise instance in order to enable higher security protocols (e.g., HIPPA compliant). Administrators with appropriate access to the administration site may be able to look up existing cases using the case number assigned upon successfully entering a medical procedure end time in a patient profile or create (or begin creating) a patient profile (e.g., in anticipation of an upcoming procedure, such as, for example, during patient intake questioning).

Administrators may also use the administration site to send recall alerts to a patient, surgeon, hospital/healthcare provider, insurance/payer, medical organization, state department, manufacturer and/or other individual or entity. In some embodiments, the recall alerts are sent be electronic communication (e.g., email). In some embodiments, access to an EMR or HER system in order to properly acquire the relationships necessary to send the alerts.

In an embodiment, the system described herein, and particularly the administration site, may also be used to track and manage inventory. For example, an administrator can look up medical devices by type, manufacture, part number, lot number, serial number, patent (e.g., in the case of an implanted medical device, such as for tracking purposes), or other desired field.

The administration site may also be used to control/authorize users and manage the access/privileges of the different users. For example, the administration site may be used to assign or change user names, passwords and contact information for users. Users may also be sorted into or assigned groups, whether based on level of privileges, healthcare system, facility, degree (e.g., medical doctor, registered nurse, certified surgical technician, etc.), or even specialty.

In an embodiment, the present disclosure provides a system for tracking implants comprising (i) a reader, (ii) a medical drape, and (iii) a computer. In an embodiment, the reader may be any one or combination of two or more embodiments described herein. In an embodiment, the medical drape may be any one or combination of two or more embodiments described herein. In an embodiment, the computer may be any one or combination of two or more embodiments described herein.

In an embodiment, communication between the reader and the computer is through a wireless system, including but not limited to Bluetooth. In an embodiment, the computer has software that allows for tracking and recording implant information. The software can be integrated and communicate with multiple systems and/or databases, such as external systems and/or databases, including but not limited to a electronic health records, electronic medical records, hospital and clinic databases containing patient information, databases containing scheduling information, databases containing physician and medical staff information, databases containing hospital inventory information, payer systems, databases and records of the manufacturer of the medical device, insurance and reimbursement systems, and government databases, such as the Food and Drug Administration.

In an embodiment, a method for tracking a medical device comprises (a) providing a tracking assembly comprising a reader, the reader having a scanner, a housing enclosing the scanner, and a medical drape, as set forth above in any one or combination of embodiments, (b) placing a medical device having an identifier over the reader, (c) scanning the identifier of the medical device to electronically record the medical device data, (d) transmitting the medical device data to one or more databases or systems, as described above, and (e) using the medical device in a medical procedure on a subject.

In an embodiment, the database or record system includes, but it not limited to, at least one of electronic health records, electronic medical records, hospital and clinic databases containing patient information, databases containing scheduling information, databases containing physician and medical staff information, databases containing hospital inventory information, payer systems, databases and records of the manufacturer of the medical device, insurance and reimbursement systems, and government databases, such as the Food and Drug Administration.

The TRACTUS™ System

The TRACTUS™ System is a comprehensive, fully integrated hardware and software solution that provides rapid and accurate medical implant UDI capture and documentation in the sterile field of the operating room (OR). TRACTUS™ is a "turnkey" solution that addresses and meets the unique complexities and challenges in conveying medical implant UDI for products such as orthopedic implant sets used in various types of spine, trauma, cranio-maxillofacial, or extremity surgeries.

The TRACTUS™ hardware, such as a reader in accordance with one or more embodiments described herein, has been designed to sit atop a Mayo stand and consists of a battery-powered high-speed barcode scanner that wirelessly connects to a small laptop device containing the TRACTUS™ software.

Upon capturing the medical device UDI information, the TRACTUS™ reader parses the information and wirelessly communicates with the software to identify and document the item, the lot number, serial number, expiration date, etc.

Using a simple drag-and-drop functionality (e.g., click-and-drag), the software operator may assign the final placement of the implanted product (and/or use zone or surgical site for an implanted product or other medical device used).

With a simple click of a button, the TRACTUS™ software then populates all relevant information into the appropriate fields of any hospital's existing clinical documentation system—in real time. Before TRACTUS™, this tedious and meticulous documentation task was very time consuming, error-prone, and was typically assigned to nurses and technicians. With TRACTUS™, the documentation process is reduced dramatically to a process lasting mere seconds—with an unparalleled level of accuracy.

The advanced scanning capabilities of TRACTUS™, in combination with cloud-based database(s) of products, ensures there are no more double entries, no difficulties identifying and recording a product in the clinical documentation system, and no multiple steps to capture lot number and expiration date. Simply scan, drag and then drop the desired implant to the appropriate anatomical location. TRACTUS™ presents unparalleled efficiency, accuracy, and overall time saves when it comes to clinical documentation.

Through the power of TRACTUS™ reports, users are also able to run meaningful web-based reports instantly—using real-time, accurate data. These reports are immediately available and can be used to document each procedure, the products used, and their pedigree information, which in turn assists with product re-ordering, product utilization and trends analysis, billing, auditing, and much more.

Some TRACTUS™ benefits include:

1. Sterile field UDI documentation solution (as small as 1 mm$^2$ 2D data matrix)
2. Unmatched point of care clinical documentation (during implantation)
3. Intuitive software allows for positional documentation and visualization of implants
4. Tracks utilized and discarded implants (full accountability)
5. Immediately identify counterfeit implants not registered in GUDID database
6. Completely integrated facility EMR interface
7. Fully customizable—may be used as a standalone solution or integrated with current inventory management of UDI tracking systems
8. Benchmark testing yielded 100% accurate throughput of scanned information
9. Eliminates inaccurate recordkeeping, billing and identifies actual implanted products
10. Builds database for recall identification and post market surveillance of implants
11. Comprehensive reporting capability TRACTUS™ key features includes: (a) immediate, accurate and efficient UDI scanning in the sterile field; (b) accurate tracking and documentation; (c) completely cordless (powered via rechargeable battery and communicates via Bluetooth 3); (d) product utilization and final placement capture; (e) discarded products identification; (f) ascertain surgeon and tem members, hospital, and implant specific utilization and outcomes; (g) accurately and immediately maintain a record of all implantable products used in a surgery; (h) reduce errors and redundancy; (i) save valuable time by providing instant documentation; (j) cloud based product database is updated daily; (k) inventory control system easily tracks and manages inventory including simultaneous tracking of multiple implant systems and auto ordering for replenishment; (l) enhance expiration and recall management; (m) improve billing and reimbursement; and (n) immediately identify counterfeits.

In one embodiment, the computer is configured with software that may be integrated and communicate with hospital and clinic (ASC) databases, such as, for example, those containing patient information, doctor/surgeon/procedure scheduling information, physician and medical staff information, and/or medical device inventory information.

TRACTUS™ key benefits to Hospitals and Clinics (e.g., ASCs) include: (a) save time in the OR by automating the implant documentation process; (b) accurately and efficiently document implant UDI and usage; (c) used in the sterile field—therefore, there is no error-prone pre- or post-op manual entry of information to input the device information into the system software; (d) reduces labor costs by eliminating manual data entry of information across multiple departments; (e) analyze device and implementation trends, giving a healthcare team a clear picture of device and surgeon performance; (f) analyze and compare cost and performance by device, surgeon, surgical staff, implantation time, defective units, wasted units, and many other variables; (g) ensure accurate device utilization and billing; (h) improve tracking of recalled and expired devices; (i) multilevel user access to control data security; (j) implant tracking of all devices across all hospital departments—any item with a lot/serial/UDI number can be tracked; (k) UDI can be used to accurately identify the device through its distribution and use; (l) visualizes image of final implant locations inside patient; and (m) further clinical care benefits, including (i) alerts patients and caregivers of device management schedules, (ii) enables building of meaningful quality and performance measures and clinical decision support tools, (iii) improves recall patient identification and effectiveness, (iv) increases ability to conduct active surveillance, (v) links device to diagnosis and other elements of patient care, (vi) makes device available for summary views of patient, (vii) provides rapid access to accurate, standardized device information, and (viii) supports care coordination and future patient care programs.

In one embodiment, the computer is configured with software that may be integrated and communicate with medical device manufacturer and distributer databases, such as, for example, those containing information pertaining to inventory, purchase orders, doctor/surgeon/procedure preferences, use statistics, recall information, and/or representative information.

TRACTUS™ also provides benefits to manufacturers and distributors. Device representatives spend much of their time managing inventory and completing paperwork, hoping to get paid on a timely basis. Because TRACTUS™ is digital and accurately and efficiently identifies each part used, distributors may redeploy their representatives to more productive activities. Manufacturer and distributor benefits include: (a) ensure that institutions maintain appropriate inventory levels; (b) generate immediate purchase orders; (c) immediately identify implants utilized; (d) identify surgeons by implants utilized; (e) immediately know when inventory has been used; (f) instant electronic return of implant and tissue records; (g) manage purchased, consigned or loaned implants; (h) quickly replace used implants in a set; (i) speed up reimbursement—both the hospital and distributor know which implants were used in a case; (j) track surgeon and hospital utilization and performance trends; and (k) gain access to more institutions.

In one embodiment, the computer is configured with software that may be integrated and communicate with payer databases/systems, such as, for example, those containing patient information, physician/surgeon/medical staff/healthcare facility information, recall information, policy information, claim status information, and/or claim processing information.

TRACTUS™ also provides benefits to payers. Once health plans learn of device recalls, it is likely the health plan does not know how many members are affected and whether those affected will receive the treatment they need. Payers may be unable to determine whether members who underwent a procedure involving a specific type of device actually received the device which has been recalled or a similar device from another manufacturer. Payers may not know if the manufacturer is replacing the device at no cost or helping patients to cover copayments andmeet deductibles. When a claim comes in, the health plan might not know whether it is for a member who is receiving the procedure and device for the first time, or for one who is having the procedure to replace the recalled device. What is known for certain is that a patient has undergone a procedure, a claim has been presented, and payment is required. Payer benefits include: (a) compare costs, revisions, waste, and recalls by manufacturer, device, hospital and/or surgeon; (b) identify and measure outcomes by physician, hospital and/or implants; (c) alert patients when a recall occurs; (d) access to member information by recalled device; (e) identify prior implantations by member/surgeon/payer; (f) eliminate overbilling by ensuring accurate device utilization by case; (g) identify actual devices implanted as opposed to paying for wasted or defective implants; (h) know exactly where each implant has been placed, targeting devices that need to be replaced because of a recall; and (i) identify the responsible party when a revision or replacement is required.

In one embodiment, the computer is configured with software that may be integrated and communicate with government databases, such as, for example, those associated with the Food and Drug Administration (e.g., containing recall information, marking rules, etc.).

Overview of how TRACTUS™ works:

During preparation for surgery, the TRACTUS™ software is launched and all relevant patient information is uploaded to the TRACTUS™ software form the hospital's existing clinical documentation system (e.g., create patient profile).

The TRACTUS™ reader is covered by a sterile sheath and drape, such as described herein, and is placed in the sterile field—with close proximity to the patient.

Upon scanning the UDI data matrix on products, the TRACTUS™ reader wirelessly communicates with the software and parses the information, identifies the item, and then captures additional information, such as lot number, serial number and expiration date—associating these values with the patent (and/or patient profile).

The surgeon verifies the positional placement of the implant and/or surgical site on which a medical device will be used and, using a simple drag-and-drop functionality, the software operator assigns the final anatomical placement of the implanted product or final anatomical use of the medical device. Discarded and defective products are also documented.

Once placed, a visual image of the implant's placement (or device's usage area) is immediately available to the surgery staff, and a permanent record is maintained.

The implanted, discarded and unused medical device (e.g., implant) information, as well as the positional placement information for an implanted device, is pushed to the hospital's existing clinical documentation and inventory management systems.

A reader used with the TRACTUS™ method and system may be according to any one or any combination of two or more embodiments disclosed herein. In an embodiment, a reader used with the TRACTUS™ method and system includes (1) a battery power source capable of running a scanner (e.g., camera) for at least 24 hours; (2) the battery power source being self-contained and removable; (3) the battery power source being rechargeable; (4) a battery recharging station; (5) a proximity sensor (e.g., photoeye) to turn the light on and off upon when an object is placed in front of the sensor; (6) Bluetooth 4 communication with software system; (7) power button; (8) battery power level indicator; (9) new light source; (10) printed circuit board (PCB) to control the electronic systems; (11) firmware programming ensuring highly accurate reads of very small 2D data matrix codes.

Software used with the TRACTUS™ method and system may be according to any one or combination of two or more embodiments disclosed herein. In an embodiment, software used with the TRACTUS™ method and system has the following features: (1) allows all of the implant unique device identifier information to be collected, along with an image of the implant and images of the anatomical systems that drill down to zones in the body where the implant placement may be identified; (2) integrated into EMR systems, collecting patient, surgeon and other information as well as pushing utilization data to hospital records; (3) linked to the FDA GUDID (Global Unique Device Identification Database) to verify FDA approved implants as well as recalled devices; (4) has an E-commerce system allowing implant manufacturers to upload device information and collect post-op utilization data; (5) has reporting capabilities including implant surgery type, time between implants, discarded vs implanted devices, reason for discard, by patient and/or surgeon age, sex, primary/secondary diagnosis, etc.; (6) can identify all patients and their implant location with recalled devices; (7) is capable of allowing multiple surgeons (think trauma) to merge data on the same patient; (8) provides a high level of platform stability and security; (9) collects information on the local laptop and pushes it to the cloud upon case completion; (10) can be controlled by a remote IT technician; and (11) has multiple levels of user access.

Because all implants are stored in TRACTUS™ cloud-based database of products, chain of custody for all implants will start with the implant manufacturer and follow the implant through the entire product life cycle. Product tracking throughout the entire life cycle enhances patient safety and post market surveillance activities. Data from the implant registry, coupled with TRACTUS™ utilization provides detailed information that is valuable in reducing cost and improving outcomes. Further, TRACTUS™ development will provide information that may become helpful to predict risk for complications, such as infection and pain after surgery. By understanding risks, healthcare providers are better able to manage care before and after surgery to decrease the chance of complications. Internal registries will extend knowledge from published medical studies to how these implanted medical products perform in patients. This allows patients and physicians to make the best choices about care. Collecting and analyzing this information for all patients nationwide can better answer questions, address concerns and give the latest information on surgery and implants. Registries for patients with chronic conditions and who have received implanted devices are kept. Additional tools may be added on to TRACTUS™ to enable clinicians to use these techniques across the spectrum of medical care.

TRACTUS™ is linked to the FDA device recalls database and receives all recall alerts (Levels 1-3). In addition, TRACTUS™ may be linked to other organizations, such as payers, to provide patient-specific recall information. Information may also be received and/or sent to the FDA's Manufacturer and User Facility Device Experience (MAUDE).

Moreover, non-sterile products such as orthopedic implant sets used in various types of spine, trauma, craniomaxillofacial, or extremity surgeries often contain many individual components that have been separated from their original packaging. The FDA's UDI Rule states that Class II and III medical implants must be direct part marked. By scanning and documenting UDI information in the sterile field, form a direct marked part, the most accurate device information is documented in the hospital's clinical documentation system. This eliminates the need for manual documentation of implant UDI data.

As it pertains to recalls, in rare cases when implantable products are recalled, the TRACTUS™ registry allows medical facilities to identify instantly all the patients who may be affected. This lets the surgeon and hospital connect instantly with the implant company and the FDA to quickly and accurately determine corrective action. When a recall occurs, having an accurate automated national registry allows medical providers to reach patients before their recalled devices fail.

The TRACTUS™ system also ensures accurate charge capture and reimbursement. By verifying that the invoice for a clinical product matches the product used for patient care, and that it is available immediately for processing, a healthcare provider is able to greatly reduce the time it takes and ensure complete accuracy to generate the appropriate documentation needed for reimbursement. Because TRACTUS™ identifies the exact medical devices (e.g., implants) used, the healthcare provider will avoid over- and underbilling by verifying the exact devices used are captured on the facility's charge master.

The present disclosure includes the following embodiments:

An assembly for tracking implants comprising
a reader comprising:
a scanner,
a housing structure comprising
an aperture on a top surface of the cover, and
a base comprising
an inset groove to receive the cover, and
optionally a transparent sterile sheath having a top surface and side walls,
wherein the transparent sterile sheath encases the cover of the housing structure,
wherein the scanner is positioned to form a focal point above the aperture,
wherein the scanner is enclosed in the housing structure;
a medical drape attached to the side walls of the transparent sterile sheath; and
a computer in communication with the reader.

The assembly wherein the reader further comprises an LED and a scanner mounting structure supporting the scanner and LED device wherein the scanner mounting structure is attached to the base.

An assembly for tracking implants comprising
a handheld reader;
a housing structure comprising
a cover comprising
an aperture on a top surface of the cover, and
a base comprising
an inset groove to receive the cover;
optionally a transparent sterile sheath having a top surface and side walls,
wherein the transparent sterile sheath encases the cover of the housing structure,
wherein the handheld reader is secured to the base to form a focal point above the aperture,
wherein the handheld reader is enclosed in the housing structure;
a medical drape attached to the side walls of the transparent sterile sheath; and a computer in communication with the handheld reader.

A reader comprising:
a scanner;
an LED;
a scanner mounting structure supporting the scanner and LED;
a housing structure comprising
a cover comprising
an aperture on a top surface of the cover, and
a base comprising
a top surface to receive the scanner mounting structure,
an inset groove to receive the housing structure; and
an optional transparent sterile sheath encasing the cover of the housing structure,
wherein the scanner mounting structure is attached to the base
wherein the scanner and LED are positioned to form a focal point above the aperture,
wherein the scanner, LED and mounting structure are enclosed in the housing structure.

The reader wherein the cover further comprises at least one radial pin extending from a side surface of the cover.

The reader wherein the cover further comprises at least one pin hole in the side of the cover to receive a vertical pin.

The reader wherein the base further comprises at least one vertical pin extending up through the inset groove.

The reader of claim 4 wherein the base further comprises an inset channel extending radially from the scanner mounting structure to the edge of the top surface of the base, and a removable channel cover.

The reader having a transparent sterile sheath covering the cover of the reader.

The reader having a transparent sterile sheath covering the cover of the reader wherein the transparent sterile sheath further comprises at least one radial pin slot to receive the radial pin from the cover.

The reader wherein the scanner is capable of scanning 2×2 mil etched identifiers.

The reader wherein the top surface of the transparent sheath in the area above the aperture of the cover corresponds with the focal point of the scanner and LED.

The reader further comprising a medical drape wherein the medical drape does not obstruct the aperture of the housing structure and wherein the medical drape extends radially out from the side surface of the housing structure.

The reader wherein the transparent sterile sheath has magnifying abilities.

The reader wherein the transparent sterile sheath is formed of a single piece of transparent plastic.

The reader wherein the transparent sterile sheath is disposable.

A method of using a reader comprising the steps of:
providing a reader comprising:
a scanner;
an LED;
a scanner mounting structure supporting the scanner and LED device; and a housing structure comprising
a cover comprising
an aperture on a top surface of the cover, and
a base comprising
a top surface to receive the scanner mounting structure,
an inset groove to receive the housing structure,
wherein the scanner mounting structure is attached to the base
wherein the scanner and LED are positioned to form a focal point above the aperture,
wherein the scanner, LED and mounting structure are enclosed in the housing structure;
placing a transparent sterile sheath over the housing structure of the reader;
placing an implant having an identifier onto the top surface of the transparent sterile sheath above the aperture; and
scanning the identifier of the implant to electronically record the stored data.

The method further comprising the step of positioning a medical drape to cover the remaining portions of a reader.

The method wherein the identifier on the implant is an etched 2×2 matrix containing data regarding the implant.

The method wherein positioning the medical drape to cover the remaining portions of a reader device comprises unrolling the medical drape from the transparent sterile sheath to extend the medical drape around the remaining portions of the reader device.

A tracking assembly comprising:
a reader comprising:
a housing structure that includes a base and a cover;
a scanner having a scanner housing, where the scanner housing is at least partially positioned in a cavity provided in the base; and
an aperture provided in the cover, where the cover is configured to receive a transparent sterile sheath to at least partially encase the cover.

The assembly further comprising a transparent sterile sheath positioned over the cover.

The assembly further comprising a medical drape attached to a side wall of the transparent sterile sheath.

The assembly where the medical drape extends radially and downwardly from the transparent sterile sheath.

The assembly where the medical drape is removably secured to the transparent sterile sheath by an elastic band.

The assembly where the medical drape is permanently secured to the transparent sterile sheath.

The assembly where the combination of the transparent sterile sheath and the medical drape substantially cover the housing structure to substantially limit exposure of the housing structure to the atmosphere.

The assembly where the scanner is positioned in the base to form a focal point on a top surface of the transparent sterile sheath above the aperture.

The assembly where the reader further comprises a scanner mounting structure supporting the scanner wherein the scanner mounting structure is positioned substantially in the cavity and secured to the base.

The assembly where the scanner is in communication with a computer device located apart from the reader, where the computer device is capable of receiving and storing information obtained from the identifier upon being scanned by the reader.

The assembly where the scanner is capable of scanning 2×2 mm etched identifiers.

A tracking assembly comprising:
a reader comprising:
a scanner;
a scanner mounting structure supporting the scanner;
a housing structure that includes a cover with an aperture on a top surface of the cover and a base secured to the cover,
where the housing structure is configured to receive a one or more coverings to at least partially enclose the housing structure,
where the scanner mounting structure is secured to the base, and
where the scanner and scanner mounting structure are substantially enclosed in the housing structure.

The assembly where the one or more coverings includes a transparent sterile sheath positioned over the cover.

The assembly where the one or more coverings further includes a medical drape attached to a side wall of the transparent sterile sheath.

The assembly further including a cavity positioned inside the base, where the scanner is substantially positioned inside the cavity.

The assembly where the scanner includes a scanner housing attached to the scanner mounting structure.

The assembly where the one or more coverings includes a transparent sterile sheath and a medical drape.

The assembly where the one or more coverings includes a transparent sterile sheath and a medical drape attached to a side wall of the transparent sterile sheath.

The assembly where the scanner is capable of scanning 2×2 mm etched identifiers.

The assembly where a top surface of the transparent sheath in an area above the aperture of the cover corresponds with the focal point of the scanner.

The assembly where the scanner housing has a lens secured thereto, where the lens includes a front surface, where the front surface is situated between about 3 inches to about 5 inches from the aperture of the cover.

The assembly where the transparent sterile sheath includes a sheath top surface having at least one of a convex portion and a magnifying portion.

The assembly where the transparent sterile sheath is formed of a single piece of transparent plastic.

The assembly where the transparent sterile sheath is disposed of after identifiers have been received for all the medical devices implanted in a single patient during an operation.

The assembly where the sheath is rigid and cylindrical in shape.

The assembly where the sheath is cylindrical in shape and includes a locking mechanism.

The assembly where the base of the reader includes a diameter that extends between about 6 inches to about 10 inches.

The assembly where the scanner is connected via a cord to a computer located outside the housing structure.

A method of using a tracking assembly comprising the steps of:
providing a tracking assembly comprising:
a reader comprising:
a scanner;
a scanner mounting structure supporting the scanner;
a housing structure comprising:
a cover comprising:
an aperture on a top surface of the cover; and
a base secured to the cover, where the base includes a cavity;

where the scanner mounting structure is positioned in the cavity of the base, and where the scanner and scanner mounting structure are substantially enclosed in the housing structure;
covering the cover with a transparent sterile sheath;
placing an implant having an identifier over the aperture; and
scanning the identifier of the implant to electronically record the implant data.

The method further including attaching a medical drape to the transparent sterile sheath.

The method where the identifier on the implant is an etched 1.4×1.4 mm matrix containing data regarding the implant.

The method further including sensing an implant having an identifier, when the implant is positioned above the aperture and automatically obtaining a scan of the identifier.

A tracking assembly comprising:
a reader comprising:
a housing structure that includes a base and a cover; and
a scanner positioned in the housing structure for scanning a medical implant;
a sterile sheath positioned on the cover; and
a sterile drape secured to the sterile sheath, where the sterile drape and the sterile sheath substantially enclose the housing structure.

The assembly where the sterile drape is permanently secured to the sterile sheath.

The assembly where the sterile drape includes a drape lower portion that at least partially encloses one or more cords extending from the housing structure.

The assembly where the sterile drape extends radially and downwardly from the sterile sheath.

The assembly where the sterile drape is removably secured to the sterile sheath.

The assembly where the permanent securement of the drape to the sterile sheath provides an airtight seal therebetween.

The assembly further comprising an aperture in the cover to allow optical signals to pass between the scanner and the medical device.

The assembly where the scanner is positioned in the base to form a focal point on a top surface of the sterile sheath above the aperture.

The assembly where the base further comprises a cavity for at least partially receiving the scanner.

The assembly where the scanner is in communication with a computer device located apart from the reader, where the computer device is capable of receiving and storing information obtained from the medical device upon being scanned by the reader.

The assembly where the sterile sheath is formed of a single piece of transparent plastic.

A tracking assembly comprising:
a reader comprising:
a scanner;
a scanner mounting structure supporting the scanner;
a housing structure that includes a cover with an aperture and a base secured to the cover,
a sheath positioned on the cover; and
a drape permanently secured to the sterile sheath, where the drape and sheath substantially enclose the housing structure,
where the scanner mounting structure is secured to the base, and
where the scanner and scanner mounting structure are substantially enclosed in the housing structure.

A tracking assembly comprising:
a reader comprising:
a scanner;
a scanner mounting structure supporting the scanner;
a housing structure that includes a cover with an aperture and a base secured to the cover,
a sheath positioned on the cover; and
a drape permanently secured to the sterile sheath along a securement band, where the drape and sheath substantially enclose the housing structure,
where the scanner mounting structure is secured to the base, and
where the scanner and scanner mounting structure are substantially enclosed in the housing structure.

The assembly where the drape is permanently secured to the sheath using heat to melt a portion of the drape and the sheath along the securement band to form a bond.

The assembly where the drape is permanently secured to the sheath using a chemical adhesive.

The assembly further including a cavity positioned inside the base, where the scanner is substantially positioned inside the cavity.

The assembly where the scanner includes a scanner housing attached to the scanner mounting structure.

The assembly where the scanner is capable of scanning 2×2 mm etched identifiers.

The assembly where the aperture of the cover corresponds with the focal point of the scanner.

The assembly where the sterile drape is comprised of at least one of elastomer, plastic, rubber, polyethylene, and polypropylene.

The assembly where an optically transparent portion of the sheath is situated in an area above the aperture of the cover.

The assembly where the scanner housing has a lens secured thereto, where the lens includes a front surface, where the front surface is situated between about 3 inches to about 5 inches from the aperture of the cover.

The assembly where the sterile sheath includes a sterile sheath top surface having at least one of a convex portion and a magnifying portion.

The assembly where the sterile sheath is formed of a single piece of transparent plastic.

The assembly where the sterile sheath is disposed of after identifiers have been received for all the medical devices used on and/or implanted in a single patient during an operation.

The assembly where the reader is positionable adjacent to a patient during a surgical procedure.

The assembly where the scanner is connected via a cord to a computer located outside the housing structure.

A tracking assembly comprising:
a reader comprising:
a scanner;
a scanner mounting structure supporting the scanner;
a housing structure that includes a cover with an aperture and a base secured to the cover;
a sheath positioned on the cover; and
a drape permanently secured to the sterile sheath, where the drape and sheath substantially enclose the housing structure,
where the scanner mounting structure is secured to the base, and
where the scanner and scanner mounting structure are substantially enclosed in the housing structure.

The assembly where the sheath is rigid and cylindrical in shape.

The assembly where the sheath is cylindrical in shape and includes a locking mechanism.

The assembly further including a cavity positioned inside the base, where the scanner is substantially positioned inside the cavity.

The assembly where the scanner includes a scanner housing attached to the scanner mounting structure.

The assembly where the scanner is capable of scanning 2×2 mm etched identifiers.

The assembly where the aperture of the cover corresponds with a focal point of the scanner.

The assembly where an optically transparent portion of the sheath is situated in an area above the aperture of the cover.

The assembly where the scanner housing has a lens secured thereto, where the lens includes a front surface, where the front surface is situated between about 3 inches to about 5 inches from the aperture of the cover.

The assembly where the sterile sheath includes a sterile sheath top surface having at least one of a convex portion and a magnifying portion.

The assembly where the sterile sheath is formed of a single piece of transparent plastic.

The assembly where the sterile sheath is disposed of after identifiers have been received for all the medical devices used on and/or implanted in a single patient during an operation.

The assembly where the scanner is connected via a cord to a computer located outside the housing structure.

A method of using a tracking assembly comprising the steps of:
providing a tracking assembly comprising:
a reader comprising:
a scanner;
a scanner mounting structure supporting the scanner; and
a housing structure comprising:
a cover comprising:
an aperture in the cover; and
a base secured to the cover, where the base includes a cavity,
where the scanner mounting structure is positioned in the cavity of the base, and where the scanner and scanner mounting structure are substantially enclosed in the housing structure;
covering the cover with a sterile sheath and further enclosing the reader with a drape secured to the sterile sheath;
positioning the reader adjacent to a surgical patient;
placing an implant having an identifier over the aperture; and
scanning the identifier of the implant to electronically record the implant data.

The method where the medical drape includes a drape upper portion and a drape lower portion, where the drape lower portion extends beyond the housing structure.

The method where further enclosing the reader with the drape further includes unfolding the drape over the housing structure and extending a lower portion over the drape to at least partially cover one or more cords extending from the housing structure.

The method further including enclosing the housing structure and all associated cords that extending therefrom, for a distance of at least four feet from the housing structure.

The method where the drape is in a telescopically folded configuration prior to unfolding over the housing structure.

A method of tracking a medical device comprising:
creating a patient profile;
creating an operating profile comprising at least one surgical site;
providing a tracking assembly comprising a reader, the reader comprising a scanner, a housing enclosing the scanner, and a medical drape;
placing a medical device having an identifier over the reader;
scanning the identifier of the medical device to electronically record the medical device data;
associating the scanned medical device data with the at least one surgical site; and using the medical device on a patient on the at least one surgical site.

The method wherein the reader comprises a transparent sterile sheath and the medical drape is attached to the transparent sterile sheath.

The method wherein the reader further comprises a proximity sensor and the scanner is activated by the proximity sensor.

The method wherein the reader further comprises a light ring which is activated by the proximity sensor.

The method wherein the reader further comprises a self-contained removable battery enclosed in the housing, wherein the battery is capable of running the scanner for at least 24 hours.

The method wherein the self-contained removable battery is rechargeable.

The method wherein the reader is configured with firmware to enable the scanner to accurately read 1 mm$^2$ 2D data matrix identifiers.

The method wherein the step of creating a patient profile includes entering a value for a medical procedure start time.

The method further comprising the step of providing a computer.

The method wherein the steps of creating a patient profile and creating an operating profile are completed using the computer.

The method wherein the steps are performed in the following order:
providing a computer;
providing a tracking assembly comprising the reader;
creating a patient profile;
creating an operating profile comprising at least one surgical site;
placing a medical device having an identifier over the reader;
scanning the identifier of the medical device to electronically record the medical device data;
associating the scanned medical device data with the at least one surgical site; and
using the medical device on a patient on the at least one surgical site.

The method wherein the step of associating the scanned medical device data with the at least one surgical site includes assigning the medical device a status.

The method the status is selected from the group consisting of assigned, unassigned, broken, discarded, implanted, multi-zone and combinations thereof.

The method further comprising the step of entering a medical procedure end time into the patient profile, with the proviso that the step of entering a medical procedure end time into the patient profile may not be completed until the scanned medical device data is assigned a medical device status of unassigned, broken, discarded or implanted.

The method wherein the steps of placing a medical device having an identifier over the reader, scanning the identifier of the medical device to electronically record the medical device data and associating the scanned medical device data with the at least one surgical site are repeated for every medical device used during a medical procedure.

The method further comprising the step of entering a medical procedure end time into the patient profile, with the proviso that the step of entering a medical procedure end time into the patient profile may not be completed until the scanned medical device data associated with every medical device used during the medical procedure is assigned a medical device status of unassigned, broken, discarded or implanted.

The method wherein the computer is configured to communicate with external systems and databases, including at least one external system or database selected from the group consisting of electronic health records, electronic medical records, hospital and clinic databases containing patient information, databases containing scheduling information, databases containing physician and medical staff information, databases containing hospital inventory information, payer systems, databases and records of the manufacturer of the medical device, insurance and reimbursement systems, and government databases, such as the Food and Drug Administration.

The method wherein the method takes place in a sterile field.

A method of tracking a medical device comprising:
providing a tracking assembly comprising a reader, the reader comprising a scanner, a housing enclosing the scanner, and a medical drape;
covering the reader with the medical drape;
placing the reader covered with the medical drape in a sterile field;
providing a computer;
creating a patient profile using the computer, wherein the patient profile includes a value for a medical procedure start time;
creating an operating profile comprising at least one surgical site using the computer;
placing a medical device having an identifier over the reader;
scanning the identifier of the medical device to electronically record the medical device data in memory in the computer, wherein the scanner communicates with the computer using Bluetooth;
associating the scanned medical device data with the at least one surgical site using the computer, whereby the scanned medical device is assigned a status of assigned;
using the medical device on a patient on the at least one surgical site;
changing the status of the medical device to a status selected from the group consisting of unassigned, broken, discarded or implanted; and
entering a value for a medical procedure end time into the patient profile.

The method wherein the reader further comprises a self-contained, rechargeable removable battery enclosed in the housing, wherein the battery is capable of running the scanner for at least 24 hours.

The method wherein the computer is configured with software enabling the computer to communicate with a healthcare provider's or healthcare system's existing EMR and/or EHR system(s).

A method for tracking a medical device comprising:
providing a tracking assembly comprising a reader, the reader having a scanner, a housing enclosing the scanner, and a medical drape;
placing a medical device having an identifier over the reader;
scanning the identifier of the medical device to electronically record the medical device data;
transmitting the medical device data to one or more databases or record systems; and using the medical device in a medical procedure on a subject.

Although the invention has been described with certain detail through the preceding description of the preferred embodiments, this detail is for the primary purpose of illustration. Many variations and modifications can be made by one skilled in the art without departing from the spirit and scope of the invention as described in the following claims.

What is claimed is:

1. A method of tracking a medical device comprising, in order, the steps of:
providing a tracking assembly comprising a reader, the reader comprising a scanner, a housing enclosing the scanner, and a medical drape;
covering the reader with the medical drape;
placing the reader covered with the medical drape in a sterile field;
providing a computer;
creating a patient profile using the computer, wherein the patient profile includes a value for a medical procedure start time;
initiating a medical procedure on a patient;
creating an operating profile comprising at least one surgical site using the computer;
placing a medical device having an identifier over the reader;
scanning the identifier of the medical device to electronically record medical device data associated with the medical device in memory in the computer, wherein the scanner communicates with the computer using Bluetooth;
obtaining additional medical device data from at least one additional database selected from the group consisting of hospital and clinic databases, medical device manufacturer and distributor databases, payer databases and government databases, wherein the computer wirelessly communicates with the at least one additional database;
electronically recording the additional medical device data in memory in the computer;
associating the scanned medical device data and additional medical device data with the at least one surgical site using the computer, whereby the scanned medical device is assigned a first status of assigned
using the medical device on the patient on the at least one surgical site;
changing the status of the medical device to a second status, wherein (a) when the medical device is an implant, the second status is selected from the group consisting of implanted, broken and discarded, and (b) when the medical device is a medical tool, the second status is selected from the group consisting of unassigned, broken and discarded, the second status indicates the medical device is either implanted or no longer in use;
completing the medical procedure; and
entering a value for a medical procedure end time into the patient profile,
wherein the step of changing the status of the medical device to the second status occurs after initiating the medical procedure and during the medical procedure in real time, and wherein the step of entering value for a medical procedure end time occurs after, and only after, changing the status of the medical device to the second status.

2. The method of claim 1, wherein the reader comprises a transparent sterile sheath and the medical drape is attached to the transparent sterile sheath.

3. The method of claim 1, wherein the reader further comprises a light ring which is activated by the proximity sensor.

4. The method of claim 1, wherein the steps of placing a medical device having an identifier over the reader, scanning the identifier of the medical device to electronically record the medical device data and associating, the scanned medical device data with the at least one surgical site are repeated for every medical device used during a medical procedure.

5. The method claim 1, wherein the computer is configured to communicate with external systems and databases, including at least one external system or database selected from the group consisting of electronic health records, electronic medical records, a hospital database containing patient information, a hospital database containing scheduling information, a hospital database containing physician information, a hospital database containing medical staff information, a hospital database containing inventory information, a clinic database containing patient information, a clinic database containing scheduling information, a clinic database containing physician information, a clinic database containing medical staff information, a clinic database containing inventory information, a payer system, a database or records of the manufacturer of the medical device, an insurance system, a reimbursement system, and a government database.

6. The method of claim 1, wherein the method takes place in a sterile field.

7. The method of claim 1, wherein the reader further comprises a self-contained, rechargeable removable battery enclosed in the housing, wherein the battery is capable of running the scanner for at least 24 hours.

8. The method of claim 1, further comprising:
transmitting the medical device data to one or more databases or records.

9. The method of claim 1, wherein the step of creating a patient profile using the computer occurs while the reader covered with the medical drape is in the sterile field.

10. The method of claim 1, wherein the second status is selected from the group consisting of unassigned, broken, discarded and implanted.

11. The method of claim 1, further including the step of entering a note doting the medical procedure.

12. The method of claim 11, wherein, upon entering a value for the medical procedure end time, a user is prompted to review the note before being exported to the patient profile.

* * * * *